(12) United States Patent
Feezor et al.

(10) Patent No.: US 11,504,111 B2
(45) Date of Patent: Nov. 22, 2022

(54) DEVICES, SYSTEMS, AND METHODS FOR ATTACHING SOFT TISSUE TO BONE TISSUE

(71) Applicant: Stabilynx, Inc., Menlo Park, CA (US)

(72) Inventors: Christopher Feezor, Menlo Park, CA (US); Michael Rosenthal, Menlo Park, CA (US); Joseph P. Donahue, Menlo Park, CA (US)

(73) Assignee: STABILYNX, INC., Menlo Park, CA (US)

( * ) Notice: Subject to any disclaimer, the term of this patent is extended or adjusted under 35 U.S.C. 154(b) by 173 days.

(21) Appl. No.: 16/827,581

(22) Filed: Mar. 23, 2020

(65) Prior Publication Data

US 2021/0045730 A1 Feb. 18, 2021

Related U.S. Application Data

(63) Continuation of application No. 16/417,571, filed on May 20, 2019, now Pat. No. 10,595,853, which is a
(Continued)

(51) Int. Cl.
*A61B 17/04* (2006.01)
*A61B 17/06* (2006.01)

(52) U.S. Cl.
CPC ...... *A61B 17/0401* (2013.01); *A61B 17/0485* (2013.01); *A61B 17/06166* (2013.01);
(Continued)

(58) Field of Classification Search
CPC ............ A61B 17/0401; A61B 17/0485; A61B 17/06166; A61B 2017/044;
(Continued)

(56) References Cited

U.S. PATENT DOCUMENTS 5,250,053 A 10/1993 Snyder
5,279,311 A 1/1994 Snyder
(Continued)

FOREIGN PATENT DOCUMENTS

EP 2 436 316 4/2012
EP 2 455 003 5/2012
(Continued)

OTHER PUBLICATIONS

Millett, M.D., M.Sc., Peter J. et al, Mattress Double Anchor Footprint Repair: A Novel, Arthroscopic Rotator Cuff Repair Technique, Arthroscopy: The Journal of Arthroscopic and Related Surgery, Oct. 2004, pp. 875-879, vol. 20, No. 8, Arthroscopy Association of North America.
(Continued)

*Primary Examiner* — Tuan V Nguyen
(74) *Attorney, Agent, or Firm* — Knobbe, Martens, Olson & Bear, LLP

(57) ABSTRACT

A suture anchoring device for fixing a soft tissue to a bone tissue is disclosed that enables the exchange of sutures between anchors after implantation. The suture anchoring device may include a body that is inserted into the bone tissue, a suture exchange fitting situation within a passage formed within the body, and one or more pre-loaded sutures looped through the suture exchange fitting and projecting proximally from a proximal opening formed in the body. Surgical kits and surgical methods for performing various repair procedures using one or more suture anchoring device are also disclosed.

22 Claims, 48 Drawing Sheets

Related U.S. Application Data continuation of application No. 15/984,294, filed on May 18, 2018, now Pat. No. 10,292,696, which is a continuation of application No. 15/852,925, filed on Dec. 22, 2017, now Pat. No. 10,327,755, which is a continuation of application No. 15/124,344, filed as application No. PCT/US2015/016671 on Feb. 19, 2015, now Pat. No. 9,861,353, said application No. 15/852,925 is a continuation of application No. 14/610,711, filed on Jan. 30, 2015, now abandoned, which is a continuation-in-part of application No. PCT/US2013/053524, filed on Aug. 3, 2013, which is a continuation of application No. 13/566,845, filed on Aug. 3, 2012, now abandoned.

(60) Provisional application No. 62/093,827, filed on Dec. 18, 2014, provisional application No. 62/000,379, filed on May 19, 2014, provisional application No. 61/949,485, filed on Mar. 7, 2014, provisional application No. 61/817,841, filed on Apr. 30, 2013.

(52) U.S. Cl.
CPC . *A61B 2017/044* (2013.01); *A61B 2017/0414* (2013.01); *A61B 2017/0448* (2013.01); *A61B 2017/0458* (2013.01)

(58) Field of Classification Search
CPC .... A61B 2017/0411; A61B 2017/0412; A61B 2017/0445; A61B 2017/0435; A61B 2017/0401; A61B 2017/0414; A61B 2017/0409; A61B 2017/0448; A61B 2017/0451
See application file for complete search history.

(56) References Cited

U.S. PATENT DOCUMENTS

| | | | |
|---|---|---|---|
| 5,534,011 A | 7/1996 | Greene, Jr. et al. | |
| 5,584,835 A | 12/1996 | Greenfield | |
| 5,591,207 A | 1/1997 | Coleman | |
| 5,906,624 A | 5/1999 | Wenstrom, Jr. | |
| 5,957,953 A | 9/1999 | DiPoto et al. | |
| 6,508,830 B2 | 1/2003 | Steiner | |
| 6,520,980 B1 | 2/2003 | Foerster | |
| 6,652,563 B2 | 11/2003 | Dreyfuss | |
| 6,932,834 B2 | 8/2005 | Lizardi et al. | |
| 7,320,701 B2 | 1/2008 | Haut et al. | |
| 7,322,978 B2 | 1/2008 | West, Jr. | |
| 7,637,926 B2 | 12/2009 | Foerster et al. | |
| 7,682,374 B2 | 3/2010 | Foerster et al. | |
| 7,713,286 B2 | 5/2010 | Singhatat | |
| 7,828,820 B2 | 11/2010 | Stone et al. | |
| 7,981,140 B2 | 7/2011 | Burkhart | |
| 8,012,174 B2 | 9/2011 | ElAttrache et al. | |
| 8,114,127 B2 | 2/2012 | West, Jr. | |
| 8,137,381 B2 | 3/2012 | Foerster et al. | |
| 8,231,653 B2 | 7/2012 | Dreyfuss | |
| 8,298,262 B2 | 10/2012 | Stone et al. | |
| 8,317,828 B2 | 11/2012 | Martinek et al. | |
| 8,317,829 B2 | 11/2012 | Foerster et al. | |
| 8,348,975 B2 | 1/2013 | Dreyfuss | |
| 8,366,744 B2 | 2/2013 | Bojarski et al. | |
| 8,394,123 B2 | 3/2013 | Cauldwell et al. | |
| 8,409,252 B2 | 4/2013 | Lomardo et al. | |
| 8,414,613 B2 | 4/2013 | Huxel et al. | |
| 8,425,536 B2 | 4/2013 | Foerster et al. | |
| 8,444,672 B2 | 5/2013 | Foerster | |
| 8,454,654 B2 | 6/2013 | Ferragamo et al. | |
| 8,460,340 B2 | 6/2013 | Sojka et al. | |
| 8,469,998 B2 | 6/2013 | Sojka et al. | |
| 8,506,596 B2 | 8/2013 | Stone et al. | |
| 8,512,378 B2 | 8/2013 | Green et al. | |
| 8,545,535 B2 | 10/2013 | Hirotsuka et al. | |
| 8,545,536 B2 | 10/2013 | Mayer et al. | |
| 8,597,328 B2 | 12/2013 | Cauldwell et al. | |
| 8,608,777 B2 | 12/2013 | Kaiser et al. | |
| 8,613,756 B2 | 12/2013 | Lizardi et al. | |
| 9,861,353 B2 | 1/2018 | Feezor et al. | |
| 10,292,696 B2 | 5/2019 | Feezor et al. | |
| 10,595,853 B2 | 3/2020 | Feezor et al. | |
| 2002/0052629 A1 | 5/2002 | Morgan et al. | |
| 2002/0052630 A1 | 5/2002 | Morgan et al. | |
| 2002/0173822 A1 | 11/2002 | Justin et al. | |
| 2003/0065361 A1 | 4/2003 | Dreyfuss | |
| 2004/0106925 A1 | 6/2004 | Culbert | |
| 2004/0111117 A1 | 6/2004 | Colleran et al. | |
| 2004/0267317 A1 | 12/2004 | Higgins et al. | |
| 2005/0245932 A1 | 11/2005 | Fanton et al. | |
| 2006/0100630 A1* | 5/2006 | West, Jr. | A61B 17/863 606/232 |
| 2006/0106423 A1 | 5/2006 | Weisel et al. | |
| 2006/0247641 A1 | 11/2006 | Re et al. | |
| 2006/0271105 A1 | 11/2006 | Foerster et al. | |
| 2006/0282083 A1 | 12/2006 | Fanton et al. | |
| 2007/0060922 A1 | 3/2007 | Dreyfuss | |
| 2007/0142835 A1 | 6/2007 | Green et al. | |
| 2007/0173845 A1 | 7/2007 | Kim | |
| 2007/0191849 A1 | 8/2007 | ElAttrache et al. | |
| 2007/0219558 A1 | 9/2007 | Deutsch | |
| 2007/0225719 A1 | 9/2007 | Stone et al. | |
| 2007/0255317 A1 | 11/2007 | Fanton et al. | |
| 2007/0288023 A1 | 12/2007 | Pellegrino et al. | |
| 2008/0125815 A1 | 5/2008 | Heaven et al. | |
| 2008/0262544 A1 | 10/2008 | Burkhart | |
| 2008/0275469 A1 | 11/2008 | Fanton et al. | |
| 2008/0306510 A1 | 12/2008 | Stchur | |
| 2009/0030466 A1 | 1/2009 | Strauss | |
| 2009/0099598 A1 | 4/2009 | McDevitt et al. | |
| 2009/0187216 A1 | 7/2009 | Schmieding et al. | |
| 2009/0192546 A1 | 7/2009 | Schmieding et al. | |
| 2009/0287246 A1 | 11/2009 | Cauldwell et al. | |
| 2009/0318960 A1 | 12/2009 | Burkhart | |
| 2010/0004683 A1 | 1/2010 | Hoof et al. | |
| 2010/0016869 A1 | 1/2010 | Paulk et al. | |
| 2010/0016893 A1 | 1/2010 | Fanton | |
| 2010/0049249 A1 | 2/2010 | Lombardo | |
| 2010/0063541 A1 | 3/2010 | Brunelle et al. | |
| 2010/0063542 A1 | 3/2010 | Van Der Burg et al. | |
| 2010/0121348 A1 | 5/2010 | Van Der Burg et al. | |
| 2010/0160962 A1 | 6/2010 | Dreyfuss et al. | |
| 2010/0160963 A1 | 6/2010 | Fallin et al. | |
| 2010/0179573 A1 | 7/2010 | Levinsohn et al. | |
| 2010/0191284 A1 | 7/2010 | Dreyfuss et al. | |
| 2010/0222812 A1 | 9/2010 | Stone et al. | |
| 2010/0249833 A1 | 9/2010 | Dreyfuss | |
| 2010/0249834 A1 | 9/2010 | Dreyfuss | |
| 2010/0292731 A1 | 11/2010 | Gittings et al. | |
| 2010/0292732 A1 | 11/2010 | Hirotsuka et al. | |
| 2010/0292733 A1 | 11/2010 | Hendricksen et al. | |
| 2011/0118762 A1 | 5/2011 | Dooney, Jr. et al. | |
| 2011/0190815 A1 | 8/2011 | Saliman | |
| 2011/0208240 A1 | 8/2011 | Stone et al. | |
| 2011/0238111 A1 | 9/2011 | Frank | |
| 2011/0238113 A1 | 9/2011 | Fanton et al. | |
| 2012/0004687 A1 | 1/2012 | Schmieding et al. | |
| 2012/0041484 A1 | 2/2012 | Briganti et al. | |
| 2012/0053626 A1 | 3/2012 | Koepke | |
| 2012/0053627 A1 | 3/2012 | Sojka et al. | |
| 2012/0053628 A1 | 3/2012 | Sojka et al. | |
| 2012/0053629 A1 | 3/2012 | Reiser et al. | |
| 2012/0065677 A1 | 3/2012 | West, Jr. | |
| 2012/0078298 A1 | 3/2012 | Sklar | |
| 2012/0083841 A1 | 4/2012 | DiMatteo et al. | |
| 2012/0101524 A1 | 4/2012 | Bennett | |
| 2012/0101526 A1 | 4/2012 | Bennett | |
| 2012/0130422 A1 | 5/2012 | Hootstein | |
| 2012/0130423 A1 | 5/2012 | Sengun et al. | |
| 2012/0130424 A1 | 5/2012 | Sengun et al. | |
| 2012/0150225 A1 | 6/2012 | Burkhart et al. | |
| 2012/0150226 A1 | 6/2012 | Burkhart et al. | |
| 2012/0158051 A1 | 6/2012 | Foerster | |

(56) References Cited

U.S. PATENT DOCUMENTS

| | | |
|---|---|---|
| 2012/0165868 A1 | 6/2012 | Burkhart et al. |
| 2012/0179199 A1 | 7/2012 | Hernandez et al. |
| 2012/0191134 A1 | 7/2012 | Martin |
| 2012/0232590 A1 | 9/2012 | Miller et al. |
| 2012/0253389 A1 | 10/2012 | Sengun et al. |
| 2013/0023928 A1 | 1/2013 | Dreyfuss |
| 2013/0060280 A1 | 3/2013 | Wolf et al. |
| 2013/0072975 A1 | 3/2013 | Van Der Burg et al. |
| 2013/0072976 A1 | 3/2013 | Van Der Burg et al. |
| 2013/0085528 A1 | 4/2013 | DiMatteo et al. |
| 2013/0096611 A1 | 4/2013 | Sullivan |
| 2013/0103083 A1 | 4/2013 | Baird |
| 2013/0110165 A1 | 5/2013 | Burkhait et al. |
| 2013/0123842 A1 | 5/2013 | Chan et al. |
| 2013/0123843 A1 | 5/2013 | Chan et al. |
| 2013/0144334 A1 | 6/2013 | Bouduban et al. |
| 2013/0144335 A1 | 6/2013 | Sandow |
| 2013/0150885 A1 | 6/2013 | Dreyfuss |
| 2013/0158596 A1 | 6/2013 | Miller et al. |
| 2013/0158598 A1 | 6/2013 | Lizardi |
| 2013/0165972 A1 | 6/2013 | Sullivan |
| 2013/0184747 A1 | 7/2013 | Sojka et al. |
| 2013/0184748 A1 | 7/2013 | Sojka et al. |
| 2013/0190818 A1 | 7/2013 | Norton |
| 2013/0197575 A1 | 8/2013 | Karapetian et al. |
| 2013/0197576 A1 | 8/2013 | Catania et al. |
| 2013/0197577 A1 | 8/2013 | Wolf et al. |
| 2013/0197578 A1 | 8/2013 | Gregoire et al. |
| 2013/0197579 A1 | 8/2013 | Foerster et al. |
| 2013/0237997 A1 | 9/2013 | Arai et al. |
| 2013/0261664 A1 | 10/2013 | Spenciner et al. |
| 2013/0267998 A1 | 10/2013 | Vijay et al. |
| 2013/0268001 A1 | 10/2013 | Catanese, III et al. |
| 2013/0282058 A1 | 10/2013 | ElAttrache et al. |
| 2013/0296934 A1 | 11/2013 | Sengun |
| 2013/0317546 A1 | 11/2013 | Brown |
| 2013/0325011 A1 | 12/2013 | Cleveland et al. |
| 2013/0325064 A1 | 12/2013 | Lizardi et al. |
| 2013/0331885 A1 | 12/2013 | Stone et al. |
| 2013/0338710 A1 | 12/2013 | Heaven et al. |
| 2013/0345746 A1 | 12/2013 | Gittings et al. |
| 2013/0345749 A1 | 12/2013 | Sullivan et al. |
| 2013/0345750 A1 | 12/2013 | Sullivan |
| 2014/0039551 A1 | 2/2014 | Donahue |
| 2014/0081324 A1 | 3/2014 | Sengun |
| 2014/0257385 A1 | 9/2014 | Lunn et al. |
| 2015/0012015 A1 | 1/2015 | Berelsman et al. |
| 2015/0272567 A1 | 10/2015 | Feezor et al. |
| 2017/0071592 A1 | 3/2017 | Feezor et al. |

FOREIGN PATENT DOCUMENTS

| | | |
|---|---|---|
| EP | 2 767 241 | 8/2014 |
| WO | WO 02/021998 | 3/2002 |
| WO | WO 06/037131 | 4/2006 |

OTHER PUBLICATIONS

Smith & Nephew, Footprint 123, "Rotator cuff repair using Smith & Nephew Footprint Suture Anchor", YouTube Jun. 30, 2011 (retrieved from internet on Nov. 1, 2013 at http://youtube/y2WCVa3GFcs).

* cited by examiner

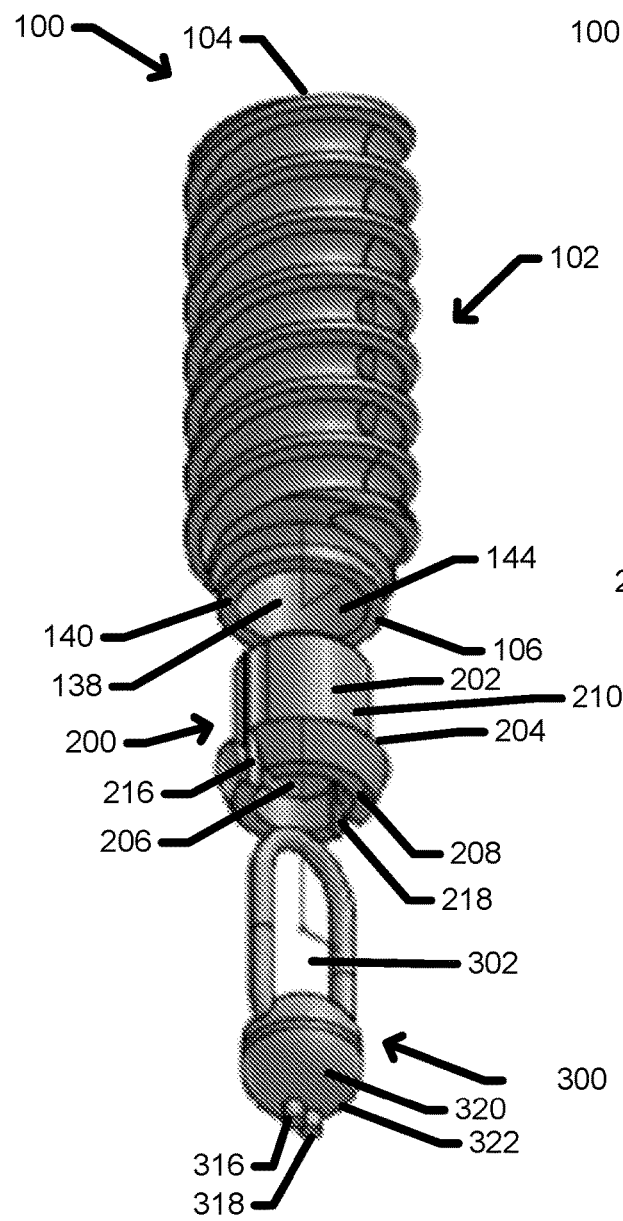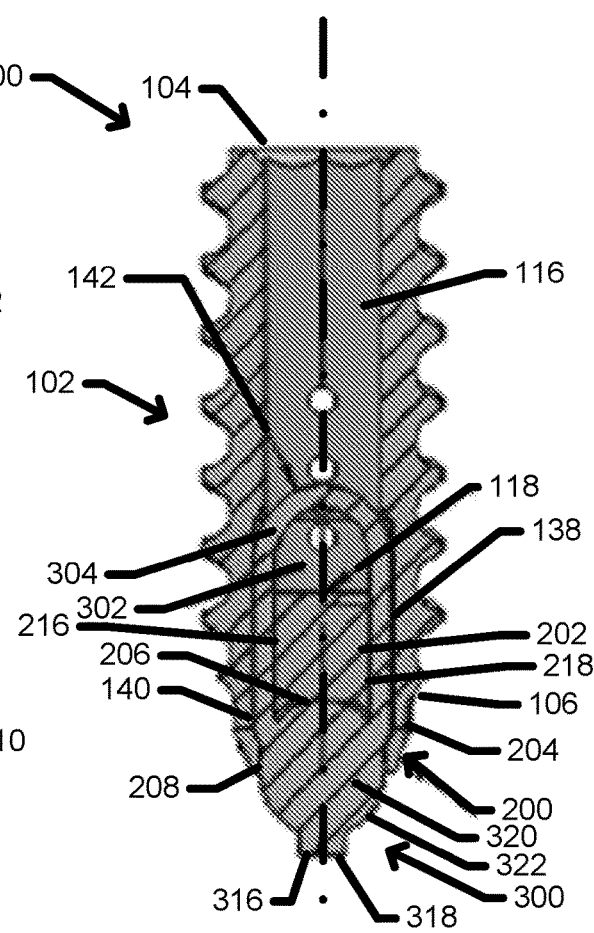
FIG. 7
FIG. 8

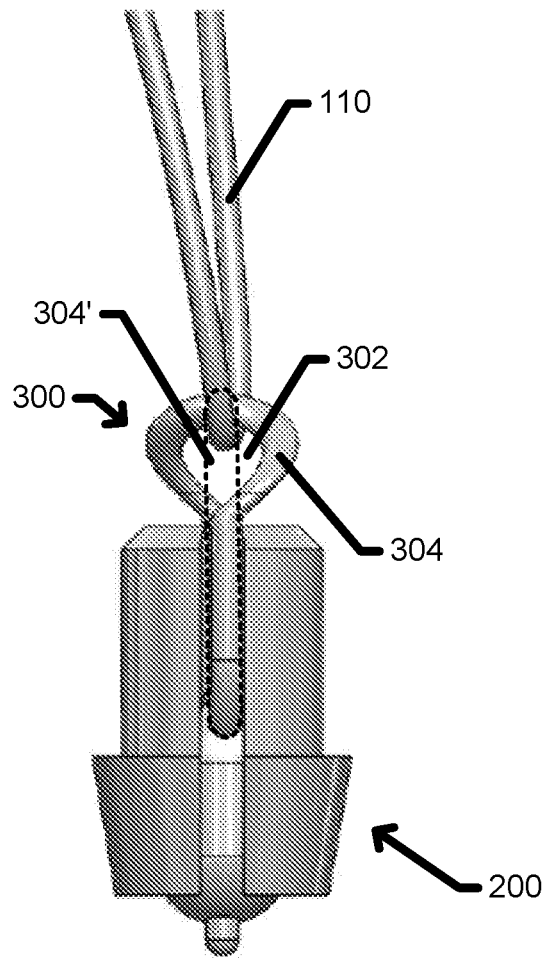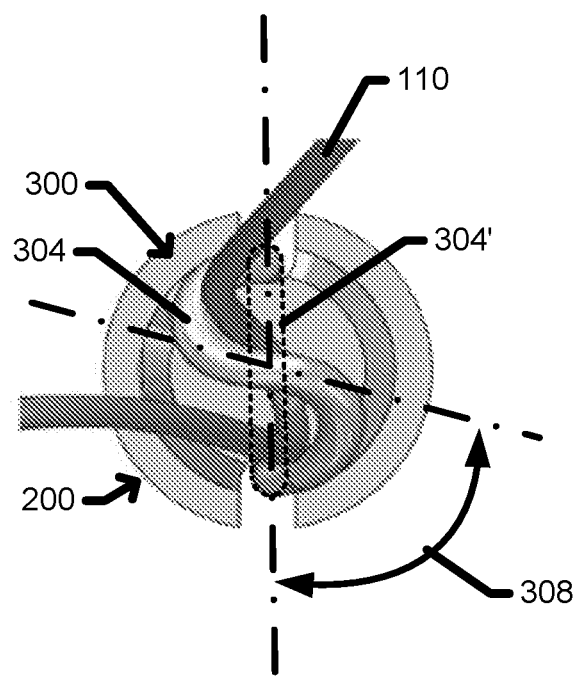
FIG. 12
FIG. 13

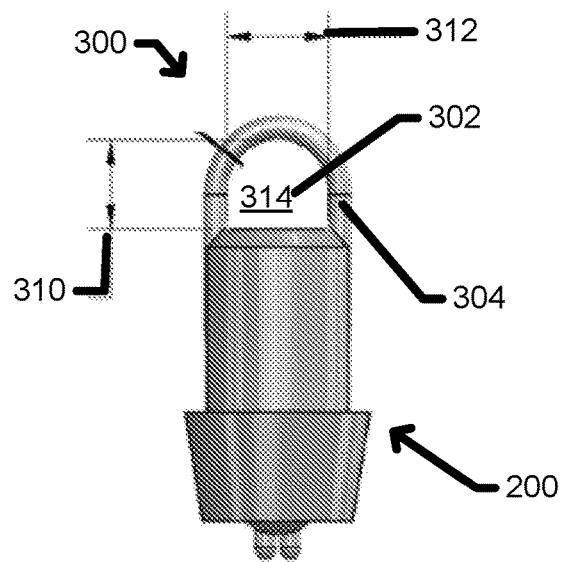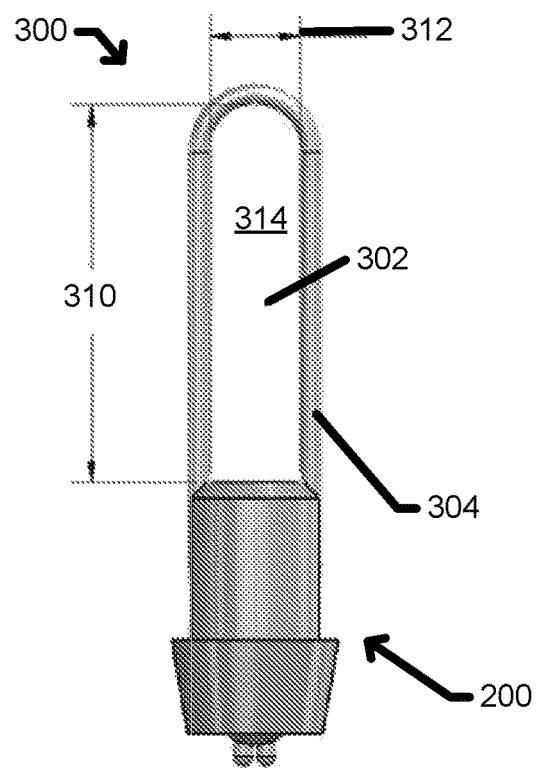
FIG. 14          FIG. 15

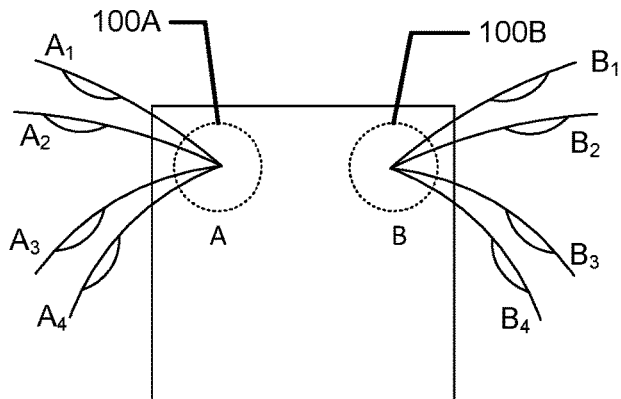
FIG. 46A
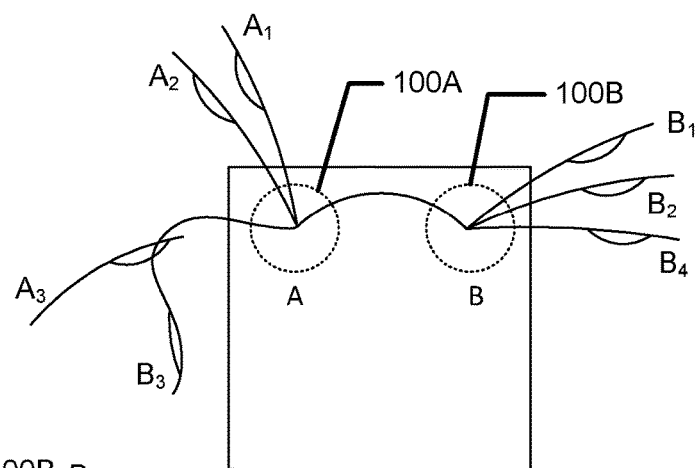
FIG. 46B
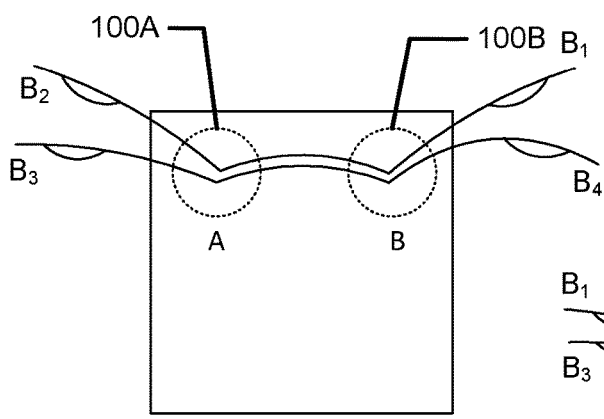
FIG. 46C
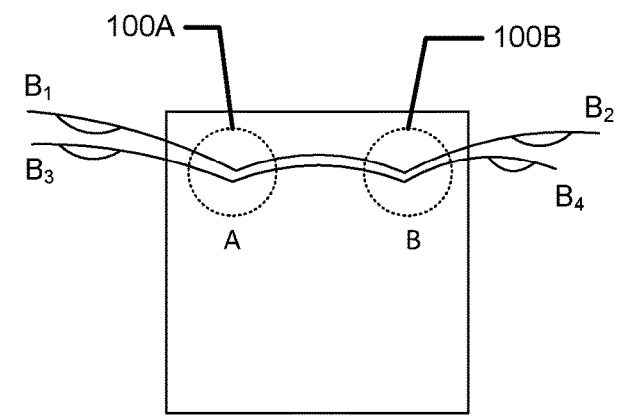
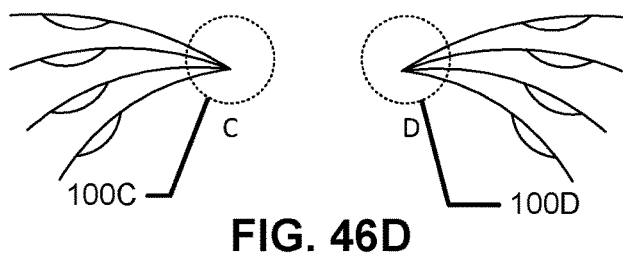
FIG. 46D

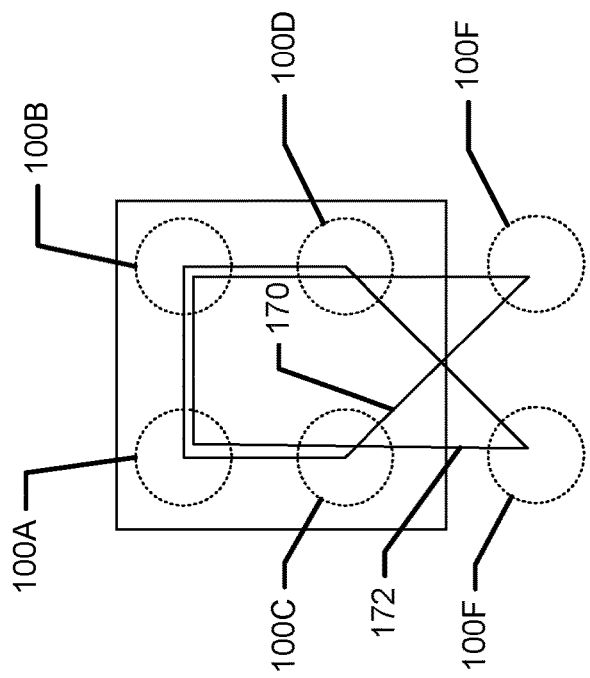
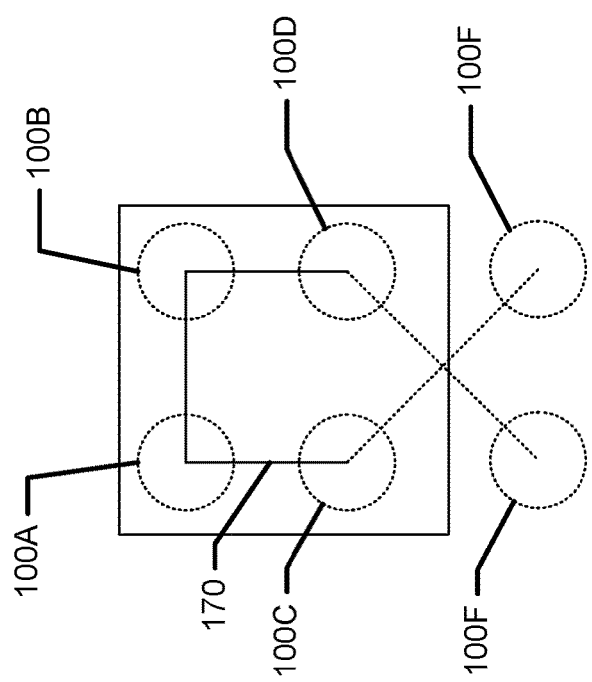
FIG. 47B
FIG. 47A

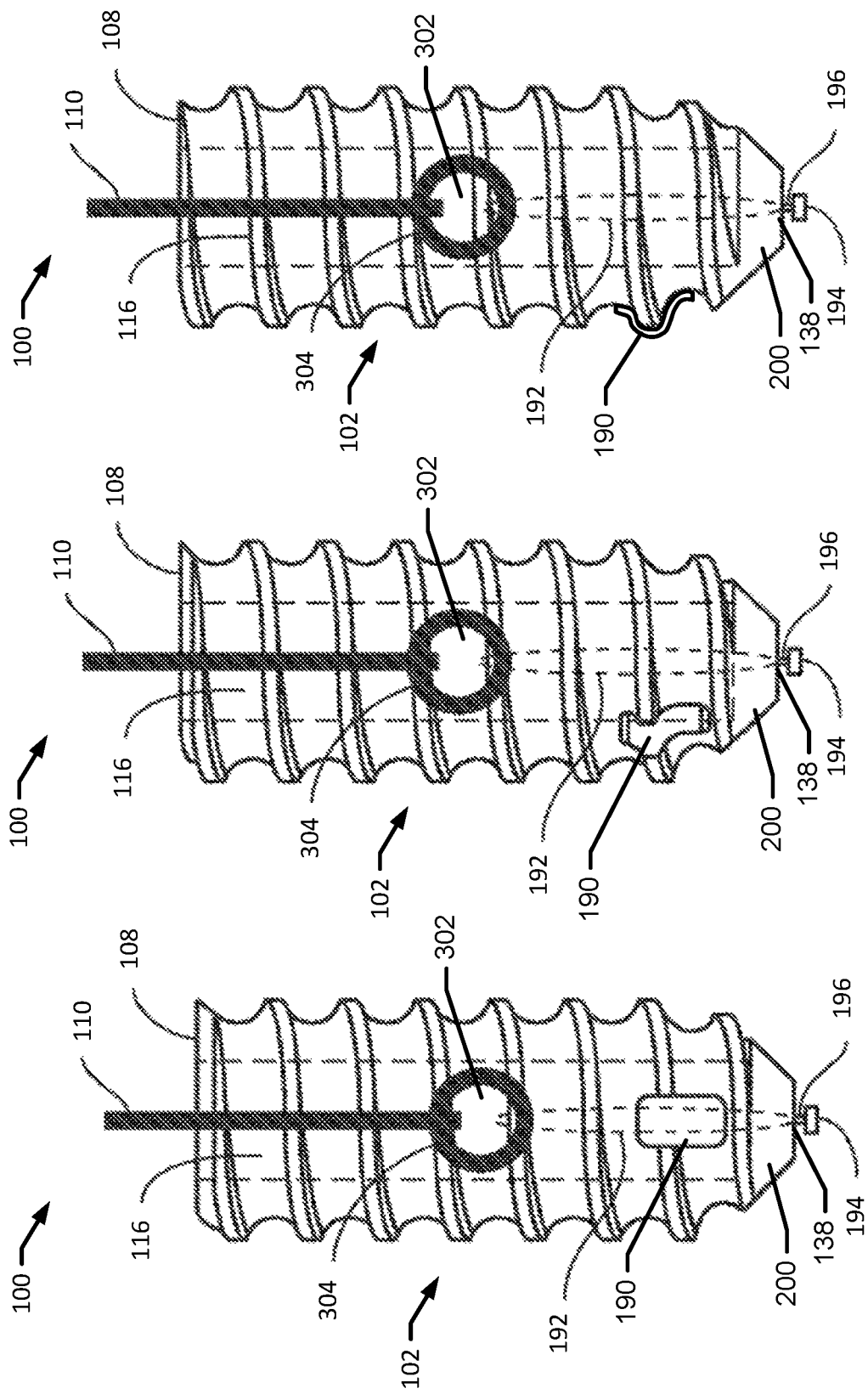

DEVICES, SYSTEMS, AND METHODS FOR ATTACHING SOFT TISSUE TO BONE TISSUE

CROSS REFERENCE TO RELATED APPLICATIONS

This application is a continuation of U.S. application Ser. No. 16/417,571, filed Mar. 4, 2020, now U.S. Pat. No. 10,595,853, which is a continuation of U.S. application Ser. No. 15/984,294 filed May 18, 2018, now U.S. Pat. No. 10,292,696, which is a continuation of U.S. application Ser. No. 15/852,925 filed Dec. 22, 2017, now U.S. Pat. No. 10,327,755, which is a continuation of U.S. application Ser. No. 15/124,344 filed Sep. 7, 2016, now U.S. Pat. No. 9,861,353, which application is a national stage entry of PCT Application No. PCT/US2015/016671 filed Feb. 19, 2015, which application claims priority to U.S. provisional patent application No. 62/093,827 filed Dec. 18, 2014 entitled "DEVICES, SYSTEMS, AND METHODS FOR ATTACHING SOFT TISSUE TO BONE TISSUE;" U.S. provisional patent application No. 62/000,379, which was filed May 19, 2014, entitled "DOUBLE-LOOPED SUTURE;" and U.S. provisional patent application 61/949,485, which was filed Mar. 7, 2014, entitled "DOUBLE-LOOPED SUTURE."

U.S. application Ser. No. 15/852,925 is also a continuation of U.S. patent application Ser. No. 14/610,711 filed 30 Jan. 2015, which application is a continuation-in-part of PCT Application No. PCT/US2013/053524, with an international filing date of Aug. 3, 2013, entitled "SUTURE ANCHOR DEVICE AND METHODS OF USE." PCT Application No. PCT/US2013/053524 claims priority to U.S. patent application Ser. No. 13/566,845 which was filed Aug. 3, 2012 and to U.S. provisional patent application 61/817,841 which was filed Apr. 30, 2013.

This application is also a continuation of U.S. patent application Ser. No. 14/610,711 filed 30 Jan. 2015, which application is a continuation-in-part of PCT Application No. PCT/US2013/053524, with an international filing date of Aug. 3, 2013, entitled "SUTURE ANCHOR DEVICE AND METHODS OF USE." PCT Application No. PCT/US2013/053524 claims priority to U.S. patent application Ser. No. 13/566,845 which was filed Aug. 3, 2012 and to U.S. provisional patent application 61/817,841 which was filed Apr. 30, 2013.

Each of the foregoing applications is hereby incorporated in its entirety into the present application.

FIELD OF THE INVENTION

The present invention generally relates to medical devices and to surgical implements. More particularly, preferred embodiments of the invention relate to suture anchor devices and methods for using the same.

BACKGROUND

Soft tissue, such as tendons or ligaments, is typically displaced from its usual position in relation to the bone due to injury such as rupturing or tearing. Rotator cuffs, elbows, knees, ankles, and other joints are particularly prone to this type of injury. Injuries can be treated by attaching the soft tissue to the bone. Attaching soft tissue to bone may make use of suture anchors. Generally, a bone anchor with pre-loaded sutures is deployed into bone by inserting the anchor into an opening drilled into the bone. The pre-loaded sutures are used to attach the soft tissue to the bone by suture fixation techniques such as knot-tying, or by insertion of the suture into a knotless anchor for fixation.

Surgical anchor repairs suffer risk of biomechanical failure. Reported failures include suture cutting through bone tunnels, suture breakage, knot slippage, suture anchor pull out, and soft tissue failure at the suture-tendon junction. There is a need for a suture anchor device and method of use that will lower the risk of such biomechanical failures.

SUMMARY OF THE INVENTION

In one aspect, a tissue anchor is provided that includes a body and a flexible elongated element. The body may include a proximal end, a distal end opposite the proximal end, a proximal opening at the proximal end, a distal opening at the distal end, and a passage extending longitudinally through the body between the proximal and distal openings. The flexible elongated element may at least contribute to the defining of an aperture that opens in a direction substantially perpendicular to a longitudinal axis of the passage. The flexible elongated element may be secured to the body at first and second spaced-apart locations to facilitate the aperture being maintained in an open condition. The first and second spaced-apart locations may include a first side of the passage and a second side of the passage opposite the first side of the passage. The flexible elongated element may be secured to the each side of the passage via a ring, hook or loop. The body may further include a distal tip that may be at least one of received or configured to be received in the distal opening. The first and second spaced-apart locations may include a first side of the distal tip and a second side of the distal tip opposite the first side of the distal tip. The body may further include a distal tip that may be at least one of received or configured to be received in the distal opening. The flexible elongated element may include a first tail and a second tail spaced-apart from the first tail by the first tail and the second tail respectively intersecting the distal tip at the first and second spaced-apart locations thereby facilitating the aperture being maintained in the open condition. When the distal tip is received in the distal opening, the aperture may be located in the passage proximal the distal tip. The distal tip may include a molded material; a distal region of the first tail and a distal region of the second tail may be molded into the molded material at the first and second spaced-apart locations. The distal tip may be configured such that implantation forces exerted on the distal tip may enhance the extent to which the distal tip may be received in the distal opening. The first and second spaced-apart locations respectively may include first and second spaced-apart channels in the distal tip, and a distal region of the first tail and a distal region of the second tail may be respectively located in the first and second spaced-apart channels. The first spaced-apart channel may include a groove defined in an outer surface of the distal tip and the distal region of the first tail may extend through the groove, which may open against an inner wall surface defining the passage when the distal tip is received in the distal opening. The first spaced-apart channel may include a lumen defined in the distal tip and the distal region of the first tail may extend through the lumen. The first and second tails may be distally joined together via a knot. The knot may be coated or impregnated with a polymer, epoxy or adhesive. The first and second tails may be part of a continuous loop of the flexible elongated element. The first and second tails may extend into each other in a continuous manner. The first and second tails may be distally joined together via a joining member extending about the at least portions of the first and second tails. The joining member may be at least one of crimped or molded onto the first and second tails. The distal tip may include a distal recess in which the joining member may be seated. The distal tip may include a proximal shaft opposite the distal recess, the distal tip being received in the distal opening on account of the proximal shaft being received in the distal opening and residing in the passage. The proximal shaft may form an interference fit with at least one of the distal opening or the passage. The first and second spaced-apart channels may extend longitudinally along the proximal shaft. The aperture may be defined between the flexible elongated element and a proximal end of the proximal shaft of the distal tip. A maximum height of the aperture in a non-deflected state and extending parallel to the longitudinal axis of the passage may be defined between the flexible elongated element and a proximal end of the distal tip. The maximum height of the aperture may be between a height of the proximal end of the tissue anchor and a height of the proximal end of the body plus a thickness of a soft tissue. The soft tissue may be proximal to the proximal end of the body. A maximum width of the aperture in a non-deflected state may be defined between the first and second spaced-apart locations, and the maximum width of the aperture may be approximately the maximum width of the passage. The maximum width of the aperture may extend perpendicular to the longitudinal axis of the passage. A most proximal extent of the flexible elongated element in a non-deflected state may be recessed distally within the passage from the proximal opening up to approximately a thickness of a suture mass to be passed through the aperture. The proximal opening may be configured to interface with an insertion tool. The flexible elongated element may include a suture. The suture may be a braided suture formed of a material that may include polyethylene. The material may further include a thickness of between approximately 0.008" and approximately 0.045". The suture may be at least one of heat treated, coated or impregnated to at least one of stiffen or shape the suture. The flexible elongated element may include a wire or monofilament. The flexible elongated element may extend through a sheath. The flexible elongated element may extend along a U-shaped channel member. A segment of polymer or metal may extend through a lumen of the flexible elongated element. A loop may encircle a portion of the distal tip and the loop may include the flexible elongated element. The aperture may be defined between the flexible elongated element and a proximal end of the distal tip. The loop may further include a joining member joining together the first and second tails of the flexible elongated element. The joining member may be received in a distal recess of the distal tip.

In this one aspect, the tissue anchor may be a result of an assembly process. The assembly process may include: a) assembling a tip assembly by causing a loop to encircle a portion of the distal tip; and b) causing the tip assembly to be received in the distal opening of the body. The loop may include the flexible elongated element. The loop may further include a joining member joining together the first and second tails of the flexible elongated element, and the joining member may be received in a distal recess of the distal tip as part of assembling the tip assembly.

In this one aspect, the body may further include a thread helically extending about an exterior of the body. The thread may include a double helix thread; the double helix thread may include two distinct threads offset approximately 180 degrees from each other. The aperture may have a minimum width to height ratio of three to one and a maximum width to height ratio of one to ten. The flexible elongated element may be configured to flex in a twisting rotation manner such that the aperture can accommodate different suture exchange attack angles. The flexible elongated element may be configured to flex in a twisting rotation manner such that a direction in which the aperture opens when the flexible elongated element is at maximum twisted rotation may be between approximately 90 degrees and approximately 360 degrees from the direction in which the aperture opens when the flexible elongated element is in a non-deflected state. The flexible elongated element may be configured to maintain the aperture sufficiently open to accommodate suture exchange despite being at the maximum twisted rotation. The flexible elongated element may be configured to flex in a twisting rotation manner such that the aperture has no angles that are tighter than approximately 90 degrees when the flexible elongated element is at a twisted rotation of up to approximately 90 degrees from the direction in which the aperture opens when the flexible elongated element is in a non-deflected state. The aperture may be configured to accommodate a minimum mass throughput of 4 sutures.

In another aspect, a surgical kit is provided that may include: the tissue anchor described herein, a suture, and instructions. The body of the tissue anchor may further include a distal tip that may be at least one of received or configured to be received in the distal opening. The flexible elongated element may include a first tail and a second tail spaced-apart from the first tail by the first tail and the second tail respectively intersecting the distal tip at the first and second spaced-apart locations thereby facilitating the aperture being maintained in the open condition. The suture may include a first end and a second end opposite the first end. The instructions may provide that, with the suture first extending through the aperture, the distal tip may be caused to be received in the distal opening such that the suture may extend through the passage and out the proximal opening such that the first and second ends of the suture are proximal the proximal opening. The suture may further include a loop at least one of the first end or the second end of the suture. The loop may be the result of a bifurcation of the suture or the loop may be a result of the suture being folded back on itself and adhered to itself.

In this other aspect, the surgical kit may further include a delivery device. The delivery device may include a distal end, a proximal end opposite the distal end, and a lumen extending between the distal and proximal ends of the delivery device. The distal end of the delivery device may include a feature for coupling with and transmitting a torque to the proximal end of the body. The instructions may further provide that, once the distal tip is received in the distal opening such that the suture extends through the passage and out the proximal opening such that the first and second ends of the suture are proximal the proximal opening, the suture may be further caused to extend through the lumen such that the first and second ends of the suture extend from the proximal end of the delivery device and the distal end of the delivery device may be engaged with the proximal end of the body. The instructions may be provided via at least one of: on packaging enclosing at least some of the surgical kit; in packaging enclosing at least some of the surgical kit; accompanying the surgical kit; an electronic communication; or an internet website.

In another additional aspect, a method of anchoring soft tissue to bone via a first tissue anchor including a body including a proximal opening, a distal opening, a passage extending between the proximal and distal openings, and a distal tip configured to be received in the distal opening is provided. The distal tip may be loaded with a first suture such that the first suture extends through an aperture of the distal tip. In this other additional aspect, the method may include: causing the distal tip loaded with the first suture to be received in the distal opening of the body such that the first suture extends through the passage of the body and out the proximal opening such that the first and second ends of the first suture are proximal the proximal opening. Once the distal tip is received in the distal opening such that the first suture extends through the passage and out the proximal opening such that the first and second ends of the first suture are proximal the proximal opening, the first suture may be further caused to extend through a lumen of a delivery device such that the first and second ends of the first suture extend from a proximal end of the delivery device and a distal end of the delivery device is engaged with a proximal end of the body. The lumen may extend between a distal end of the delivery device and the proximal end of the delivery device. The method may further include using the delivery device to torque the first tissue anchor into the bone. The method may further include implanting the first tissue anchor into the bone with the suture loaded distal tip received in the distal opening. The method may further include: a) extending the first and second ends of the first suture through the soft tissue; b) after step a), causing a second suture to extend through a loop defined in the first suture near the first end of the first suture or between the first and second ends of the first suture; and c) after step b), pulling on the second end of the first suture to draw the second suture through the soft tissue and down into the implanted first tissue anchor and through the aperture such that the second suture extends through the passage of the body and out the proximal opening such that first and second ends of the second suture are proximal the proximal opening and extend through the soft tissue. The second suture may extend through the soft tissue from a second tissue anchor implanted in the bone prior to being caused to pass again through the soft tissue at another location and down into the first tissue anchor as recited in step c). The second suture at the completion of step c) may extend from the first end of the second suture through the soft tissue, into and out of the implanted second tissue anchor, through the soft tissue, back into the soft tissue, into and out of the implanted first tissue anchor, and through the soft tissue to the second end of the second suture. The method may further include: a) causing a second suture to extend through a loop defined in the first suture near the first end of the first suture or between the first and second ends of the first suture; b) after step a), pulling on the second end of the first suture to draw the second suture down into the implanted first tissue anchor and through the aperture such that the second suture extends through the passage of the body and out the proximal opening such that first and second ends of the second suture are proximal the proximal opening; and c) after step b) extending the first and second ends of the second suture through the soft tissue. The second suture may extend from a second tissue anchor implanted in the bone prior to being caused to pass down into the first tissue anchor as recited in step b). The second suture at the completion of step c) may extend from the first end of the second suture through the soft tissue, into and out of the implanted second tissue anchor, through the soft tissue, back into the soft tissue, into and out of the implanted first tissue anchor, and through the soft tissue to the second end of the second suture.

While multiple embodiments are disclosed, still other embodiments of the present disclosure will become apparent to those skilled in the art from the following detailed description, which shows and describes illustrative embodiments of the disclosure. As will be realized, the invention is capable of modifications in various aspects, all without departing from the spirit and scope of the present disclosure. Accordingly, the drawings and detailed description are to be regarded as illustrative in nature and not restrictive.

BRIEF DESCRIPTION OF THE FIGURES

The following figures describe various aspects of the disclosure.

FIG. 7 is an exploded view of a tissue anchor device.

FIG. 8 is a cross-sectional side view of a tissue anchor device.

FIG. 12 is a side view of a distal end and a twisted exchange ring of a suture exchange fitting.

FIG. 13 is a top view of a distal end and a twisted exchange ring of a suture exchange fitting.

FIG. 14 is a side view of a distal end and a suture exchange fitting with a short exchange ring.

FIG. 15 is a side view of a distal end and a suture exchange fitting with a long exchange ring.

FIG. 46A, FIG. 46B, FIG. 46C, FIG. 46D, FIG. 46E, FIG. 46F, and FIG. 46G are schematic diagrams illustrating a transosseous double row repair using at least one double-loaded tissue anchor device.

FIG. 47A and FIG. 47B are schematic diagrams illustrating knotless fixation methods for double-row repairs using at least one single-loaded or double-loaded tissue anchor device.

FIG. 50A, FIG. 50B and FIG. 50C are cutaway views of a tissue anchor device that includes a free-swiveling exchange ring.

Corresponding reference characters and labels indicate corresponding elements among the views of the drawings. The headings used in the figures should not be interpreted to limit the scope of the claims.

DETAILED DESCRIPTION

In various aspects, a suture anchor device is provided herein for the attachment of soft tissues to bone. The suture anchor device may include a body which is inserted into bone tissue. The suture anchor device may further include a suture exchange fitting situated within a passage formed in the body. The suture exchange fitting may enable one or more repair sutures to be shuttled or exchanged through the suture anchor device after the body has been implanted in bone. The sutures may be looped at one or both ends; each loop may reversibly trap an end of a second suture, and the loop may pull the second suture through a suture exchange fitting and/or a soft tissue during a suture exchange. The suture exchange fitting may be further configured to collapse if subjected to a sufficiently high suture pulling force, thereby locking in any sutures present within the suture exchange fitting.

In various other aspects, a surgical kit is provided herein that may include the suture anchor device, instructions for the use of the suture anchor device, and an insertion tool or implanting the suture anchor device in the bone tissue of a subject. In other additional aspects, a method of anchoring a soft tissue to a bone using one or more tissue anchors is provided herein.

I. Tissue Anchor

One embodiment disclosed herein includes a tissue anchor that may be inserted into bone tissue to which a soft tissue is to be attached using one or more sutures in a variety of suture patterns and/or arrangements. In various aspects, the tissue anchor may include one or more suture loading features to enable the loading of one or more sutures into the tissue anchor device after deployment of the tissue anchor into the bone tissue. These one or more suture loading features may further enable the exchange of sutures between one or more additional tissue anchor deployed at other locations within the bone tissue. The one or more tissue anchors may provide robust anchor points for the secure attachment of an overlying soft tissue including, but not limited to, a tendon or ligament to the underlying bone tissue. In various other aspects, additional features of the tissue anchor as disclosed herein may facilitate suture exchange by reducing pull-through forces, may inhibit anchor pullout, and/or may reduce the likelihood of suture failure due to suture breakage, knot failure, and the like.

Figure 1:
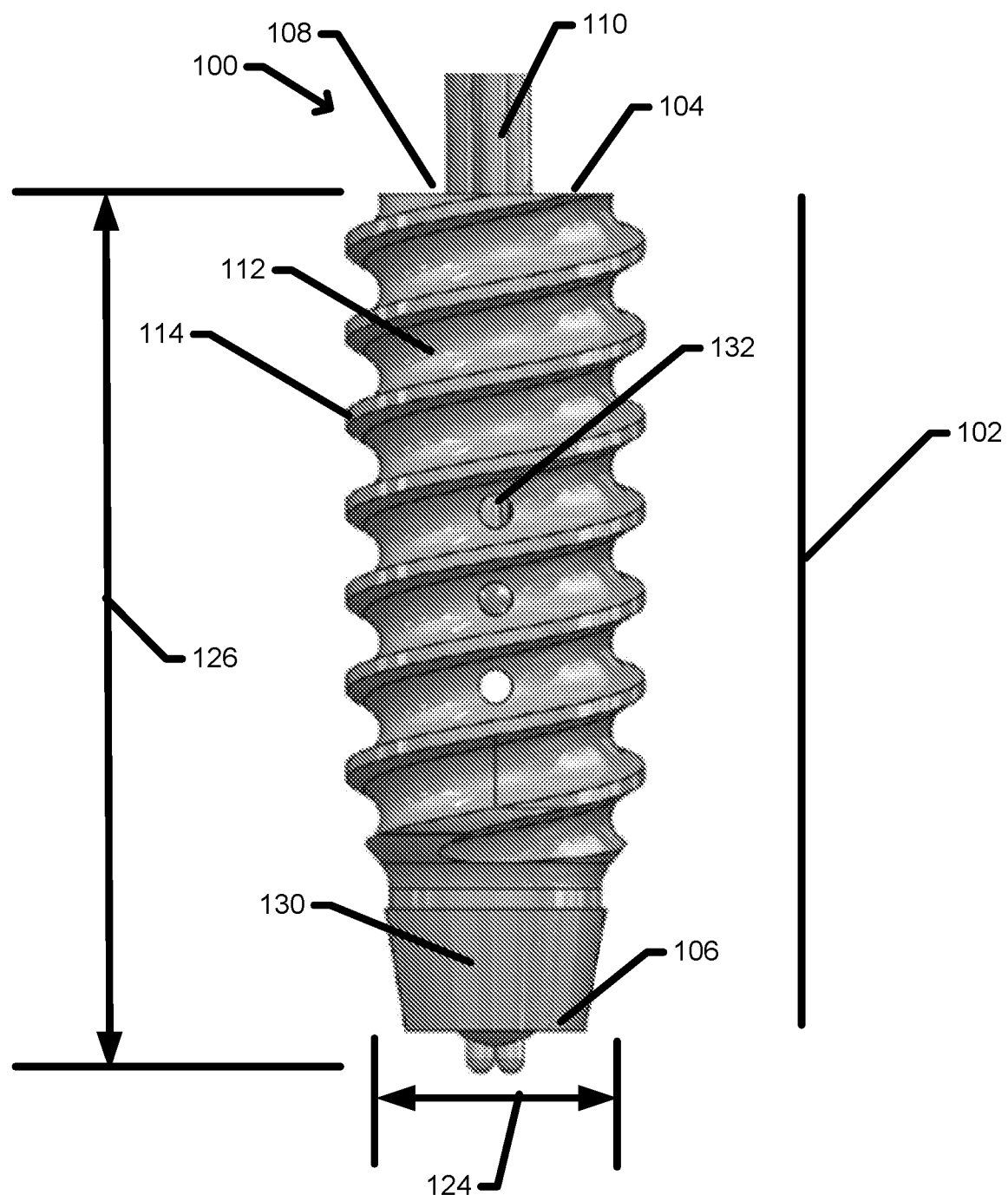
FIG. 1 is a side view of a tissue anchor device.

FIG. 1 is a side view of a tissue anchor 100 in an aspect. The tissue anchor 100 may include a body 102 with a proximal end 104 and a distal end 106 opposite to the proximal end 104. The proximal end 104 may include a proximal opening 108 configured to receive one or more sutures 110. In use, the distal end 106 of the tissue anchor 100 may be advanced into a bone tissue (not shown) using an insertion tool (not shown) reversibly attached at the proximal end 104 of the tissue anchor 100. In an aspect, the outer surface 112 of the tissue anchor 100 may include an external thread 114 to facilitate the insertion of the tissue anchor 100 into the bone tissue.

Figure 2:
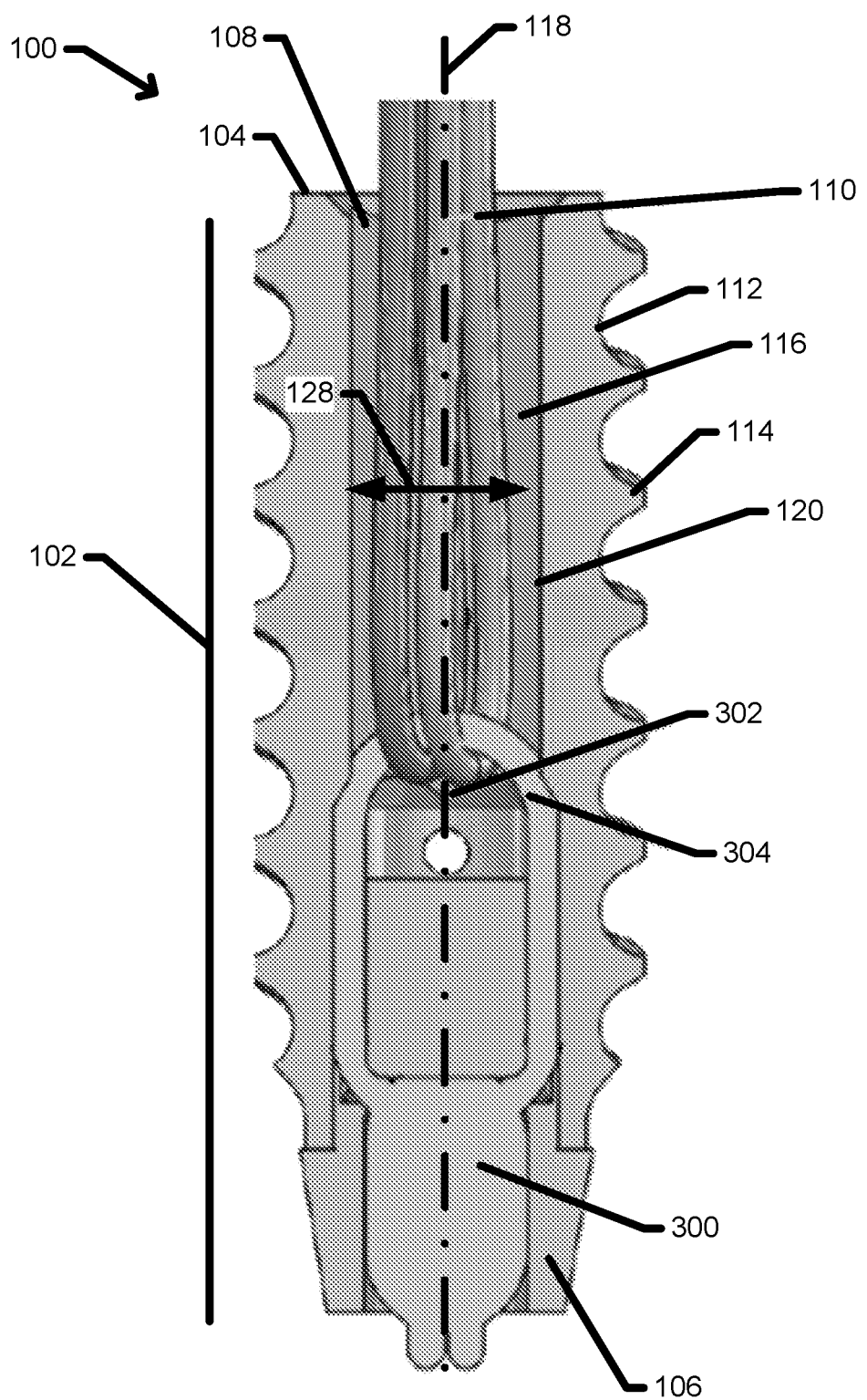
FIG. 2 is a cross-sectional side view of a tissue anchor device.

FIG. 2 is a longitudinal cross-section of the tissue anchor 100 in an aspect. The one or more sutures 110 may be retained within a passage 116 extending from the proximal opening 108 toward the distal end 106 along a longitudinal axis 118 of the passage 116. Each suture 110 may pass through an aperture 302 within a suture exchange fitting 300 situated within the passage 116. In an aspect, the suture exchange fitting 300 may be recessed distally within the passage 116 relative to the proximal opening 108. In another aspect, the passage 116 and aperture 302 may be sized to permit a sliding motion of the one or more sutures 110 through the suture exchange fitting 300 to enable the exchange of suture in and out of the tissue anchor 100 and between two or more tissue anchor 100 using a sufficiently low pulling force as described herein below.

The tissue anchor device 100, including various features of the body 102 and suture exchange fitting 300 are described in detail herein below.

a. Body

Referring again to FIG. 1, the tissue anchor device 100 includes a body 102 with a proximal end 104 and a distal end 106. In various aspects, the body 102 may be inserted into bone tissue to provide a robust anchor for one or more sutures used to attach a soft tissue including, but not limited to, a tendon or ligament to the bone tissue. As such, the external shape of the body 102 may be an elongated cylindrical profile similar to the external profile of known orthopedic fasteners including, but not limited to, bone screws.

In various aspects, the body 102 may have an outer diameter 124 ranging from about 2 mm to about 8 mm. The outer diameter 124 of the body 102 may depend on any one or more factors including, but not limited to: the accessible area of bone tissue within which the tissue anchor device 100 is to be inserted, the desired anchoring strength of the tissue anchor device 100, and the size and number of sutures to be anchored by the tissue anchor device 100. Larger outer diameters 124 may be selected for applications requiring higher anchoring strength. Further, larger outer diameters 124 may be selected for anchoring large diameter sutures and/or multiple sutures. In various other aspects, the outer diameter 124 may range from about 2 mm to about 2.2 mm, from about 2.1 mm to about 2.3 mm, from about 2.2 mm to about 2.4 mm, from about 2.3 mm to about 2.5 mm, from about 2.4 mm to about 2.6 mm, from about 2.5 mm to about 2.7 mm, from about 2.6 mm to about 2.8 mm, from about 2.7 mm to about 2.9 mm, from about 2.8 mm to about 3.0 mm, from about 2.9 mm to about 3.1 mm, from about 3.0 mm to about 3.2 mm, from about 3.1 mm to about 3.3 mm, from about 3.2 mm to about 3.4 mm, from about 3.3 mm to about 3.5 mm, from about 3.4 mm to about 3.8 mm, from about 3.6 mm to about 4.0 mm, from about 3.8 mm to about 4.2 mm, from about 4 mm to about 4.4 mm, from about 4.2 mm to about 4.6 mm, from about 4.4 mm to about 4.8 mm, from about 4.6 mm to about 5.0 mm, from about 4.8 mm to about 5.25 mm, from about 5.0 mm to about 5.5 mm, from about 5.25 mm to about 5.75 mm, from about 5.5 mm to about 6.0 mm, from about 5.75 mm to about 6.25 mm, from about 6.0 mm to about 6.5 mm, from about 6.25 mm to about 6.75 mm, from about 6.5 mm to about 7.0 mm, from about 6.75 mm to about 7.25 mm, from about 7 mm to about 7.5 mm, from about 7.25 mm to about 7.75 mm, or from about 7.5 mm to about 8 mm.

In various other aspects, the body 102 may have a length 126 ranging from about 5 mm to about 50 mm. The length 126 may vary in proportion to the outer diameter of the body 102. In various aspects, the ratio of the length 126 to the outer diameter 124 of the body 102 may be 0.5:1, 1:1, 1.5:1, 2:1, 2.5:1, 3:1, 3.5:1, 4:1, 4.5:1, 5:1, 6:1, 8:1, or 10:1. In various additional aspects, the length 126 of the body 102 may range from about 5 mm to about 10 mm, from about 7.5 mm to about 12.5 mm, from about 10 mm to about 15 mm, from about 12.5 mm to about 17.5 mm, from about 15 mm to about 20 mm, from about 17.5 mm to about 22.5 mm, from about 20 mm to about 30 mm, from about 25 mm to about 35 mm, from about 30 mm to about 40 mm, from about 35 mm to about 45 mm, and from about 40 mm to about 50 mm.

1. External Threads

Referring again to FIG. 1, the body 102 may further include at least one external feature to facilitate the implantation of the tissue anchor device 100 into the bone tissue, and to enhance the anchor strength of the tissue anchor device 100 during long-term use. Any known external feature suitable for orthopedic anchor devices may be formed on the body 102 including, but not limited to: one or more circumferential rings typical of push-in suture anchors, and one or more threads 114 helically extending about an exterior of the body 102 as illustrated in FIG. 1. In one aspect, the external feature may be one or more threads 114 extending along at least a portion of the length 126 of the body 102. The one or more threads 114 may have any configuration suitable for use in an orthopedic anchoring device including, but not limited to: single threads with a constant thread pitch, single threads with a variable pitch, self-tapping threads, and double-helix threads.

Figure 3:
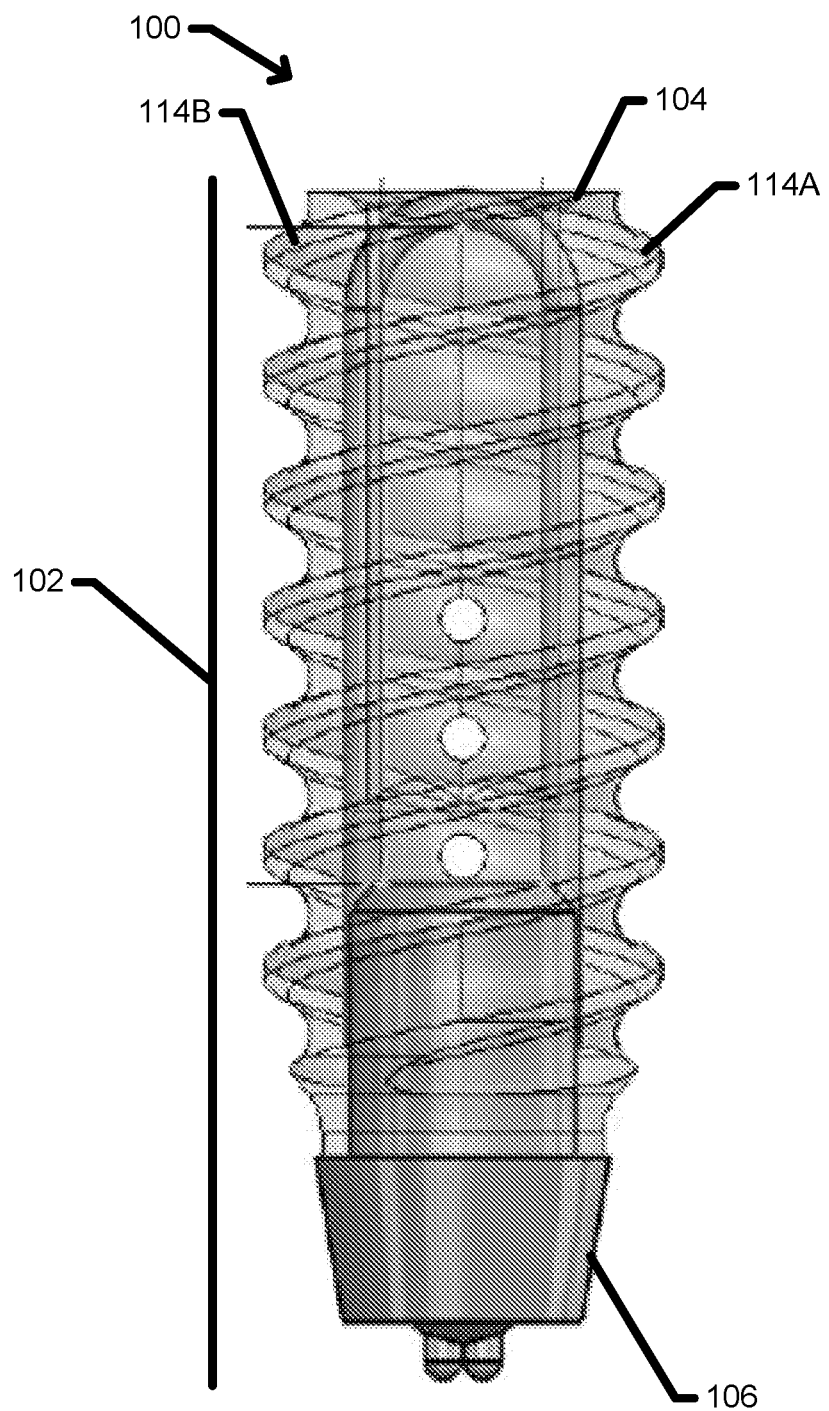
FIG. 3 is a transparent side view of a tissue anchor device.

FIG. 3 is a transparent side view of a tissue anchor device 100 with a double helix thread in one aspect. As illustrated in FIG. 3, the double helix thread includes a first thread 114A and a second thread 114B; both threads 114A/114B may start at the proximal end 104 oriented about 180° from one another. In this aspect, the double helix threads 114A/14B may enable a relatively high thread density, which may enhance bone fixation of the tissue anchor device 100, while maintaining a relatively high thread pitch, which may reduce the number of turns associated with driving the tissue anchor device 100 into the bone tissue. Compared to a double helix thread, a single helix thread may have a lower thread pitch to enable an equivalent thread density, and as a result may drive the tissue anchor device 100 into the bone tissue with a higher number of turns during implantation.

2. Distal End

Referring again to FIG. 1, the distal end 106 of the body 102 may be configured to facilitate the implantation of the tissue anchor device 100. Referring again to FIG. 2, the distal end 106 of the body 102 may further include a lead-in 130 in one aspect. The lead-in 130 may be tapered at the distal end 106 and may further be non-threaded. The profile of the lead-in 130 may be any suitable profile including, but not limited to: a conical profile, a spherical profile, a pointed profile, and any other suitable profile.

Figure 5:
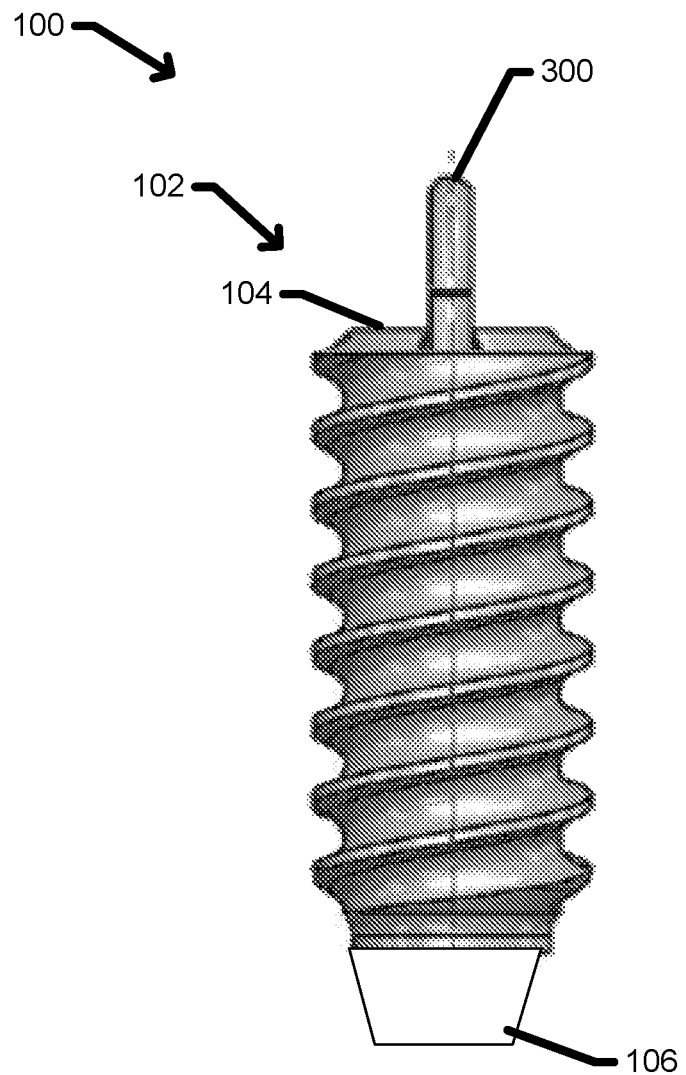
FIG. 5 is a side view of a tissue anchor device with a suture exchange fitting at the proximal end of the body.

In one aspect, the body 102 may be a solid body with no internal passage, lumen, or the like. In this aspect, a suture exchange fitting 300 may be formed in other configurations, such as an eyelet formed in the solid body 102 for receiving multiple thicknesses or strands of a suture. In this aspect, the body 102 may include a suture exchange fitting 300 attached to the proximal end 104 of the body 102, as illustrated in FIG. 5. In other aspects, the suture exchange fitting 300 may be attached at any other location on the solid body 102 without limitation. In yet other aspects, the suture exchange fitting 300 may include one or more bores (not shown) formed through the solid body 102 at any location on the body 102 without limitation.

3. Interior Passage

In another aspect, illustrated in FIG. 2, the body 102 may further include an interior passage 116 extending from the proximal opening 108 toward the distal end 106 for at least a portion of the length 126 of the body 102. In various aspects, the passage 116 may have an inner diameter 128 ranging from about 1 mm to about 6 mm. The inner diameter 128 may be selected to maintain a minimum material thickness throughout the body 102 to maintain the structural integrity of the tissue anchor device 100 during implantation and long-term use. In addition, the inner diameter may further be selected to provide sufficient space to exchange one or more sutures 110 with suitably low pulling resistance and/or to maintain a sufficiently large aperture 302 of the suture exchange fitting 300 for suture exchange.

In various aspects, the ratio of the inner diameter 128 to the outer diameter 124 of the body 102 may be about 1:10, about 1:9, about 1:8, about 1:7, about 1:6, about 1:5, about 1:4, about 1:3, about 1:2, about 1:1.5, and about 1:1.2. In various aspects, the passage 116 may have an inner diameter 128 ranging from about 1 mm to about 2 mm, from about 1.5 mm to about 2.5 mm, from about 2 mm to about 3 mm, from about 2.5 mm to about 3.5 mm, from about 3 mm to about 4 mm, from about 3.5 mm to about 4.5 mm, from about 4 mm to about 5 mm, from about 4.5 mm to about 5.5 mm, and from about 5 mm to about 6 mm.

In an aspect, the inner diameter 128 of the passage 116 may be sufficiently large to accommodate the width and the minimum mass width of the sutures 110 loaded into the tissue anchor device 100. The minimum mass width of the sutures 110, as used herein, refers to the width of double the number of sutures present in the tissue anchor device 100, and allows for the additional widths of any sutures that may be exchanged from an additional tissue anchor device 100. By way of non-limiting example, the mass width of the sutures 110 for a triple loaded tissue anchor device 100 may be 3 sutures 110, each looped through the aperture 302, for a total suture mass equal to the collective width of six sutures 110. An exchanged suture would result in an additional suture 110 being exchanged or pulled through the aperture 302, and this exchanged suture 110 may also fold over or otherwise represent a mass of double its single strand width during the suture exchange.

As described in detail herein below, the suture exchange may involve a pull of a first suture that is threaded through the aperture 302 and may further involve linking to a second suture that is also threaded through the aperture 302; the first and second suture may each contribute two ends that extend proximally from the aperture 302 through the passage 116, resulting in four lengths of suture occupying the passage 116 during a suture exchange, because each of the sutures is folded within the body 102 of the tissue anchor device 100. In various other aspects, the inner diameter 128 of the body 102 may be sufficiently large to accommodate the width and the minimum mass width of one (single loaded) #2 suture, 2 (double loaded) #2 sutures, or three (triple loaded) #2 sutures, combined with the added width of an exchanged #2 suture from a nearby anchor. In all cases, the minimum width must accommodate the loaded width and exchange width equal to twice the individual width of a #2 suture.

In various aspects, the inner diameter 128 of the passage 116 may be sized to reduce the pulling friction as one or more sutures 110 are pulled through the aperture 302 within the passage 116. In other aspects, the passage may further include additional features to reduce pulling friction. In one aspect, the passage 116 may be configured to avoid the inclusion of potential pinch points and/or friction points that may impede suture exchange, catch a suture during a suture exchange, and/or otherwise reduce suture exchange efficiency. In one non-limiting example, illustrated in FIG. 2, the inner wall 120 defining the passage 116 may be formed as a continuously smooth surface with no abrupt transitions between regions of the passage 116 that may result in sharp edges against which a suture 110 may rub. In another non-limiting example, the proximal opening 108 may include a chamfer 136 to reduce the sharpness of the lip surrounding the proximal opening 108.

Referring again to FIG. 5, the suture exchange fitting 300 may protrude proximally from the proximal end 104 of the body 102 in an aspect. In this one aspect, the passage 116 need not accommodate the sliding of one or more sutures 110, because the aperture 302 is not situated within the passage 116. In this aspect, the inner diameter 128 may be reduced to less than the width and/or the minimum mass width of two or more sutures 110 within the body 102. However, this arrangement of the suture exchange fitting 300 at the proximal end 104 of the body 102 may result in contact between the aperture 302 and the soft tissue contacting the surface of the bone above the proximal end 104 of the tissue anchor device; this contact may lead to increased friction between the aperture 302 and the one or more sutures 110 during a suture exchange, and/or irritation and/or inflammation of the soft tissue that may prolong healing of the soft tissue. To reduce the contact between the aperture 302 and the soft tissue, the body 102 may be sufficiently counter-sunk into the bone tissue to situate the aperture 302 below the bone surface. However, the overlap between the bone anchor and the rigid cortical bone may be reduced by this countersinking thereby reducing the overall fixation strength of the anchor.

4. Tool Fitting and Vent Holes

Figure 4:
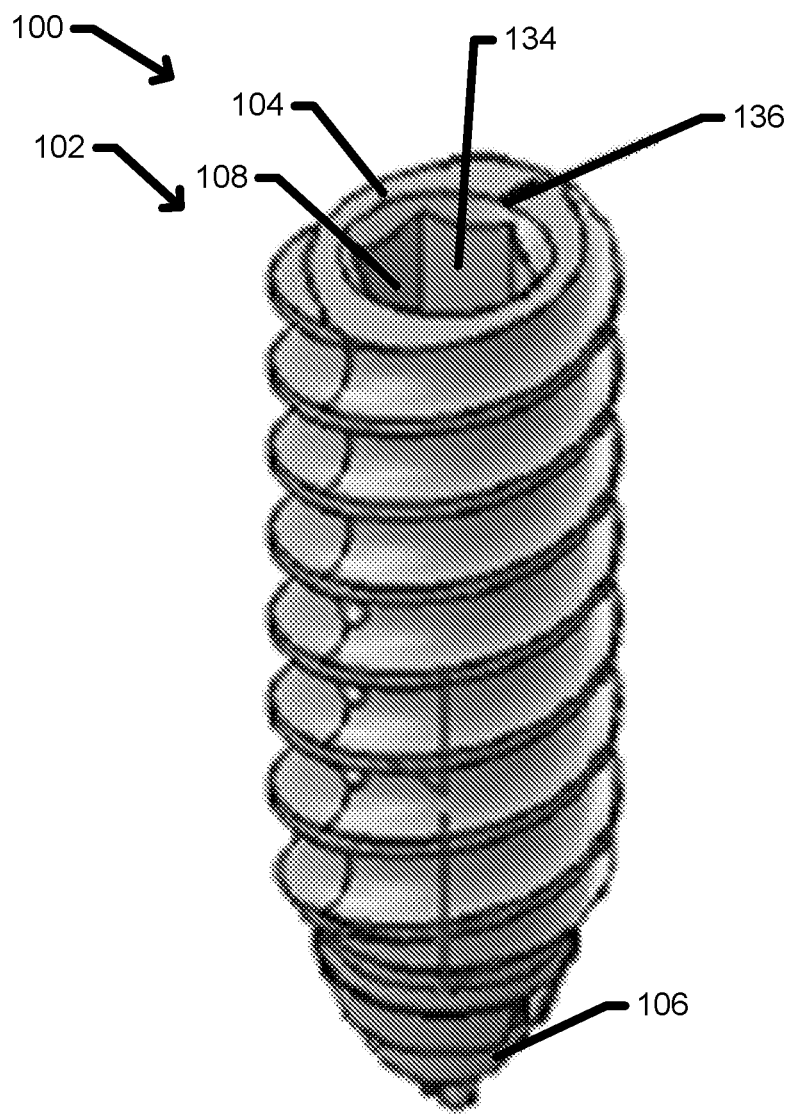
FIG. 4 is a top perspective view of a tissue anchor device.

In various aspects, the proximal end 104 of the body 102 may be configured to engage one or more tools used to implant the tissue anchor device 100 within the bone tissue. FIG. 4 is a top perspective view of a body 102 showing the proximal opening 108. In an aspect, the proximal opening may include a tool fitting 134 configured to receive a tool (not shown) used to insert the body 102 into the bone tissue. The tool fitting 134 may be configured to receive any suitable orthopedic insertion tool including, but not limited to, a torsional driver, an impact tool such as a slap hammer or impact hammer, and any other suitable tool. The tool fitting 134 may have any suitable profile corresponding to an orthopedic anchor insertion tool including, but not limited to: single-blade screwdriver, a cruciform driver, a Phillips-head screwdriver, a star-head driver, a hexagonal driver as illustrated in FIG. 4, and any other suitable tool fitting profile. In another aspect, the tool fitting 134 may include a chamfer 136 (see FIG. 4), fillet or other feature at the entry point of the tool fitting 134 to facilitate the insertion of the implantation tool into the proximal end 104 of the body 102.

Referring again to FIG. 1, the body 102 may further include additional features to enhance the healing of the bone tissue in the vicinity of the implanted tissue anchor device 100 and/or to enhance the adhesion or integration of bone tissue into the external surface of the body 102. In one aspect, the body 102 may include one or more vent holes 132 extending from the exterior surface of the body 102 into the passage 116 within the body 102. In this aspect, the one or more vent holes 132 may facilitate the migration of red blood cells and other cells and biofluids into the body 102 and may further facilitate contact of these cells and biofluids with the bottom surface of the soft tissue adjacent to the bone tissue, thereby promoting healing. In another aspect (not shown) the exterior surface of the body 102 may further include one or more depressions including, but not limited to dimples, blind bores, and/or indentations. In this other aspect, the one or more depressions may enhance the contact area of the body 102 with the surrounding bone tissue. In addition, the one or more depressions may be filled with one or more bioactive substances to promote healing of the bone tissue and overlying soft tissue. Non-limiting examples of suitable bioactive substances include: anti-inflammatory compounds, antibiotics, immunosuppressant compounds, and/or tissue growth stimulants such as bone growth factor.

In various aspects, the body 102 may be formed using any suitable biocompatible material of sufficient strength without limitation. In various aspects, any one or more known materials for orthopedic fasteners may be used to construct the body 102 including, but not limited to: metals and alloys including stainless steel, titanium, and titanium alloys, and biocompatible plastics and polymers such as PEEK. In one aspect, the body 102 may be constructed of a single material. In another aspect, the body 102 may be a composite structure composed of two or more materials.

b. Distal Tip

Figure 6:
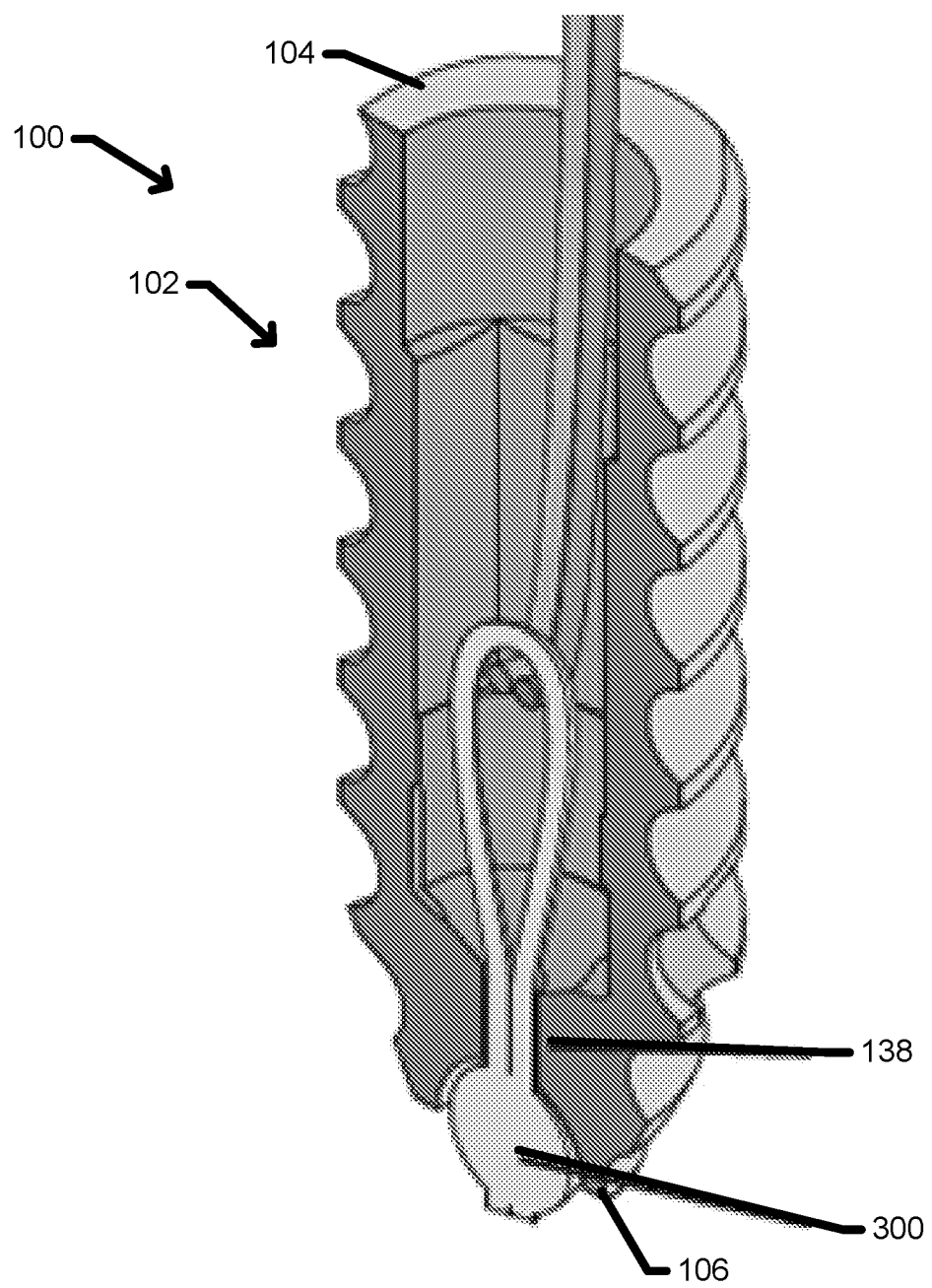
FIG. 6 is a perspective cutaway view of a single-piece tissue anchor device with a suture exchange fitting and sutures.

Referring to FIG. 6, the body 102 may be provided as a single segment extending from the proximal end 104 to the distal end 106 in one aspect. In this aspect, the distal end 106 may include a distal opening 138 through which a suture exchange fitting 300 may be inserted. In other aspects, the tissue anchor device 100 may further include a distal tip 200 in addition to the body 102. In these other aspects, the distal tip 200 may be received and/or may be configured to be received in the distal opening 138 of the body 102. The two-piece design of these other aspects may facilitate the assembly of the tissue anchor device 100.

1. Proximal Shaft

Figure 9:
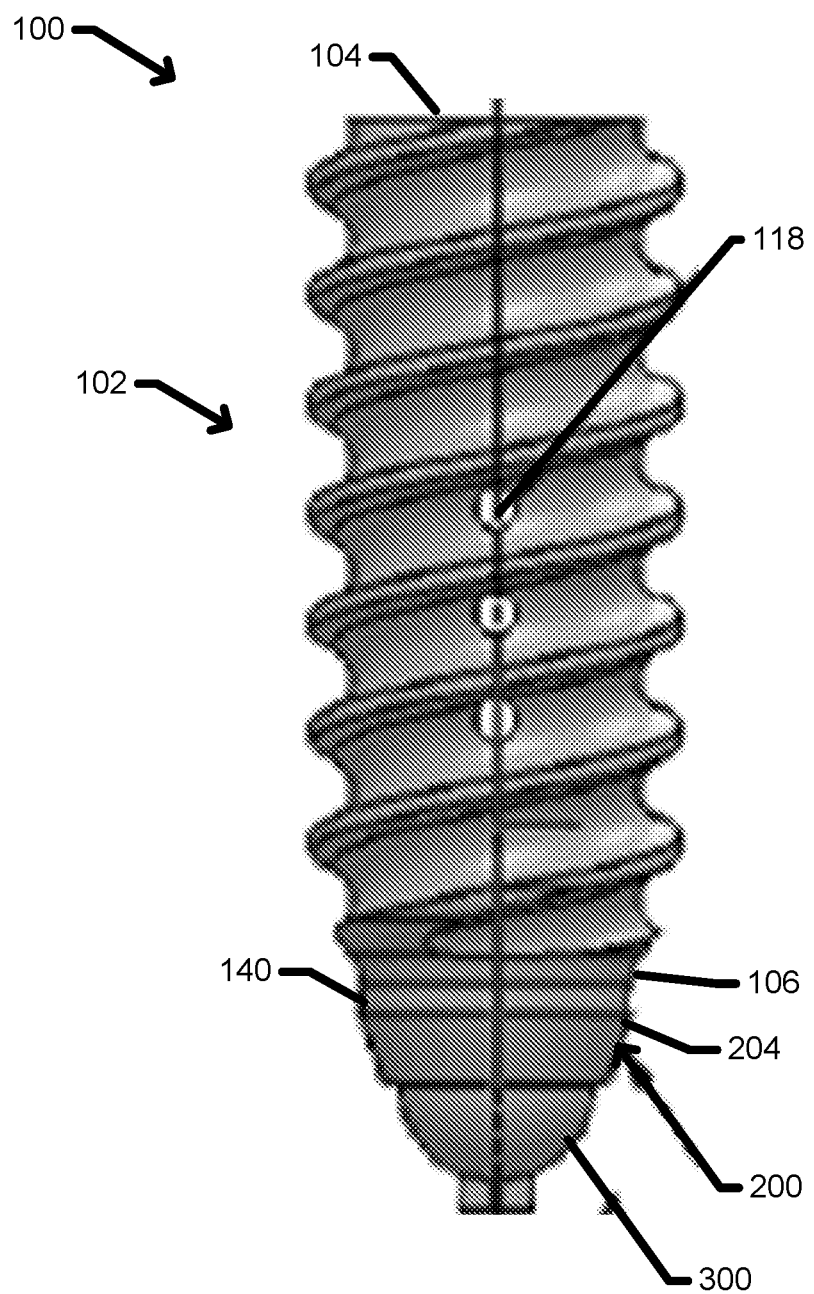
FIG. 9 is a side view of a tissue anchor device with a separate distal tip.

FIG. 7 is an exploded view of a tissue anchor device 100 that includes the body 102 and distal tip 200 in an aspect. In this aspect, the distal tip 200 may include a proximal shaft 202 protruding in a proximal direction. The proximal shaft 202 may be configured to fit within the distal opening 138 of the body. In another aspect, the distal tip 200 may further include a flange 204 with an outer diameter that is larger than the diameter of the distal opening 138, thereby providing a mechanical stop to limit the degree of insertion of the proximal shaft 202 into the distal opening 138. In this other aspect, the body 102 may be further provided with a distal face 140 against which the flange 204 of the distal tip 200 may press when the body 102 and distal tip 200 are assembled to form the tissue anchor device 100 as illustrated in FIG. 8. In this aspect, the outer diameter of the flange 204 may be essentially matched to the outer diameter of the distal end 106 of the body 102, such that the body 102 an distal end 200 form a relatively smooth profile when assembled, as illustrated in FIG. 9. In yet another aspect, the passage 116 within the body may include a step 142 which has a smaller dimension than the proximal shaft 202, within the passage 116 inside the body 102 may also serve to stop the distal tip 200 from sliding into the body 102.

Referring again to FIG. 8, the proximal shaft 202 of the distal tip 200 may be press-fit into the distal opening 138 of the body 102. Without being limited to any particular theory, the forces on the tissue anchor device 100 are typically applied in a proximal direction along the longitudinal axis 118 of the tissue anchor device 100. Loads may be applied to the distal tip 200 and may serve to further seat the proximal shaft 202 within the distal opening 138 of the body 102, thereby maintaining a secure coupling between the distal tip 200 and the body 102 without the addition of any other materials or processing. In one aspect, the coupling between the distal tip 200 and the body 102 may be a force fit or a friction fit. In other aspects, an adhesive or other biocompatible bonding agent or bonding process may be used to maintain or improve the coupling between the distal tip 200 and the body 102.

Referring again to FIG. 7, the distal tip 200 and the body 102 of the distal opening 138 may further include mechanical elements (not shown) to maintain or improve the coupling between the distal tip 200 and the body 102. Any known interlocking mechanical elements may be incorporated into the distal tip 200 and body 102 including, but not limited to, roughened surface textures, additional elements such as compression washers and the like, and interlocking mechanical elements such as meshing threads. In one aspect, the outer surface 210 of the proximal shaft 202 and receiving surface 144 of the distal opening 138 may include surface roughening (not shown). In another aspect, a compression washer or washer with a roughened texture (not shown) may be inserted over the proximal tip 202 prior to assembly of the tissue anchor device 100. In an additional aspect, the outer surface 210 of the proximal shaft 202 may include a threaded portion (not shown) that may intermesh with a threaded receptacle (not shown) formed on the receiving surface 144 of the distal opening 138; the distal tip 200 may be rotated to advance the threaded portion into the threaded receptacle of the distal opening 138. In another additional aspect, the outer surface 210 of the proximal shaft 202 may include one or more tabs or protrusions (not shown) that may intermesh with one or more tracks or slots (not shown) formed on the receiving surface 144 of the distal opening 138. In this other additional aspect, the distal tip may be advanced into the distal opening 138 with the one or more tabs or protrusions upon the outer surface 210 of the proximal shaft 202 aligned with one or more gaps (not shown) formed in the one or more tracks or slots on the receiving surface 144; the distal tip 200 may then be rotated a partial turn up to about 45 degrees to advance the tabs or protrusions of the distal tip 200 into the tracks or slots of the distal opening 138, thereby locking the distal tip 200 in place.

In various aspects, the distal tip 200 may be formed using any suitable biocompatible material of sufficient strength without limitation. In various aspects, any one or more known materials for orthopedic fasteners may be used to construct the distal tip 200 including, but not limited to: metals and alloys including stainless steel, titanium, and titanium alloys, and biocompatible plastics and polymers such as PEEK. In one aspect, the distal tip 200 may be constructed of a single material. In another aspect, the distal tip 200 may be a composite structure composed of two or more materials. In yet another aspect, the distal tip 200 and body 102 may be constructed of similar metal compositions to prevent oxidation-reduction reactions between the body 102 and distal tip 200 that may degrade one or both components over long-term use.

2. Retention Features For Suture Exchange Fitting

Referring again to FIG. 8, the distal tip 200 may further include one or more additional features to retain the suture exchange fitting 300 at a desired position and to further maintain the aperture 302 of the suture exchange fitting 300 in an open position to facilitate the exchange of sutures within the aperture 302. By way of non-limiting example, these additional features may include a distal recess 206 formed within the distal end 208 of the distal tip 200 to secure the suture exchange fitting 300 in a fixed position near the distal end 106 of the body 102. Various aspects of additional features of the distal tip 200, as well as the body 102, to retain the suture exchange fitting 300 are described in detail herein below.

c. Suture Exchange Fitting

Referring again to FIG. 2, the tissue anchor device 100 may further include a suture exchange fitting 300 with an aperture 302 in various aspects. The aperture 302 may enable repair sutures to be shuttled or exchanged through the body 102 of the tissue anchor device 100 after the tissue anchor device 100 has been implanted in bone tissue and may further enable the repair sutures to be passed through soft tissue in one aspect. In another aspect, the aperture 302 may be configured to remain fully open during each suture exchange, thereby maintaining the suture friction and associated suture pulling force at acceptably low levels. Without being limited to any particular theory, a relatively high suture friction and/or suture pulling force may degrade the effectiveness of the tissue anchor device 100 due to reduction in surgical tactile feel during suture exchange and/or an inability to execute the pull-through of sutures due to increased suture pulling forces. In another aspect, the aperture 302 of the suture exchange fitting 300 may be configured to close or collapse once the load or tension applied to the repair sutures exceed a particular threshold collapsing force, thereby preventing further suture exchanges.

During suture exchange and the initial passage of one or more repair sutures 110 through the soft tissue, the aperture 302 may maintain a space sufficiently large to allow for the passage of up to several sutures 110 through the body 102 of the tissue anchor device 100 after implantation in the bone tissue as described herein above. As described herein below, each suture 110 exchanged through an aperture 302 may be doubled over and as a result, the aperture 302 may be sized to accommodate the unimpeded passage of 2 sutures for every desired suture exchange. In one aspect, the aperture 302 may be sized to accommodate a single suture exchange, corresponding to the passage of at least two sutures 110 simultaneously. In another aspect, the aperture 302 may be sized to accommodate two suture exchanges concurrently, corresponding to the passage of at least four sutures 110 simultaneously. In an additional aspect, the aperture 302 may be sized to accommodate three or more suture exchanges concurrently, corresponding to the passage of at least six sutures 110 simultaneously.

In addition, the aperture 302 and associated suture exchange fitting 300 may be provided with sufficient strength to withstand the pulling forces that are applied by the one or more repair sutures 110, thereby maintaining the space within the aperture 302 essentially unchanged throughout the suture exchange process and fixation of a soft tissue to a bone tissue using the tissue anchor device 100. Non-limiting examples of puling forces applied by the one or more repair sutures 110 during the exchange process include: tension resulting from pulling one or more repair sutures and/or friction resulting from the sliding of the one or more sutures through the aperture 302. In another aspect, additional tension in the suture may result from pulling multiple sutures through multiple tissue layers and/or multiple tissue anchor devices 100 with multiple apertures 302 during the course of an orthopedic repair procedure as described herein below. In one aspect, the pulling force applied by the one or more repair sutures 110 during the exchange and repair process may be less than about 20 lbs. In various other aspects, the pulling force may be less than about 19 lbs., less than about 18 lbs., less than about 17 lbs., less than about 16 lbs., less than about 15 lbs., less than about 14 lbs., less than about 13 lbs., less than about 12 lbs., less than about 11 lbs., less than about 10 lbs., less than about 8 lbs., less than about 4 lbs., or less than about 2 lbs.

During a suture exchange, the direction of sliding of the one or more sutures 110 may aligned at a variety of angles relative to the initial orientation of the sutures 110 and the aperture 302. Without being limited to any particular theory, a fixed suture exchange fitting 300 that is unable to rotate may develop pinch points, suture cross-over tensions that may impede a suture exchange, and/or tortuosities that may restrict or prevent the completion of a suture exchange. In various aspects, the aperture 302 and associated suture exchange fitting 300 may be configured to rotate within a predetermined range during a suture exchange due to torsion resulting from pulling one or more repair sutures 110 in a direction offset from a plane coincident with the aperture 302. Referring again to FIG. 2, the suture exchange fitting 300 may include an exchange ring 304 defining the aperture 302 in one aspect. In this aspect, the exchange ring 304 may be configured to rotate and/or deform under torsional loads to maintain a sufficiently large aperture 302 for the suture exchange process. In another aspect, the exchange ring 304 and associated aperture 302 may consist of rounded shapes and edges to reduce the potential of binding, pinching, or otherwise impeding the sliding of one or more sutures 110 through the aperture 302 during a suture exchange. In this other aspect, the exchange ring 304 may be configured to include only internal angles of greater than about 90°. In one aspect, the exchange ring 304 may be provided in an essentially semicircular shape, as illustrated in FIG. 2.

In an aspect, the predetermined range through which the exchange ring 304 may rotate relative to an initial position of the exchange ring 304 in the absence of a torsional load may be up to about 360°. In this aspect, a rotation of the exchange ring 304 up to about 360° enables the suture exchange fitting 300 to accommodate a variety of suture loads and movements associated with a suture exchange and/or fixation of a soft tissue to an underlying bone tissue, without collapse of the aperture 302 and associated increase in pulling friction of the one or more sutures 110. Without being limited to any particular theory, it is thought that rotations of the exchange ring 304 to angles over 360° relative to the initial position of the exchange ring 304 may result in collapse of the aperture 302. In various other aspects, the predetermined range through which the exchange ring 304 may rotate relative to an initial position of the exchange ring 304 in the absence of a torsional load may be up to about 360°, up to about 340°, up to about 320°, up to about 300°, up to about 280°, up to about 260°, up to about 200°, up to about 180°; up to about 150°, up to about 120°, up to about 90°, up to about 45°, up to about 30°, and up to about 10°.

In various aspects, the exchange ring 304 may be constructed from any suitable biocompatible material including, but not limited to: a metal, a plastic, or a suture or other flexible material including a woven fabric or a braided fabric. In various other aspects, the exchange ring 304 may also be provided in the form of a bar or clip machined or formed from a metal or plastic material. In these various other aspects, the bar or clip, when taken in combination with other features or structures of the body 102 and/or distal tip 200, may define the aperture 302. In an additional aspect, the aperture 302 may be machined, molded or formed directly into the body 102 and/or distal tip 200 of the tissue anchor device 100.

In one aspect, the exchange ring 304 may be constructed from a flexible material, thereby enabling the exchange ring 304 to deform through a predefined angular range during a suture exchange and/or fixation of a soft tissue to a bone tissue using the tissue anchor device 100. In another aspect, the suture exchange fitting 300 may be provided with a rotational coupling to the body 102 and/or distal tip 200, thereby enabling the rotation of the exchange ring 304 without significant deformation under torsional loads. In yet another aspect, the exchange ring 304 may be provided with two or more rigid segments coupled together by one or more rotational couplings, thereby permitting a twisting movement of the two or more segments to accommodate torsional loads while maintaining a sufficiently large aperture 302 during a suture exchange and/or fixation of a soft tissue to a bone tissue using the tissue anchor device 100. In various other aspects, any combination of any of the features described herein above including, but not limited to the flexible material, the rotational coupling, and/or the two or more segments, may be incorporated into the suture exchange fitting 300. Detailed descriptions of the structure and function of specific suture exchange fittings 300 in various aspects are provided herein below.

Figure 10:
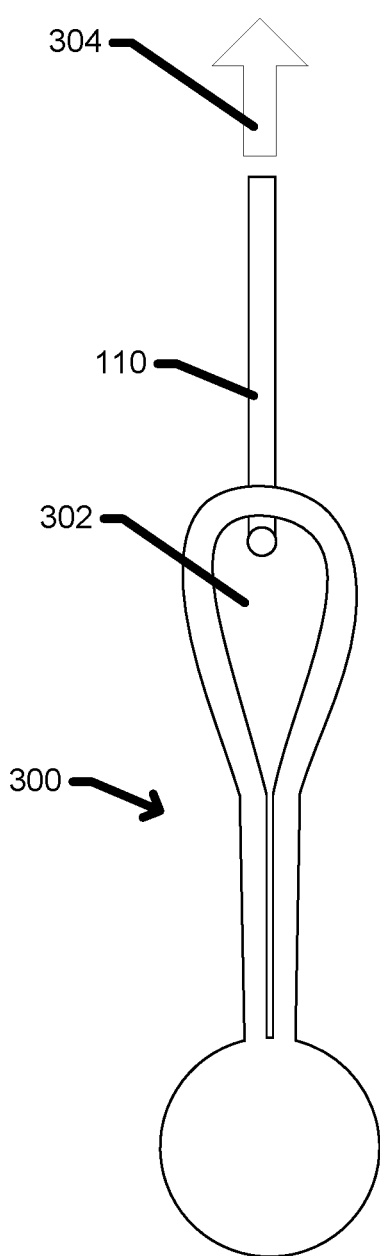
FIG. 10 is a side view of a suture exchange fitting in an opened configuration.
Figure 11:
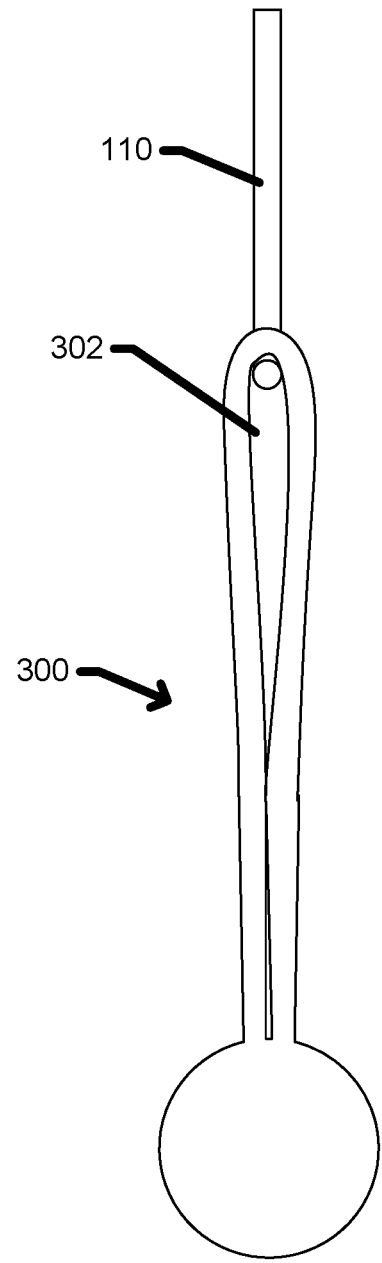
FIG. 11 is a side view of a suture exchange fitting in a collapsed configuration.

In various aspects, the aperture 302 of the suture exchange fitting 300 may be configured to collapse, thereby essentially fixing the one or more sutures 110 in place within the tissue anchor device 100 and creating a more secure tissue fixation structure. FIG. 10 and FIG. 11 are side views of a suture exchange fitting 300 with the aperture 302 in an open (FIG. 10) and collapsed (FIG. 11) configuration in an aspect. Referring to FIG. 10, once the suture exchange and the initial passage of one or more repair sutures 110 through the soft tissue is completed, a collapsing force 306 may be applied to the one or more sutures 110. This collapsing force 306 may be sufficiently high to collapse the aperture 302 into a collapsed configuration, as illustrated in FIG. 11. In one aspect, the collapsing force 306 applied by the one or more repair sutures 110 after the exchange process may be greater than about 20 lbs. In various other aspects, the collapsing force 306 may be greater than about 22 lbs., the collapsing force 306 may be greater than about 24 lbs., the collapsing force 306 may be greater than about 26 lbs., the collapsing force 306 may be greater than about 28 lbs., the collapsing force 306 may be greater than about 30 lbs., the collapsing force 306 may be greater than about 35 lbs., the collapsing force 306 may be greater than about 40 lbs., the collapsing force 306 may be greater than about 45 lbs., the collapsing force 306 may be greater than about 50 lbs., the collapsing force 306 may be greater than about 60 lbs., the collapsing force 306 may be greater than about 70 lbs., the collapsing force 306 may be greater than about 80 lbs., or the collapsing force 306 may be greater than about 100 lbs.

1. Flexible Suture Exchange Fittings

In an aspect, at least a portion of the suture exchange fitting 300 may be a flexible elongated element constructed from a flexible material including, but not limited to, a suture material. Non-limiting examples of suture materials suitable for inclusion in a suture exchange fitting 300 include: non-absorbable suture materials such as polyethylene, polyester, and the like; absorbable suture materials such as a lactide-glycolide copolymer and the like; and any combination thereof. In one aspect, the inclusion of flexible materials in the suture exchange fitting 300 may enable the deformation of the suture exchange fitting 300 under torsional loads during suture exchange, as well as the collapse of the aperture 302 under the collapsing force 306 as described herein above.

FIG. 12 and FIG. 13 are side and top views, respectively, of a distal tip 200 with a suture exchange fitting 300 that has been deformed by a torsion resulting from the twisting of a suture 110 within the aperture 302. In this aspect, the exchange ring 304 may be constructed of a flexible material, thereby enabling the deformation of the exchange ring 304 from an initial position 304' through a twist angle 308. The exchange ring 304 may twist through a predetermined range as described herein above including, but not limited to up to about 360°. In this aspect, the predetermined range may be influenced by any one or more of at least several factors, described herein below.

In one aspect, the structural integrity of the exchange ring 304 may be sufficient to maintain the aperture 302 in an open position in the presence of any forces and torques exerted on the exchange ring 304 by one or more sutures 110 in association with a suture exchange and/or fixation of a soft tissue to a bone tissue using the tissue anchor device 100. In an aspect, the exchange ring 304 may resist deforming in response to a suture pulling force with a magnitude up to the collapsing force as described herein above. In another aspect, the exchange ring 304 may permit twisting within a predetermined angular range as described herein above in response to a torsion exerted by the one or more sutures 110 as described herein above. The structural integrity of the exchange ring 304 may be influenced by any one or more of at least several factors including, but not limited to: the properties of the material used to construct the exchange ring such as tensile strength and torsional stiffness, the dimensions of the exchange ring 304, additional support provided by the body 102 and/or distal tip 300, and the reinforcement of at least a portion of the exchange ring 304.

In an aspect, the exchange ring 304 may be formed from a single braided suture. In other aspects, at least a portion of the exchange ring 304 may be stiffened or shaped using an application of heat to adhere two or more strands of the braided suture and/or through the application of a coating to the braided suture material. In additional aspect, a coating applied to the exchange ring 304 may further reduce the friction between the exchange ring 304 and one or more sutures 110 sliding through the aperture 302 during a suture exchange or tightening of a suture during fixation of a soft tissue to a bone tissue using the tissue anchor device 100. In various other aspects, the exchange ring 304 may be constructed from other materials including, but not limited to wire, monofilaments, metals, and the like. Non-limiting examples of suitable coating materials include acrolytes, silicones; polyurethanes; polylactic acid; polyglycolic acid and other degradables; and fibrin glue. In other aspects, the coating may be applied to a portion of the exchange ring 304 or to the entire exchange ring 304 as needed.

In an aspect, the structural integrity of the exchange ring 304 may be influenced by the dimensions of the exchange ring 304. FIG. 14 is a side view of a distal tip and suture exchange fitting 300 with a relatively small aperture 302 in one aspect. FIG. 15 is a side view of a distal tip and suture exchange fitting 300 with a relatively large aperture 302 in another aspect. In both aspects, the aperture size may be quantified by one or more dimensions of the aperture 302 including, but not limited to, a maximum height 310, a maximum width 312, and an aperture area 314.

Referring again to FIG. 14 and FIG. 15, the maximum height 310 with respect to the maximum width 312 of the exchange ring 304 may influence the overall performance of the suture exchange. A relatively longer maximum height 310 (see FIG. 15) may increase the rotational flexibility of the exchange ring 304; however, excessive maximum height 310 may permit the ring exchange ring 304 to easily twist more than 360° which may effectively collapse the aperture 302, thereby hindering a suture exchange. A relatively shorter maximum height 310 (see FIG. 14) may better resist twisting and collapse and thereby better maintain an open aperture compared to a taller exchange ring 304; however, if the exchange ring 304 is too short the aperture 302 may be too small to accommodate the combined mass of all sutures 110 and may thereby hinder a suture exchange.

In various aspects, the ratio of the maximum width 312 to the maximum height of the aperture 310 may range from about 1:10 to about 3:1. In various other aspects, the ratio of the maximum width 312 to the maximum height of the aperture 310 may range from about 1:10 to about 1:8, from about 1:9 to about 1:7, from about 1:8 to about 1:6, from about 1:7 to about 1:5, from about 1:6 to about 1:4, from about 1:5 to about 1:3, from about 1:4 to about 1:2, from about 1:3 to about 1:1, from about 1:2 to about 2:1, and from about 1:1 to about 3:1.

Figure 16:
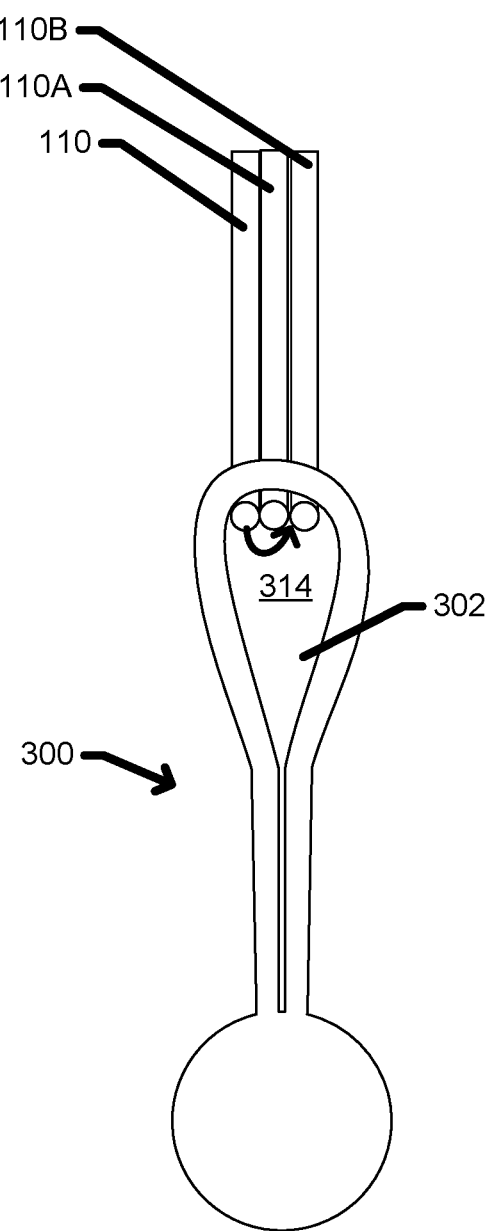
FIG. 16 is a side view of a suture exchange fitting in an opened configuration with several sutures within the exchange ring.

In an aspect, the aperture area 314 may be sufficient to accommodate a single, double, or triple suture material mass, corresponding to a single loaded, double loaded, or triple loaded tissue anchor device 100, respectively. In another aspect, the aperture area 314 may provide additional space for a first suture to shift position relative to a second suture. FIG. 16 is a side view of a triple-loaded suture exchange fitting 300 in which the aperture area 314 provides additional space for a first suture 110 to change positions relative to a second suture 110A.

i) First and Second Spaced-Apart Locations

Figure 17:
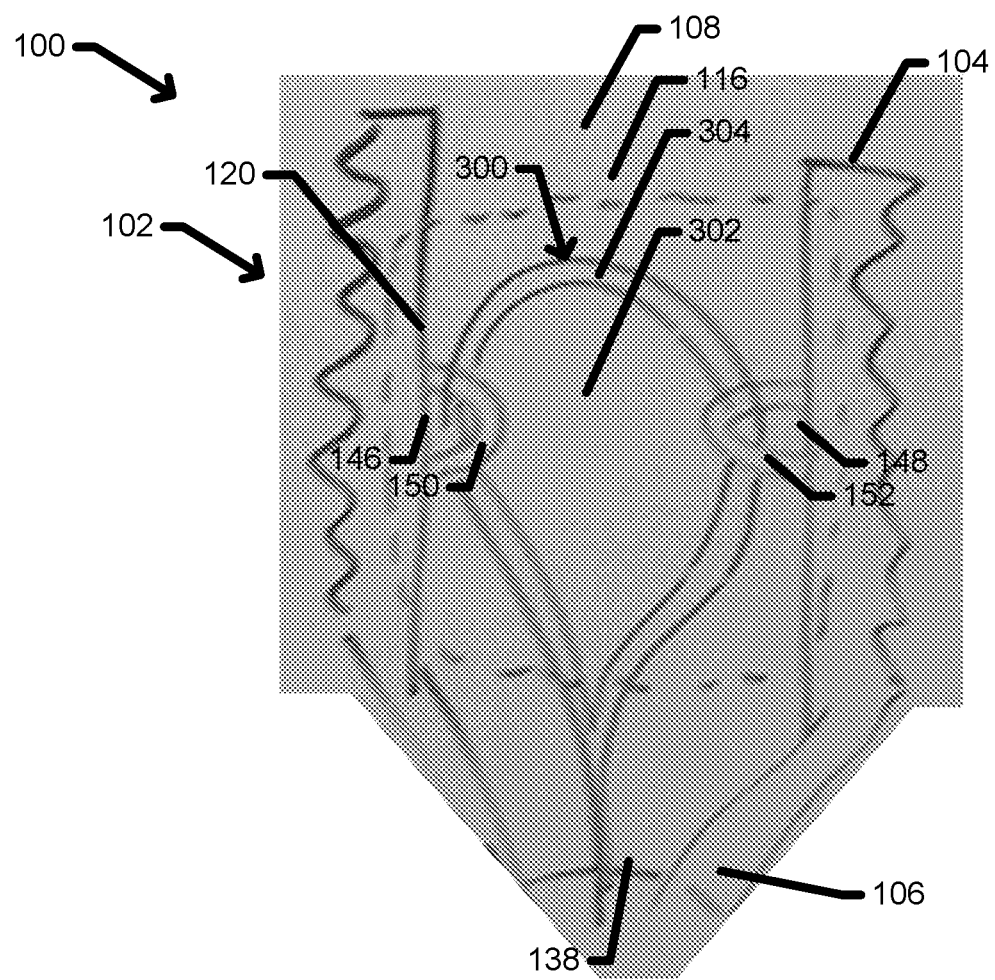
FIG. 17 is a cross-sectional side view of a tissue anchor device with support loops attached to the inner wall defining the passage.

In an aspect, the structural integrity of the suture exchange fitting 300 may be enhanced by securing at least a portion of the suture exchange fitting 300 to the body 102 and/or the distal tip 200 at a first and second spaced-apart location. In this aspect, the secured portions of the suture exchange fitting 300 may be maintained in separated positions, thereby maintaining the aperture 302 of the suture exchange fitting 300 in an open position. FIG. 17 is a side cross-sectional view of a tissue anchor device 100 in which the exchange ring 304 of the suture exchange fitting 300 is secured within the passage 116 of the body at a first spaced-apart location 146 and at a second spaced-apart location 148. The first and second spaced-apart locations 146/148 are typically positioned on opposite positions within the lumen 116 in order to maintain the aperture 302 in as wide-open a position as possible within the lumen 116.

The exchange ring 304 of the suture exchange fitting 300 may be secured within the lumen 116 of the body 102 by any known means without limitation. Referring again to FIG. 17, the inner wall 120 of the body 102 may be provided with a pair of fixation fittings 150/152 through which the exchange ring 304 may be threaded, thereby fixing the exchange ring 304 at the first and second spaced-apart locations 146/148. Any suitable fixation fitting may be used without limitation. In one aspect, the fixation fittings 150/152 may be a mechanical fitting including, but not limited to: a ring (see FIG. 17), a hook, or a loop. In another aspect (not shown) the exchange ring 304 may be affixed to the inner wall 120 at the first and second spaced-apart locations 146/148 using a biocompatible adhesive. In yet another aspect (not shown) the exchange ring 304 may be affixed by melting the inner wall 120 and/or portions of the exchange ring 304 at the first and second spaced-apart locations 146/148. In various aspects, the fixation fittings 150/152 may be configured to release the secured portions of the exchange ring 304 when the exchange ring 304 is subjected to a collapsing force 306, to enable the collapsing of the aperture 302 once a suture exchange through the exchange ring 304 is completed.

In other aspects, at least a portion of the exchange ring 304 may be affixed at first and second spaced-apart locations 146/148 situated on the distal tip 200 at a first and second side 212/214 in order to maintain the aperture 302 in an open position. In these other aspects, the exchange ring 304 may be affixed to the distal tip 200 and then the distal tip 200 may be inserted into the distal opening 138 of the body 102. Once assembled, the exchange ring 304 is situated proximal to the distal tip 200 within the passage 116 of the body 102, as illustrated in FIG. 2.

Figure 18:
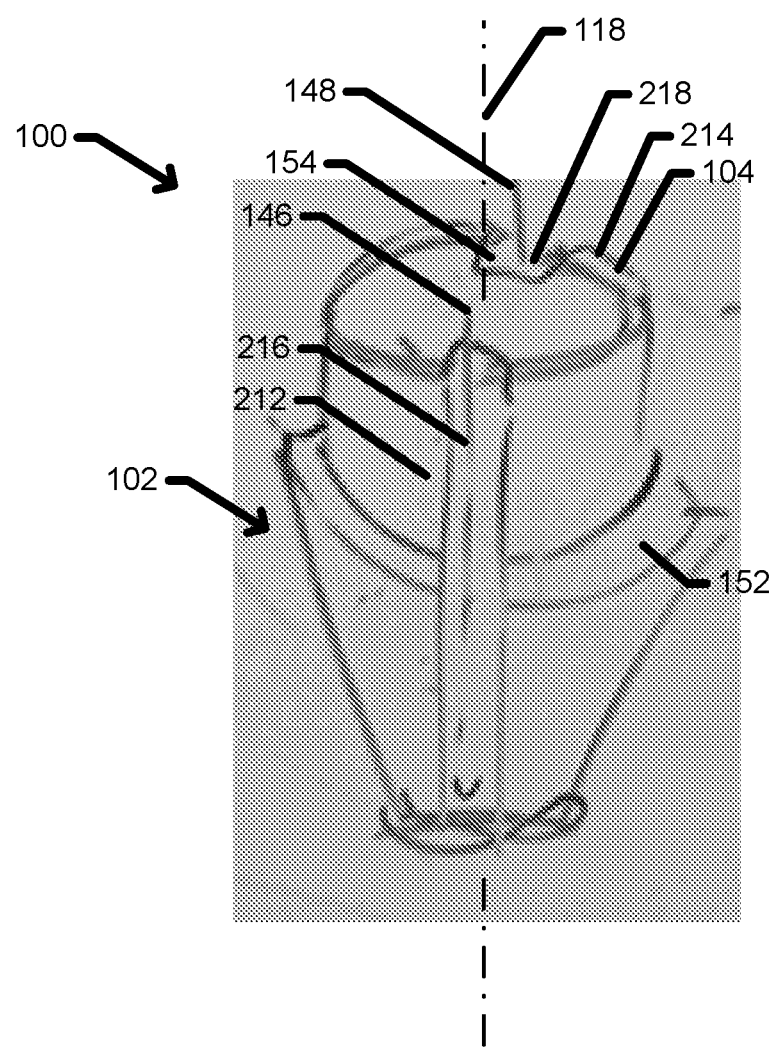
FIG. 18 is a top perspective view of a distal tip with a first channel at a first side and a second channel at a second side of the distal tip.

Referring to FIG. 18, the first and second side 212/214 of the distal tip 200 may be provided with a first and a second channel 216/218 configured to hold at least a portion of the exchange ring 304 in one aspect. The first and second channels 216/218 may be aligned with the longitudinal axis 118 of the tissue anchor device 100 in an aspect. In another aspect, the first and second channels 216/218 may extend over at least a portion of the distal tip 300.

Referring again to FIG. 7, the first and second channels 216/218 may be grooves extending the entire length of the distal tip 300. In this aspect, the exchange ring 304 of the suture exchange fitting 300 may be wrapped around the distal tip 200 with portions of the exchange ring situated within the first and second channels 216/218, as illustrated in FIG. 8; the exchange ring 304 may be wrapped around the distal tip 200 before the distal tip 200 is pressed into the body 102. Once the proximal shaft 202 is inserted into the distal opening 138 of the body 102, the portions of the exchange ring 304 are retained between the first and second channels 216/218 and the inner wall 120 of the distal opening 138. In this aspect, the distal tip 200 maintains the aperture 302 of the exchange ring 300 in an open position and prevents the aperture 302 from collapsing.

Figure 19:
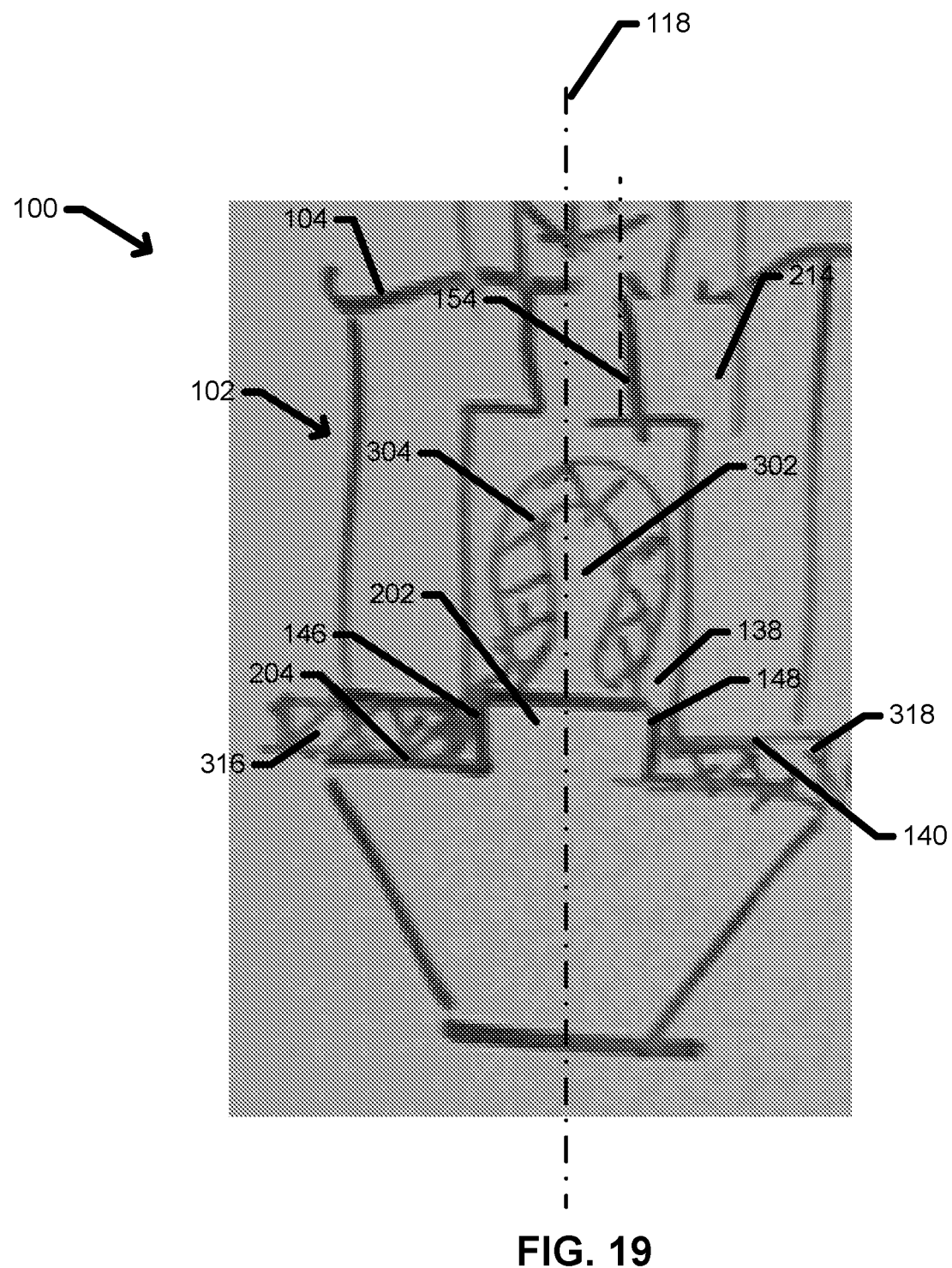
FIG. 19 is a cross-sectional side view of a tissue anchor device with an exchange ring formed from a single flexible strand with opposed ends secured between the distal end of the body and the proximal end of the distal tip.

FIG. 19 is a side cross-sectional view of an exchange ring 304 constructed from a single piece of a flexible material including, but not limited to a suture, in which the flexible material is affixed at the first and second spaced-apart locations 146/148 in an aspect. As illustrated in FIG. 19, the first and second spaced-apart locations 146/148 may correspond to different sides of the distal tip 200 as described herein previously. In this aspect, the flexible material may include a first tail 316 situated between the flange 204 of the distal tip 200 and the distal face 140 of the body 102. The flexible material may further include a second tail 318 situated between the flange 204 of the distal tip 200 and the distal face 140 of the body 102 opposite to the first tail 316. In this aspect, the first and second ends 318 may be held in place by compressive forces between the distal tip 200 and the body 102 as described herein previously. In another aspect, the flange 204 and/or the distal face 140 may include additional features (not shown) to enhance the fixation of the first and second ends 316/318 including, but not limited to: grooves or channels formed in the flange 204 and/or distal face 140, In another aspect (not illustrated), the first and second spaced-apart locations 146/148 situated on the distal tip 200 may be provided in the form of a first lumen and a second lumen formed through the distal tip 200. The first and second lumens may be aligned with the longitudinal axis 118 of the tissue anchor device 100 and may open at the proximal shaft 202 and the distal end 208 of the distal tip 200. The first and second lumens may further be situated near the outer perimeter of the distal tip 200 and located at opposite sides of the distal tip 200. In this other aspect, the exchange ring 304 may be formed from a single length of a flexible material as described herein previously, with the first tail 316 threaded through the first lumen and the second tail 318 threaded through the second lumen. The first tail and the second tail may be glued and/or melted within the first and second lumens. The first and second tails may be threaded through the first and second lumens and the distal ends of the first and second tails knotted to prevent the tails from retracting proximally through the lumens; each tail may be knotted separately, or the first and second tails may be knotted to one another.

Figure 20:
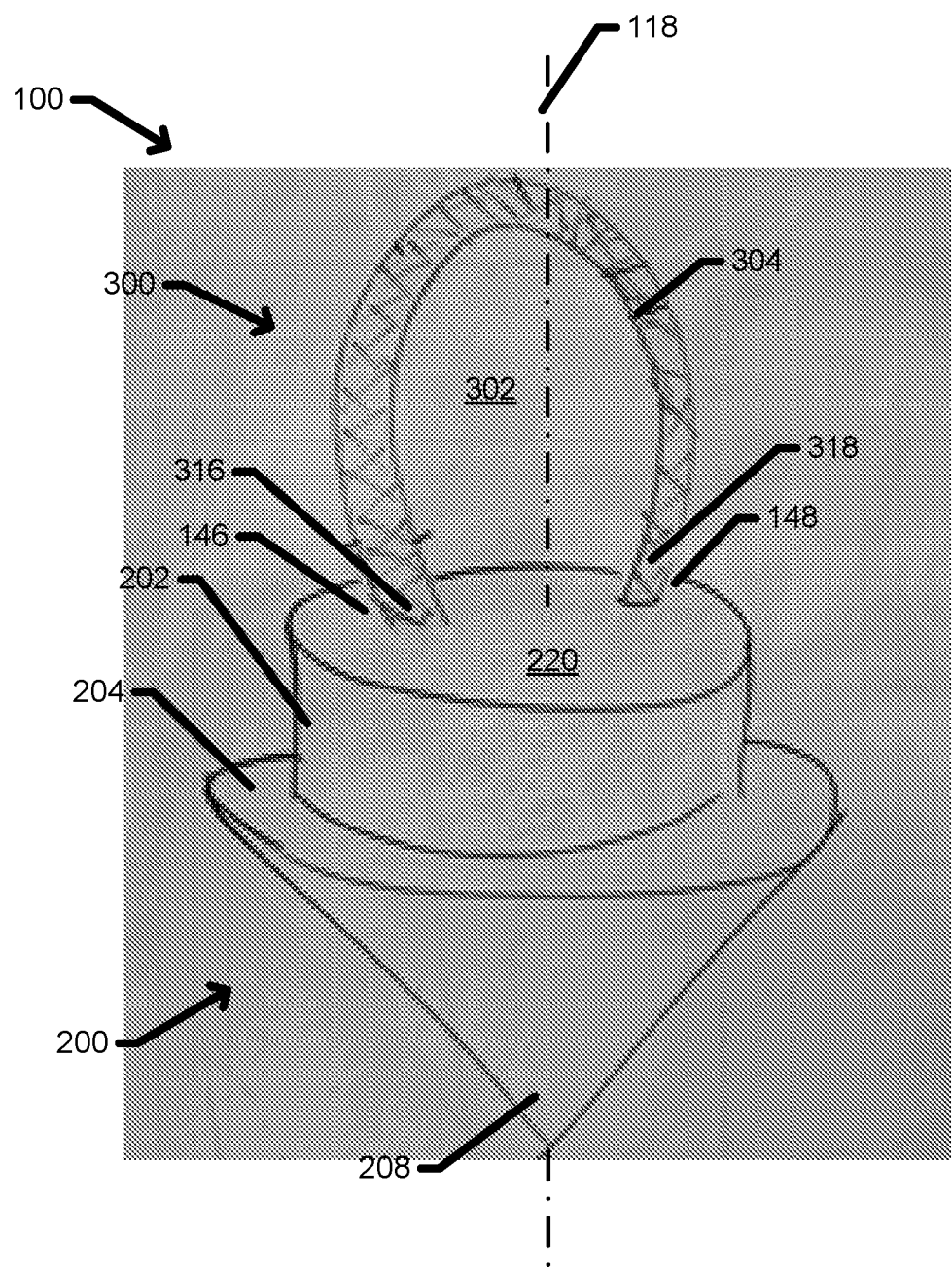
FIG. 20 is a top perspective view of a distal tip with an exchange ring formed from a single flexible strand with opposed ends attached to a proximal face of the distal tip.

FIG. 20 is a side view of a distal tip 200 and suture exchange fitting 300 in an aspect. In this aspect, the exchange ring 304 may be created by adhering the first tail 316 and the second tail 318 of a single length of a flexible material including, but not limited to, a suture segment directly to the distal tip 200 at first and second spaced-apart locations 146/148; the first and second tails 316/318 may also be directly overmolded into the distal tip 200 at the first and second spaced-apart locations 146/148. In this aspect, the distal tip 200 may be provided with a proximal face 220 to provide a surface suitable for adhering the first and second tails 316/318. In another aspect, the proximal face 220 may be provided with one or more fixation features (not shown) at the first and second spaced-apart locations 146/148 to further facilitate the adhesion of the first and second tails 316/318 to the distal tip 200. Non-limiting examples of suitable fixation features include depressions, grooves, channels, bores, lumens, and raised features such as clips, hooks, and the like.

ii) Flexible Exchange Rings

In various aspects, the exchange ring 304 may be constructed from any suitable flexible material without limitation. In one aspect, the exchange ring 304 may be constructed from standard suture. In another aspect, the suture may be a continuous ring including, but not limited to a suture formed through a continuous braiding process. In this one aspect, the first tail 316 and the second tail 318 may extend into one another in a continuous manner to form the continuous loop.

In another aspect, the suture may be a single piece ending in a first tail 316 and a second tail 318. In this other aspect, the first tail 316 and a second tail 318 may be secured to the body 102 and/or distal tip 200 at a first spaced apart location 146 and at a second spaced-apart location, respectively, as described herein previously.

In yet another aspect, the first tail 316 and the second tail 318 of the suture may be tied to one another in a knot to form the exchange ring 304. Referring again to FIG. 7 and FIG. 8, the knot 320 may be situated near the distal end 208 of the distal tip 200. In an aspect, the distal end 208 may include a feature to retain the knot 230 including, but not limited to, a distal recess 206. In various aspects, the knot 320 may be one of any variety of suitable knots. However, the knot 320 may be configured to avoid undesirable stress concentrations in the suture that may result in a premature failure of the exchange ring 304, and may be further configured to withstand any anticipated loads on the tissue anchor device 100 during prolonged use without slipping or untying.

In an aspect, the knot 320 may be reinforced to prevent slipping or untying using any suitable knot reinforcement method. Non-limiting examples of suitable knot reinforcement methods include: heating and melting the first and second tails 316/318 of the knot 320, applying a stiff material to the first and second tails 316/318 of the knot 320, and any combination thereof. In another aspect, the knot 320 may also be set and/or reinforced by heating and melting the outer surface 322 of the entire knot in order to stiffen the material without compromising the strength of the suture. In an additional aspect, an adhesive or other coating may be applied to the outer surface 322 of the knot 320 to stiffen and reinforce the knot 320. Non-limiting examples of suitable adhesives or other coatings include: polymers, epoxies, adhesives, plastics, and any combination thereof.

In an aspect, the stiffness of at least a portion of the exchange ring 304 formed from a flexible material may be modified by the addition of one or more reinforcement features. In one aspect, the flexible material may be heated and/or melted in one or more portions to stiffen the one or more portions of the exchange ring 304. In another aspect, at least a portion of the flexible material may be coated, impregnated, and/or overmolded with adhesive or other coating material including, but not limited to: polymers, epoxies, adhesives, plastics, and any combination thereof. The stiffness of the supporting material can be controlled to allow the ring to collapse once a defined load has been reached.

In another aspect, the first tail 316 and the second tail 318 may be joined by a joining member (not shown) configured to retain the first and second tails 316/318, thereby forming the continuous ring. The joining member may be any suitable joining device including, but not limited to: a splice, a clamp, and a joiner. The joining member may be constructed from any suitable material including, but not limited to: metals, polymers, epoxies, adhesives, plastics, and any combination thereof. The joining member may be affixed to the first and second tails 316/318 by any suitable mechanism including, but not limited to: crimping, molding, twisting, advancing a clamp screw or set screw, repositioning a latch, and any other suitable mechanism. In an aspect, the joining member may be seated within a distal recess 206 formed within the distal tip 200 opposite to the distal end 208, as illustrated in FIG. 8.

In another aspect, the stiffness of at least a portion of the exchange ring 304 formed from a flexible material may be stiffened by the incorporation of additional reinforcing elements. The additional reinforcing elements may be incorporated at any portion of the exchange ring 304 and may be attached, imbedded or otherwise incorporated as described herein below. In various aspects, the one or more additional reinforcing elements may be configured to fail upon exposure to a load in excess of a collapsing force 306 to enable the collapsing of the aperture 102 and locking of the one or more sutures 110 within the aperture 102 after completion of a suture exchange.

Figure 21:
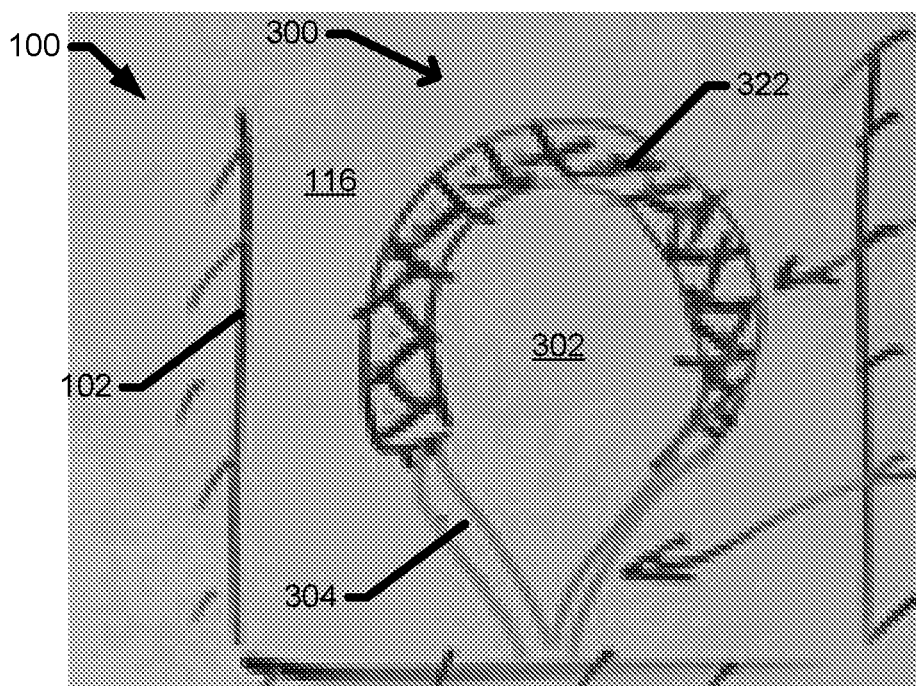
FIG. 21 is a cross-sectional side view of a tissue anchor device with an exchange ring formed from a single flexible strand reinforced by a braided sheath.
Figure 22:
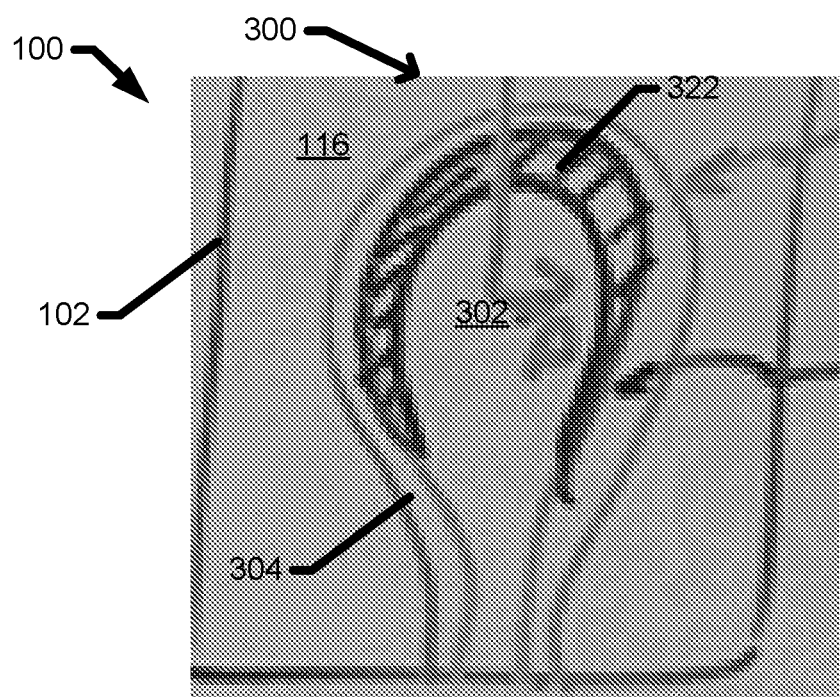
FIG. 22 is a cross-sectional side view of a tissue anchor device with an exchange ring formed from a single flexible strand reinforced by a U-shaped reinforcing element.

FIG. 21 is a side view of an exchange ring 304 that includes a flexible material and an external reinforcing element 322. In one aspect, the external reinforcing element 322 may be provided in the form of a sleeve situated over the top of the exchange ring 304, as illustrated in FIG. 21. In another aspect, the external reinforcing element 322 may be provided in the form of a U-shaped reinforcement structure situated on at least a portion of the inner surface of the exchange ring 304 adjacent to the aperture 302, as illustrated in FIG. 22. In these aspects, the external reinforcing element 322 may be constructed of any suitably stiff and biocompatible material including, but not limited to: a polymer, a plastic, a metal, a suture sleeve, and any combination thereof. This approach may also create a smooth bearing interface to allow a repair suture 110 to more easily slide through the aperture 302 during an exchange process. To this end, the external reinforcing element 322 may be constructed of a material characterized by a relatively low friction coefficient.

Figure 23:
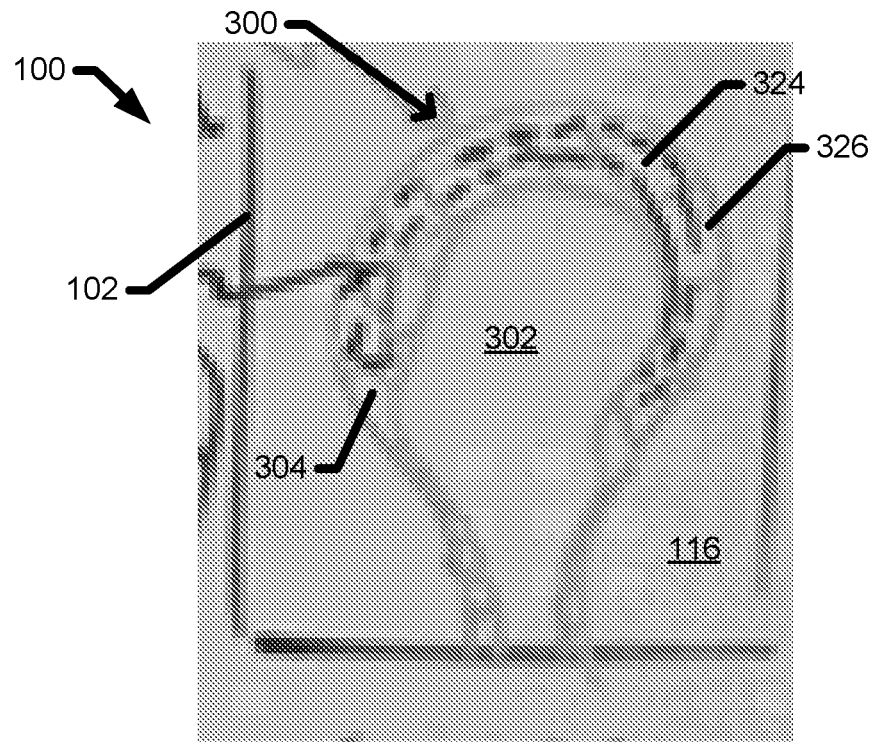
FIG. 23 is a cross-sectional side view of a tissue anchor device with an exchange ring formed from a single flexible strand reinforced by an internal reinforcing element.

FIG. 23 is a side view of an exchange ring 304 that includes a flexible material and an internal reinforcing element 324. In one aspect, the internal reinforcing element 324 may be provided in the form of a reinforcing insert 324 situated in a suture lumen 326. In one aspect, the top of the exchange ring 304. In this aspect, the external reinforcing element 322 may be constructed of any suitably stiff and biocompatible material including, but not limited to: a polymer, a plastic, a metal including NiTi, stainless steel, and/or titanium, and any combination thereof.

Figure 24:
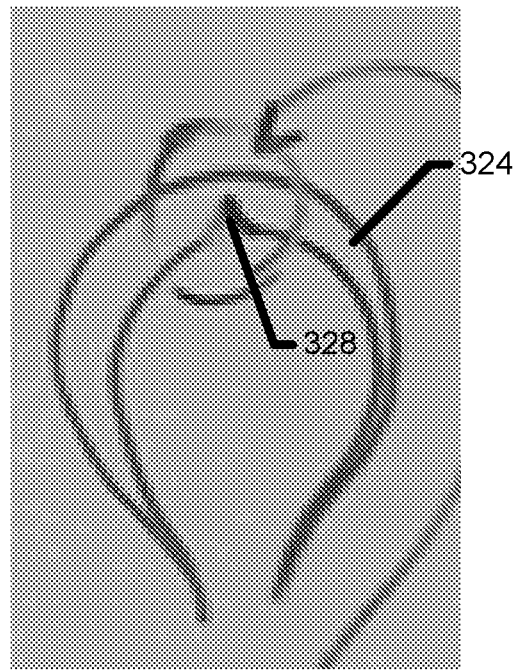
FIG. 24 is a side view of a U-shaped reinforcing element with a defect configured to enable the collapse of the exchange ring under a collapsing load.

In various aspects, the stiffness of the reinforcing element 322/324 may be modulated through a variety of means to allow the exchange ring 304 to collapse once the collapsing force 306 has been exceeded after a suture exchange. The dimensions of the reinforcing element 322/324 may be configured to create a region of high stress that may collapse upon exposure to a force in excess of the collapsing force 306. By way of non-limiting example, the reinforcing element 322/324 may include a local thin or hollow region configured to fail, thereby enabling the collapse of the exchange ring 304. The reinforcing element 322/324 may be provided in the form of a composite element in which one or more regions may be constructed from a weaker material configured to preferentially fail before the remainder of the reinforcing element 322/324, thereby enabling the collapse of the exchange ring 304. The reinforcing element 322/324 may further include one or more regions in which a portion of the material has been removed, including, but not limited to defects, cutouts, gaps, and/or perforations. FIG. 24 is a side view of an internal reinforcing element that includes a defect 328 configured to preferentially fail and collapse the exchange ring 304 at sufficiently high loads.

2. Rigid Suture Exchange Fittings

In various aspects, the exchange ring 304 may also be constructed from any suitable rigid and biocompatible material without limitation. Non-limiting examples of suitable rigid materials include: polymers, plastics, metals including NiTi, stainless steels, and/or titanium and titanium alloys, and any combination thereof. In one aspect, the exchange ring 304 may be constructed from a wire, a braided cable, a coated wire, a coated braided cable, a molded plastic, and any other suitable rigid structure. In an aspect, the rigid material of the exchange ring 304 may provide a smooth bearing interface defining the aperture 302 to allow the repair suture 110 to more easily slide through the exchange ring 304 during the exchange process. Further, the rigid exchange ring 304 may be well-suited to maintain the aperture 302 in the presence of various loads associated with a suture exchange. In an aspect, the stiffness of the rigid exchange ring 304 may be modulated through a variety of means to allow the exchange ring 304 to collapse once the collapsing force 306 has been exceeded after a suture exchange. The dimensions of the exchange ring 304 may be configured to create a region of high stress that may collapse upon exposure to a force in excess of the collapsing force 306. By way of non-limiting example, the exchange ring 304 may include a local thin or hollow region configured to fail, thereby enabling the collapse of the exchange ring 304. The exchange ring 304 may be provided in the form of a composite element in which one or more regions may be constructed from a weaker material configured to preferentially fail before the remainder of the exchange ring 304, thereby enabling its collapse. The exchange ring 304 may further include one or more regions in which a portion of the material has been removed, including, but not limited to defects, cutouts, gaps, and/or perforations.

In one aspect, the rigid exchange ring 304 may be relatively limited with respect to the range of rotation of the aperture 102 enabled during a suture exchange. In various other aspects, the suture exchange fixture 200 may include additional features to enable the rotation of the exchange ring 304 within a predetermined range during a suture exchange as described previously herein. These additional features may enable rotation of a rigid suture exchange fixture 200 within a limited range. Non-limiting examples of additional features include various cylindrical or spherical cavities formed within the passage 116 of the body and/or the distal tip 200 that may interact with one or more features of the suture exchange fitting 300 to enable the rotation of the aperture 302 during a suture exchange. In another additional aspect, the rigid exchange ring 304 may include additional features to permit the exchange ring 304 to freely swivel without limitation.

FIG. 50A, FIG. 50B and FIG. 50C are cutaway views of a tissue anchor device 100 that include a free-swiveling rigid exchange ring 304 in one aspect. Referring to FIG. 50A, the tissue anchor device 100 in this aspect may include the exchange ring 304, positioned within the passage 116 of the tissue anchor device 100. The exchange ring 304 may be configured to rotate or swivel freely with respect to the body 102 of the tissue anchor device 100. The swiveling functionality in this aspect decouples the rotational orientation of the exchange ring 304 from the rotational orientation of the body 102 of the tissue anchor device 100, thereby allowing the orientation of one or more sutures 110 threaded through the aperture 302 of exchange ring 304 in any desired direction without regard to the rotation of the body 102 of the tissue anchor device 100.

FIG. 50A illustrates a cut-away view of the tissue anchor device 100 that includes the free-swiveling exchange ring 304 in one aspect. A first rotational orientation of the body 102 is illustrated in FIG. 50A, with a body landmark 190 shown as a reference. The exchange ring 304 may be positioned within the aperture 302 of body 102. As shown in FIG. 50A, the rigid exchange ring 304 may be retained via a flexible link 192 that permits essentially unlimited rotation about the screw axis.

In various aspects, the link 192 may be constructed from any suitable flexible material without limitation including, but not limited to, a thread or suture material. The link 192 may be provided in any form without limitation including, but not limited to, a strip, a loop, a band, or any other suitable flexible form capable of enabling free rotation of the exchange ring 304. As illustrated in FIG. 50A, the flexible link 192 may be provided in the form of a suture or thread that is doubled and looped through the aperture 302 of the exchange ring 304 and passed through the distal opening 138 within the distal tip 200 of the tissue anchor device 100 in an aspect. In this aspect, the distal end 196 of the link 192 may terminate in a knot 194 or other suitable joining or terminating structure to retain the distal end 196 outside of the distal tip 200, thereby providing a robust and swiveling attachment of the exchange ring 304 to the body 102. The exchange ring 304 may be of a different structure or configuration than that shown in FIG. 50A that allows free-swiveling movement relative to the body 102 of the tissue anchor device 100 without departing from the spirit of the invention.

FIG. 50B is an illustration of the tissue anchor device 100 shown in FIG. 50A with the body 102 rotated at a 45° angle about the screw axis relative to the orientation shown in FIG. 50A, as evidenced by the change in orientation of the body landmark 190. As shown in FIG. 50B, while the body 102 of the tissue anchor device 100 is rotated at a 45° angle, the orientations of the exchange ring 304 and aperture 302, the link 192, and the one or more sutures 110 are unchanged from the orientations illustrated in FIG. 50A.

FIG. 50C is an illustration of the tissue anchor device 100 shown in FIG. 50A with the body 102 rotated at a 90° angle about the screw axis relative to the orientation shown in FIG. 50A, as evidenced by the change in orientation of the body landmark 190. As shown in FIG. 50C, while the body 102 of the tissue anchor device 100 is rotated at a 90° angle, the orientations of the exchange ring 304 and aperture 302, the link 192, and the one or more sutures 110 are unchanged from the orientations illustrated in FIG. 50A and FIG. 50B.

The decoupling of the rotational orientation of the exchange ring 304 from those elements of the tissue anchor device 100 affixed within a bone provides advantages that would be appreciated by those of skill in the art. The exchange ring 304 may rotationally orient in a direction that minimizes the tortuosity of the path traversed by the one or more sutures 110 threaded through the aperture 302 of the exchange ring 304. In contrast, a suture 110 loaded into a fixed thread-holding member (not shown) may become twisted when the suture anchor device (not shown) is deployed and screwed into a bone. Without being limited to any particular theory, reducing the tortuosity of the suture's path may reduce the amount of force required to exchange one or more sutures 110 between one or more tissue anchor devices 100 as described herein. Swiveling may further allow a suture 110 threaded through an exchange ring 304 to slide with minimal tortuosity when tensioning the suture 110 within a particular repair construct as described herein below.

Figure 25:
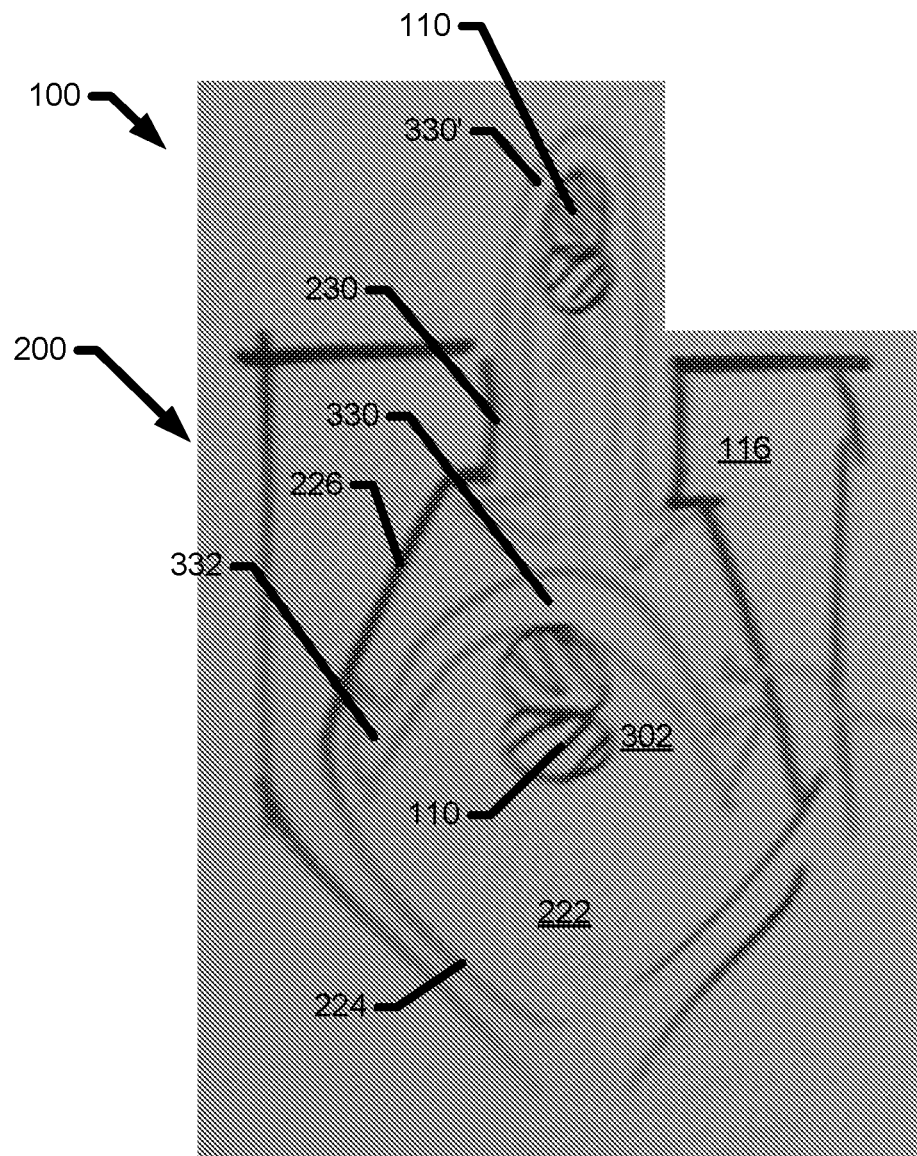
FIG. 25 is a cross-sectional side view of a tissue anchor device with an exchange ring formed as a clip collapsed by an upward pull at greater than the collapsing force.

FIG. 25 is a cross-sectional side view of a tissue anchor device 100 with a rigid exchange ring provided in the form of a bar or clip 330 in an aspect. In this aspect, the clip 330 may be contained within a cavity 222 formed within the distal tip 200. The lower wall 224 of the cavity may be relatively wide, thereby permitting the clip 330 to rotate within the cavity 222 during a suture exchange. In an aspect, the cavity 222 may include an annular groove (not shown) formed in the lower wall 224 within which the ends 332 of the clip 330 may slide to enable rotation of the aperture 302 during a suture exchange. In this aspect, the annular groove may extend around the entire circumference of the lower wall 224, or the annular groove may extend over a portion of the circumference of the lower wall 224 to constrain the rotation of the clip 330 to within a limited range. In this aspect, the upper wall 224 may taper proximally from the relatively wide lower wall 224 to a narrow neck 230. During a suture exchange, the clip 330 may be subjected to relatively low pulling forces from the one or more sutures 110. After completion of the suture exchange, a pulling force in excess of the collapsing force 306 may cause the clip 330 to deform into a collapsed clip 330' in which the ends 332 of the clip 330' are forced together by the narrow diameter of the neck 230. In the collapsed configuration, the clip 330' may entrap the one or more sutures 110, thereby preventing any further sliding movements.

Figure 26:
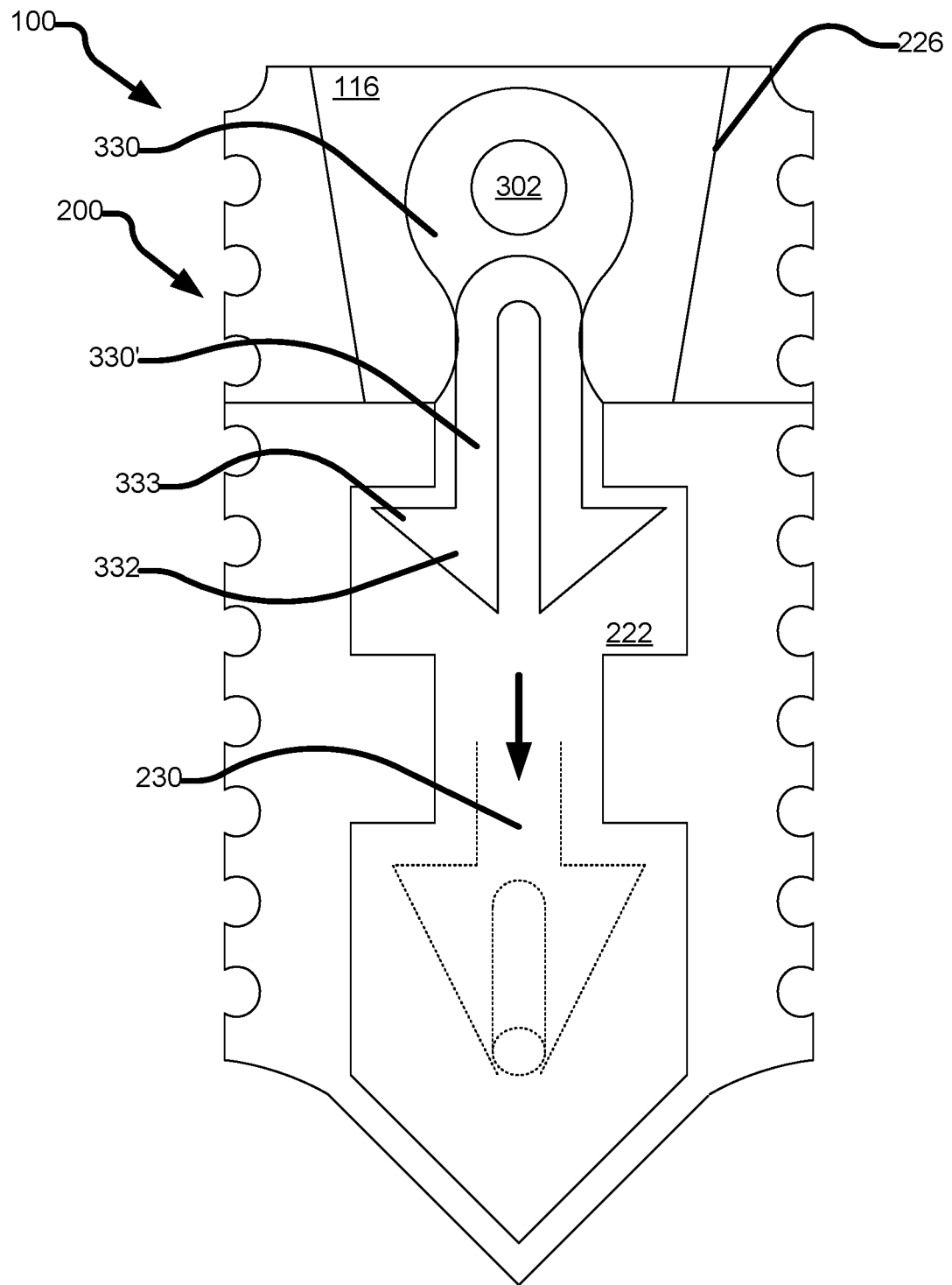
FIG. 26 is a cross-sectional side view of a tissue anchor device with an exchange ring formed as a clip collapsed by a downward push at greater than the collapsing force.

FIG. 26 is a cross-sectional side view of a tissue anchor device 100 with a rigid exchange ring 304 provided in the form of a U-shaped clip 330 in another aspect. In this other aspect, the U-shaped clip 330 may be contained within a cavity 222 formed within the distal tip 200. The wall 224 of the cavity 222 may be relatively wide, thereby permitting the U-shaped clip 330 to rotate within the cavity 222 during a suture exchange. In an aspect, the cavity 222 may include an annular groove (not shown) formed in the wall 224 within which the ends 332 of the U-shaped clip may slide to enable rotation of the aperture 302 during a suture exchange in a manner similar to the annular groove described herein previously in connection with the suture exchange fitting 300 of FIG. 25. In this aspect, the distal tip may further include a relatively narrow neck 230 situated distally to the cavity 222. During a suture exchange, the U-shaped clip in the open configuration is subjected to relatively low pulling forces from the one or more sutures 110 and freely rotates within the cavity 222. After completion of the suture exchange, the U-shaped clip may be pushed down distally into the neck 230, thereby forcing the ends 332 of the clip 330 to deform into a collapsed clip 330'. In the collapsed configuration, the collapsed clip 330' may entrap the one or more sutures 110, thereby preventing any further sliding movements. The ends 332 of the clip 330' may include barbs 333 that may retain the ends 332 within the cavity 222; the collapsed clip 330' may resist unlocking from the cavity 222 even when the repair sutures 110 are tensioned.

Figure 27:
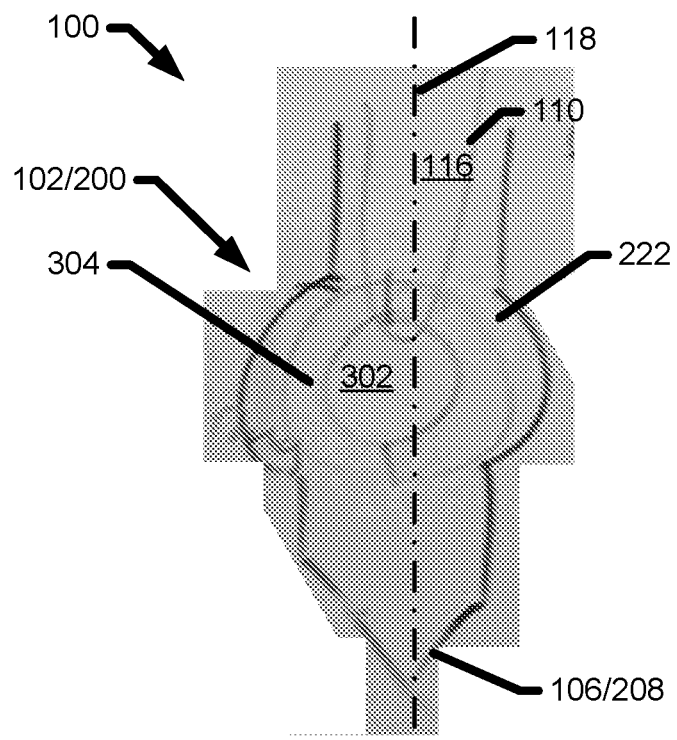
FIG. 27 is a cross-sectional side view of a tissue anchor device with an exchange ring formed as a rigid ring.

FIG. 27 is a cross-sectional side view of a tissue anchor device 100 with an exchange ring 304 provided in the form of a rigid exchange ring 304 in an additional aspect. In this additional aspect, the rigid exchange ring 304 may freely float within a cavity 222 formed within the tissue anchor device 100. In various aspects, the cavity 222 may be formed within the body 102 or within the distal tip 200 of the tissue anchor device 100. The rigid exchange ring 304 defines an aperture 302 that is sufficiently large to allow for a suture exchange. The rigid exchange ring 304 may also to rotate with respect to the longitudinal axis 118 of the tissue anchor device 100. In another aspect, the cavity 222 may be provided with one or more ridges (not illustrated) or other mechanical stops to limit the rotation of the rigid exchange ring 304 within a limited rotational range inside of the cavity 222. In an aspect, the ridges may be aligned parallel with the longitudinal axis 118 of the tissue anchor device 100.

Figure 28:
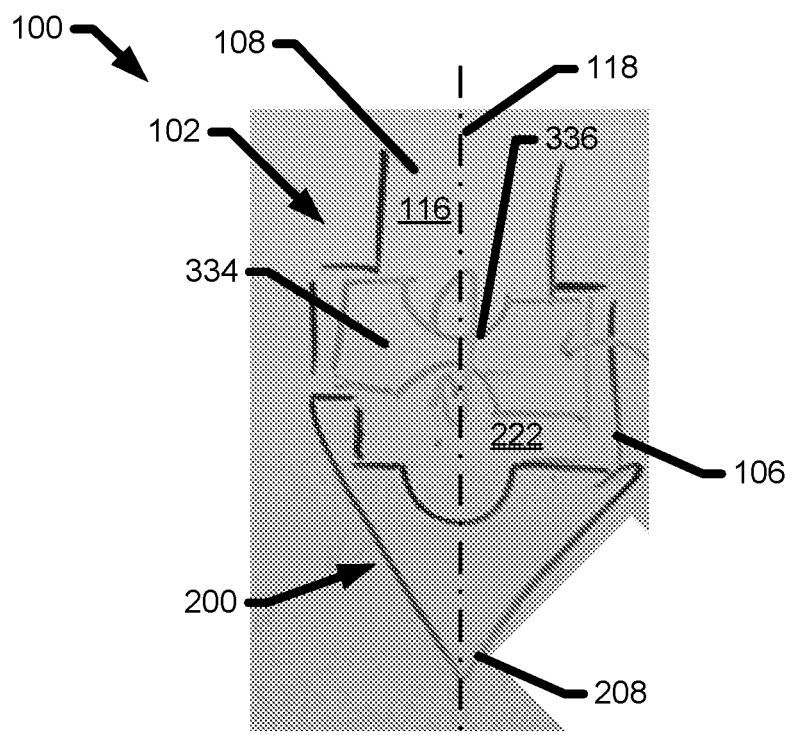
FIG. 28 is a cross-sectional side view of a tissue anchor device with an exchange ring formed as a bearing.
Figure 29:
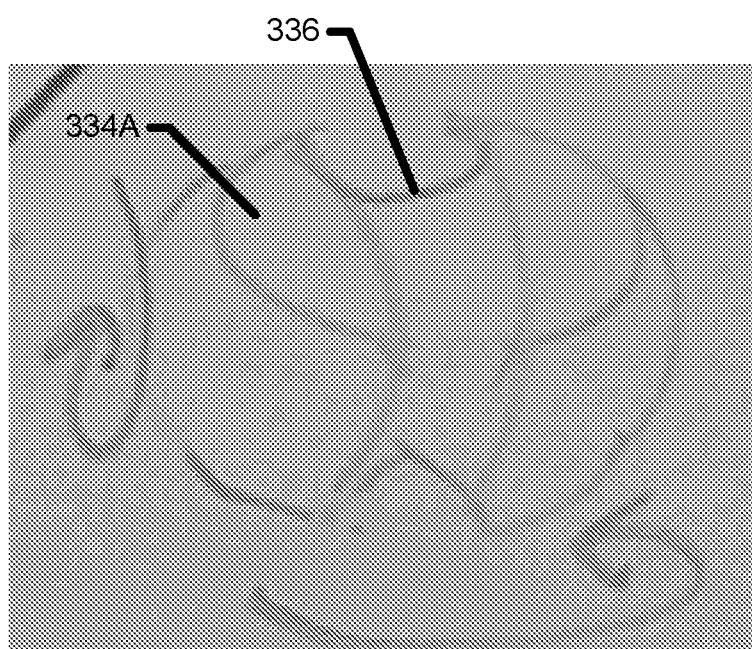
FIG. 29 is a cross-sectional side view of a tissue anchor device with an exchange ring formed as a disk-shaped bearing.

FIG. 28 is a cross-sectional side view of a tissue anchor device 100 with an exchange ring 304 provided in the form of a bearing 334 in another aspect. In this other aspect, the bearing 334 may be situated in a cavity 222 formed between the body 102 and within the distal tip 200 of the tissue anchor device 100. In an aspect, the bearing 334 may be provided as an essentially cylindrical bar with a circumferential groove 336 or neck in the mid-section of the bearing 334. The bearing 334 may be free to rotate about its own axis 338 which would ease a suture exchange. The bearing 334 may also be free to rotate around the longitudinal axis 118 of the tissue anchor device 100 to allow the one or more repair sutures 110 (not shown) to self-align in the direction of suture tension. The groove 336 provides a guide for the one or more sutures 110 and prevents any sutures 110 from becoming pinched between the inner wall 120 of the body 102 and the bearing 334. FIG. 29 is a perspective view of a disk-shaped bearing 334A with a groove 336 formed at the mid-section of the bearing 334A in another aspect.

Figure 30:
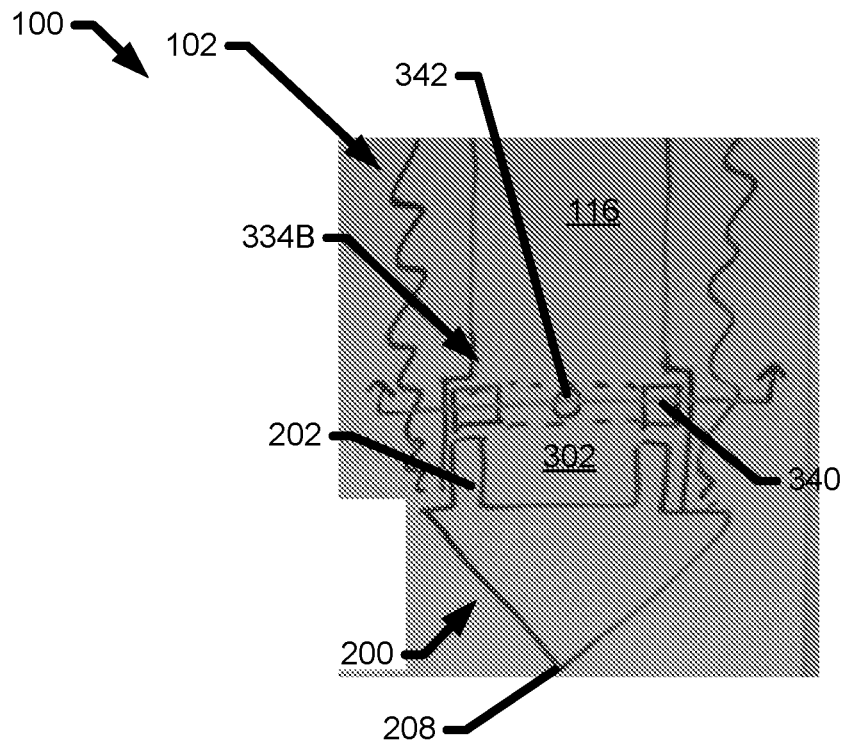
FIG. 30 is a cross-sectional side view of a tissue anchor device with an exchange ring formed as a ring with a transverse bar.
Figure 31:
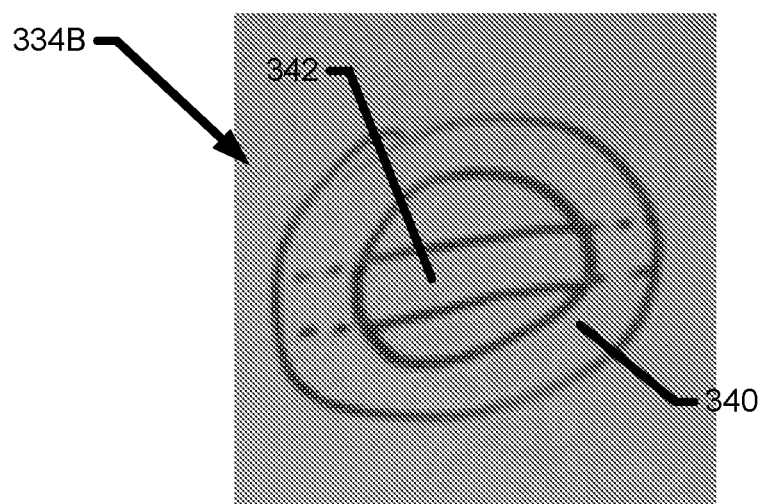
FIG. 31 is a top view of an exchange ring formed as a ring with a transverse bar.

FIG. 30 is a cross-sectional side view of a tissue anchor device 100 with an exchange ring 304 provided in the form of a bearing 334B in another aspect. In this other aspect, the bearing 334 may be situated in a cylindrical cavity 222 formed between the body 102 and within the distal tip 200 of the tissue anchor device 100. In an aspect, the bearing 334B may be provided as a ring 340 with a transverse bar 342 across the ring 340. FIG. 31 is a top view of the bearing 334B in this aspect. The bearing 334B may be free to rotate about its own axis 338 which would ease a suture exchange. The bearing 334 may also be free to rotate around the longitudinal axis 118 of the tissue anchor device 100 to allow the one or more repair sutures 110 (not shown) to self-align in the direction of suture tension. The groove 336 provides a guide for the one or more sutures 110 and prevents any sutures 110 from becoming pinched between the inner wall 120 of the body 102 and the bearing 334. FIG. 31 is a perspective view of a disk-shaped bearing 334A with a groove 336 formed at the mid-section of the bearing 334A in another aspect.

Figure 32:
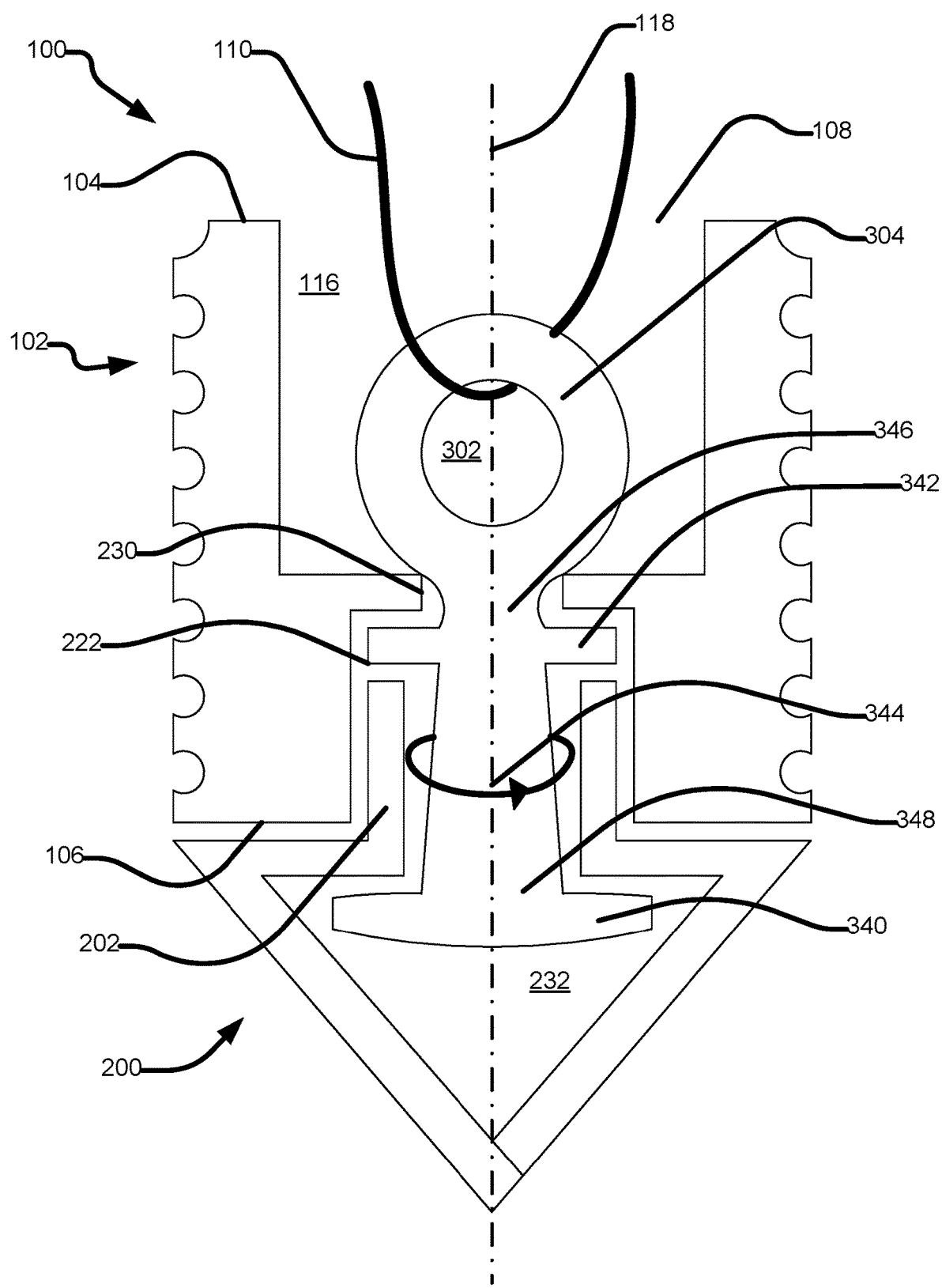
FIG. 32 is a cross-sectional side view of a tissue anchor device with an exchange ring attached to a shaft with at least one bearing further attached to the shaft.

FIG. 32 is a cross-sectional side view of a tissue anchor device 100 with an exchange ring 304 attached to a shaft 344 provided with one or more bearings 340/342 in another aspect. In this aspect, the exchange ring 304 may be attached to a proximal end 346 of the shaft 344, and a first bearing 340 may be attached to a distal end 348 of the shaft 344 opposite to the proximal end 346. A second bearing 342 may also be attached to a middle portion of the shaft 344 between the exchange ring 304 and the first bearing 340. The exchange ring 304 may be situated within the passage 116, rendering the aperture 302 accessible to the one or more sutures 110 via the proximal opening 108 of the body 102. The first bearing 340 may be retained within a second cavity 232 formed within the distal end 200, and the second bearing 342 may be retained within a cavity 222 formed between the distal end 106 of the body 102 and the proximal shaft 202. The first bearing 340 and the second bearing 342 may freely rotate about the longitudinal axis 118 of the tissue anchor device 100. The body 102 may have a narrow neck 230 defined at a distal end of the aperture 116 to entrain the shaft 344 between the exchange ring 304 and the second bearing 342. One or more sutures 110 may be looped through the aperture 302 in this aspect.

Figure 33:
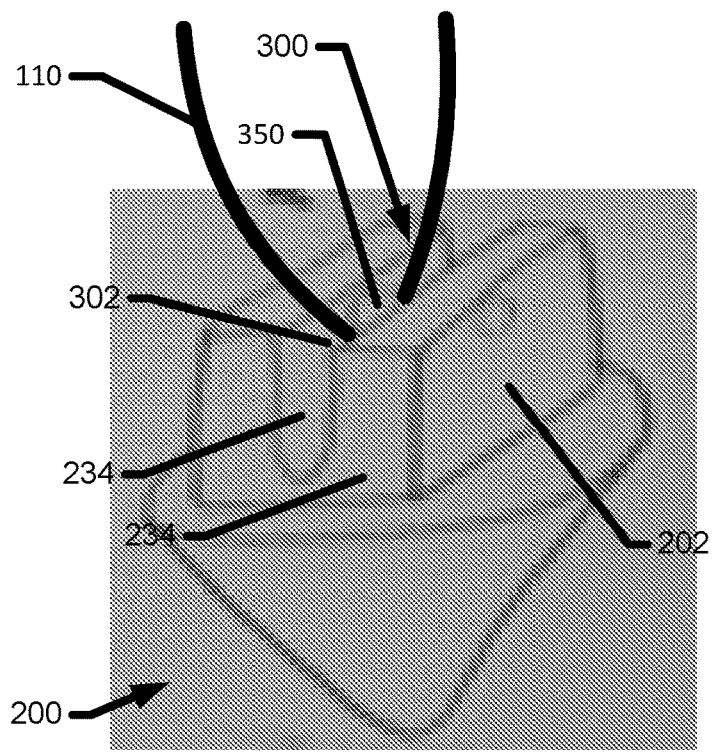
FIG. 33 is a perspective view of a distal tip with a proximal groove and a transverse bar forming a suture exchange fitting.
Figure 34:
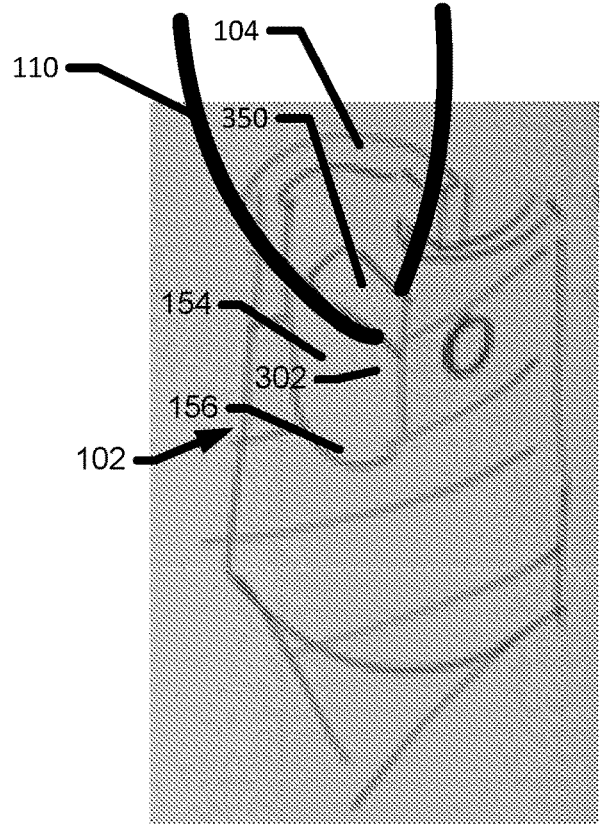
FIG. 34 is a perspective view of a body of a tissue anchor device with a proximal groove and a transverse bar forming a suture exchange fitting.

FIG. 33 is a perspective view of a distal tip 200 in which a groove 234 is formed in the proximal shaft 202 in an aspect. A bar 350 may be inserted across transverse to the groove 234 to form a suture exchange fitting 300. One or more sutures 110 may be inserted through an aperture 302 formed between the bar 350 and the base 236 of the groove 234. The bone anchor can be constructed such that it has a transverse break in the proximal section of the body of the bone anchor to create a space for the suture exchange. The entire tip assembly may be attached to the body 102 (not shown) via the distal opening 138. The distal tip 200 may be configured to freely rotate about the longitudinal axis 118 of the tissue anchor device 100. FIG. 34 is a perspective view of a body 102 within which a groove 154 is formed within the proximal end 104 of the body 102 in an aspect. In this aspect, a bar 350 may be inserted transversely across the groove 154. One or more sutures 110 may be looped through the aperture 302 formed between the bar 350 and the base 156 of the groove 154.

In both of the aspects illustrated in FIG. 33 and FIG. 34, the bar 350 may be provided in a variety of cross-sectional shapes and lengthwise profiles without limitation. In an aspect, the bar may be configured to provide a low-friction suture exchange fitting 300 capable of accommodating a range of suture pulling forces and changes in the directions of suture pulling forces associated with a suture exchange and the fixation of a soft tissue to a bone tissue using the tissue anchor device 100. Non-limiting examples of suitable cross-sectional shapes for the bar 350 include circular, elliptical, crescent-shaped and the like. Non-limiting examples of suitable lengthwise profiles for the bar 350 include: linear, as illustrated in FIG. 33 and FIG. 34; and curved including an arched, parabolar, and/or semi-circular lengthwise profile. In another aspect, the bar may 164 be provided with additional features including, but not limited to: local thinning of the bar 350 cross-sectional dimension and/or notches, perforations and/or or other defects formed within at least a portion of the bar 350, and any combination thereof to enable the collapse of the bar 350 into a collapsed configuration when the bar is subjected to a pulling force in excess of a collapsing force as described herein previously.

Figure 35:
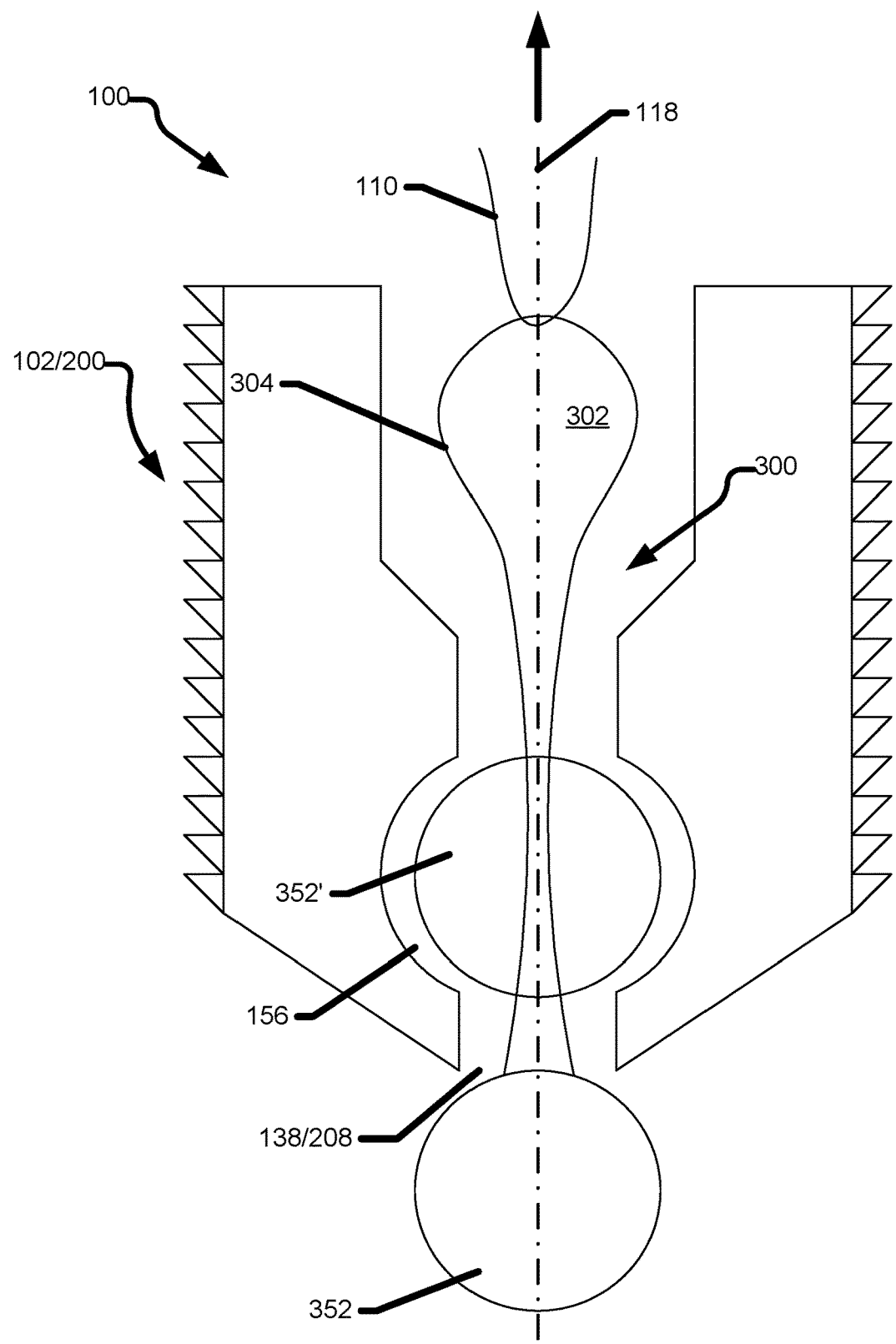
FIG. 35 is a cross-sectional side view of a tissue anchor device with an exchange ring attached to a ball.

FIG. 35 is a cross-sectional side view of a tissue anchor device 100 with the suture exchange fitting 300 provided in the form of an exchange ring 304 attached to a ball 352 that is pulled into a socket 156 formed at the distal opening 138 of the bone anchor body 102 or at the distal end 138 of the distal tip 200. The exchange ring 304 may consist of a prefabricated ring produced from a material including, but not limited to, a metal, a polymer, a plastic, a suture, and the like. The exchange ring 304 may be attached to the ball 352 using any method including, but not limited to: overmolding the ball 352 onto a portion of the exchange ring 304 and/or bonding the exchange ring 304 onto the ball 352 with a biocompatible adhesive. The ball 325 may be pulled from outside the distal end 208 or distal opening 138 into the socket 156 by pulling in a proximal direction on the exchange ring 304 either directly or via one or more sutures 110 looped through the aperture 302 within the exchange ring 304. In an aspect, the ball 352 and socket 156 may be matched in profile to enable the free rotation of the aperture about the longitudinal axis 118 of the tissue anchor device 100.

d. Sutures

Figure 36:
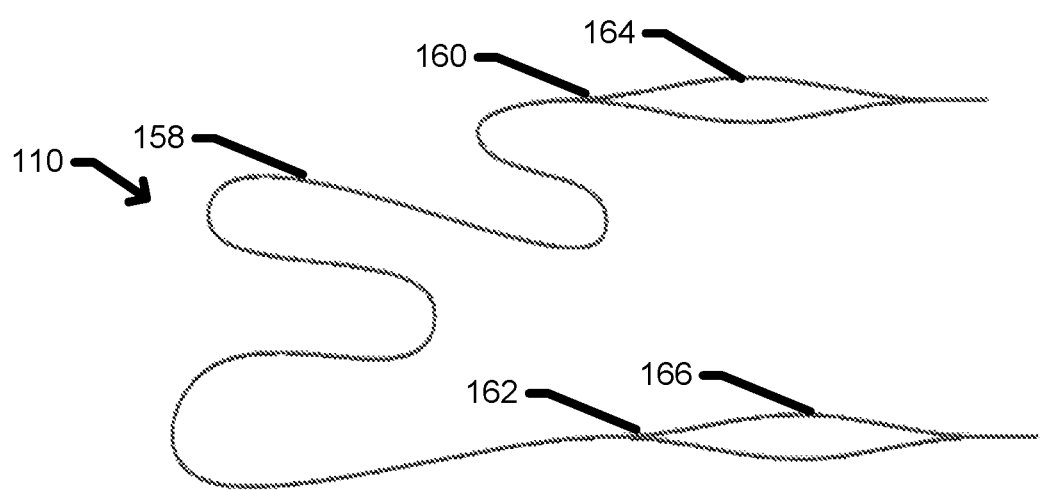
FIG. 36 is a side view of a double-looped suture.

Referring again to FIG. 2, the tissue anchor device 100 may further include one or more sutures 110 looped through the suture exchange fitting 300 within the body 102 of the tissue anchor device 100. Each suture 110 may include a single loop situated at one end of the suture 110, or two loops situated at opposite ends of the suture 110. In one aspect, a suture 110 with a single loop may enable a suture exchange in a single direction (away from the single loop) whereas a suture with a pair of loops may enable suture exchanges in two directions, thereby enhancing the range of functions potentially performed by the suture 110 within the tissue anchor device 100. The one or more sutures 110 may be exchanged between different tissue anchor devices 100 (not shown) and may be used to anchor a soft tissue to an underlying bone tissue as described in further detail herein below. FIG. 36 is an illustration of a suture 110 in one aspect. In this aspect, each suture 110 may include a main suture length 158 ending at a first suture loop 164 attached at a first suture end 160 and a second suture loop 166 attached at a second suture end 162 opposite to the first suture end 160.

Figure 37:
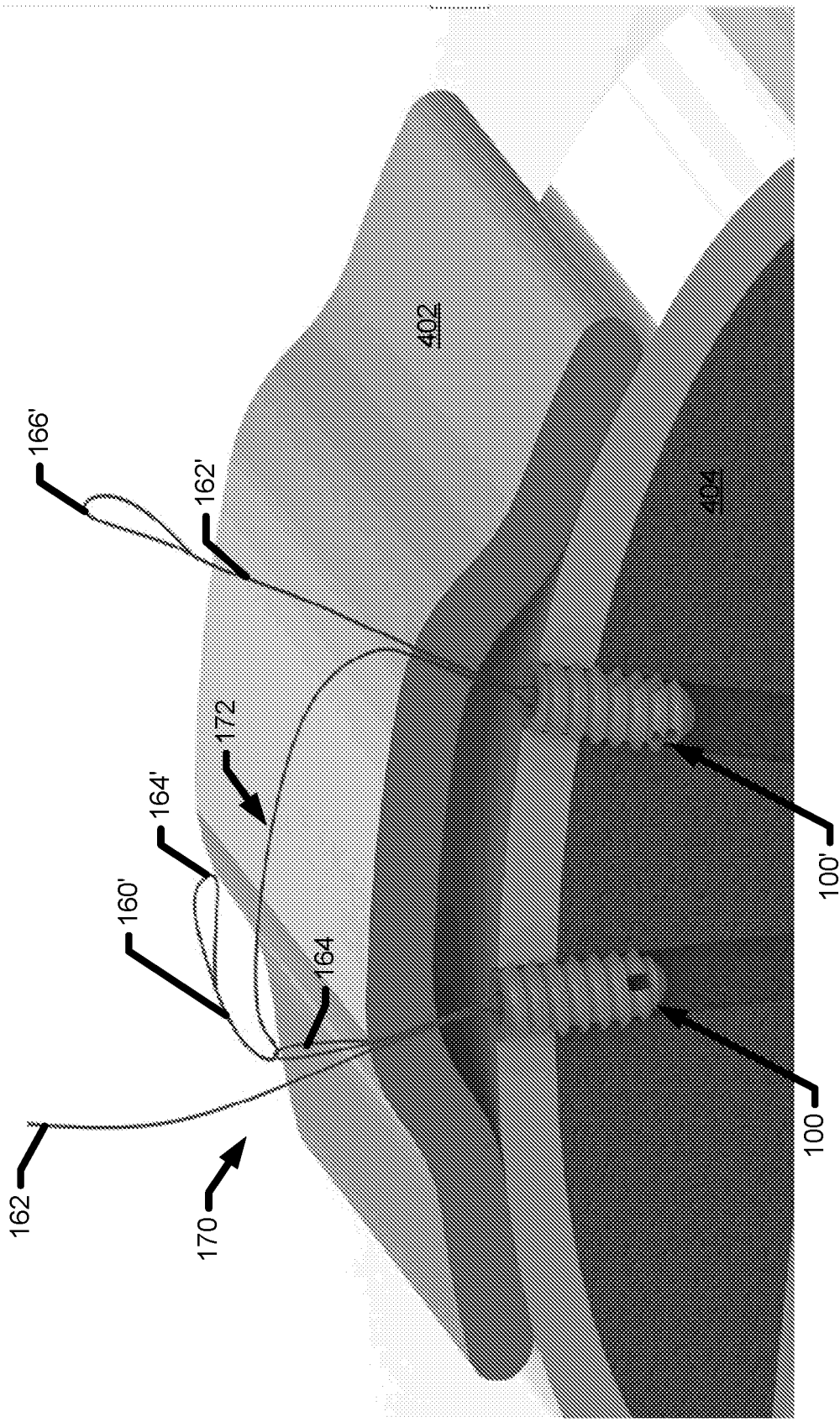
FIG. 37 is a side view of threading a first suture end through a second suture end during a suture exchange.
Figure 38:
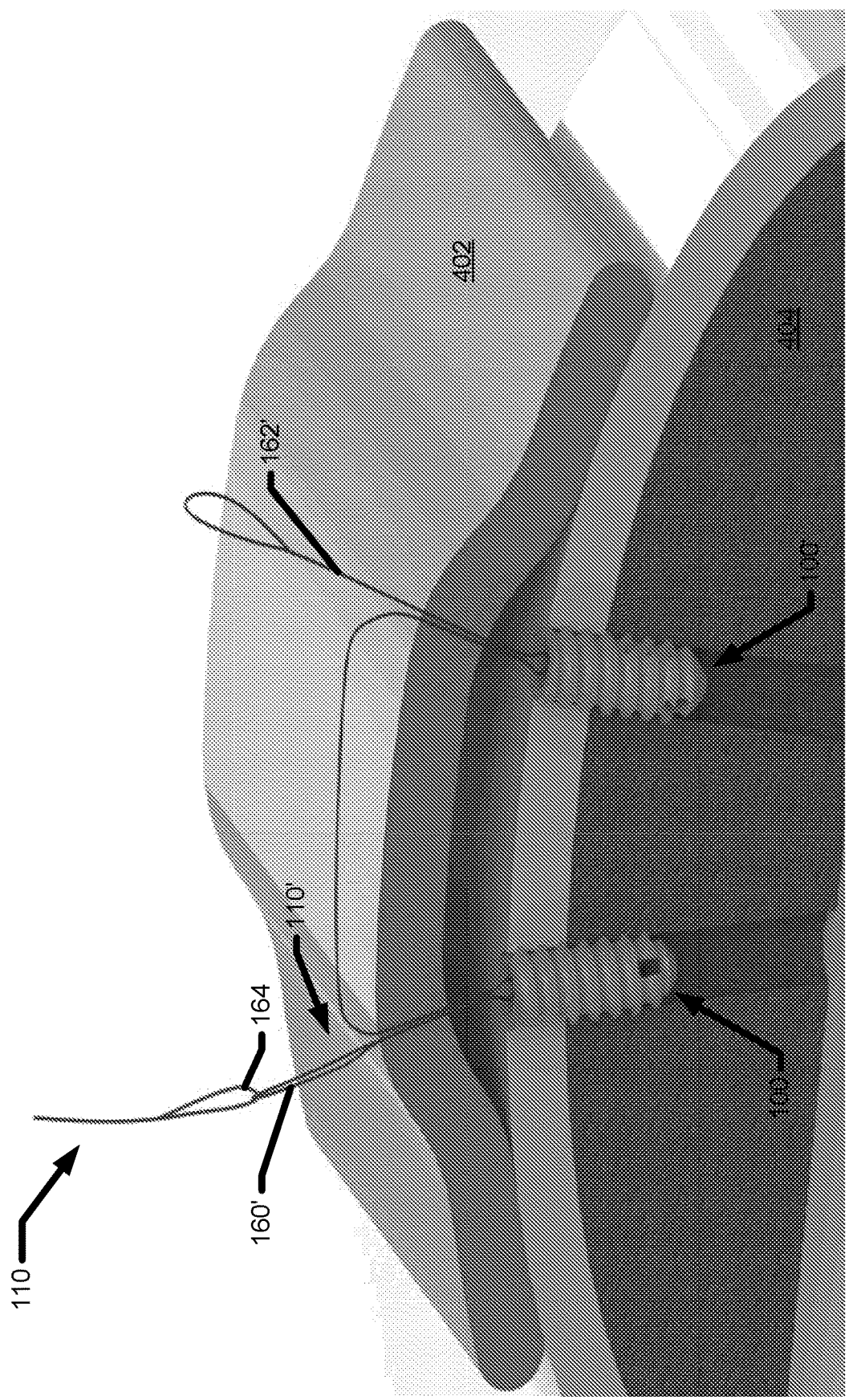
FIG. 38 is a side view of pulling a first suture end and attached second suture end during a suture exchange.

In various aspects, the suture loops 164/166 may act as snares to reversibly hold and guide the end of a second suture 172 as the second suture 172 is pulled through tissue and/or an aperture 302 of a tissue anchor device 100. FIG. 37 is a schematic view of an initial step in a suture exchange from a second tissue anchor device 100' to a first tissue anchor devices 100 in one aspect. In this aspect, a first suture end 160' and a first suture loop 164' of a second suture 172 are threaded through the first suture loop 164 of the first suture 170; this threading results in the second suture 172 being doubled over the first loop 164 of the first suture 170. The second suture end 162 of the first suture 170 may then be pulled away from the first tissue anchor device 100 to pull the second suture 172 through the first tissue anchor device 100. FIG. 38 is a schematic illustration of a subsequent stage of the suture exchange shown in FIG. 37. As illustrated in FIG. 38, the first loop 164 and doubled over second suture 172 have been pulled through the aperture 302 (not shown) of the first tissue anchor device 100, resulting in the second suture 172 being threaded through both the first tissue anchor device 100 and the second tissue anchor device 100'. The second suture 172 may now be pulled at both the first suture end 160' and the second suture end 162' to compress the soft tissue 402 against the underlying bone tissue 404.

In various aspects, the sutures 110 may be constructed of any suitable suture material without limitation. In an aspect, the sutures may be constructed of a material including, but not limited to: a monofilament, a tubular suture material, a braided suture material, and any combination thereof. Non-limiting examples of suture materials suitable for inclusion in a suture exchange fitting 300 include: non-absorbable suture materials such as polyethylene, polyester, Nylon, Gortex, Silk, polyvinylidene fluoride, polyvinylidene fluoride-co-hexafluoropropylene, Poly (ethylene, terephthalate), stainless steel and the like; absorbable suture materials such as a lactide-glycolide copolymer, polyglactin, monocryl, polyester poly(p-dioxanone), and panacryl and the like; and any combination thereof. In one aspect, the inclusion of flexible materials in the suture exchange fitting 300 may enable the deformation of the suture exchange fitting 300 under torsional loads during suture exchange, as well as the collapse of the aperture 302 under the collapsing force 306 as described herein above.

In various aspects, the size of the sutures 110 may be any size for use in an orthopedic surgical procedure consistent with the use of the tissue anchor device 100 without limitation. In one aspect, the suture diameter may range from about 0.02 mm (USP #10-0) to about 0.8 mm (USP #4). In other aspects, the suture diameters may range from about 0.02 mm to about 0.06 mm, from about 0.04 mm to about 0.08 mm, from about 0.06 mm to about 0.10 mm, from about 0.08 mm to about 0.12 mm, from about 0.10 mm to about 0.14 mm, from about 0.12 mm to about 0.16 mm, from about 0.14 mm to about 0.18 mm, from about 0.16 mm to about 0.20 mm, from about 0.18 mm to about 0.22 mm, from about 0.20 mm to about 0.30 mm, from about 0.25 mm to about 0.35 mm, from about 0.30 mm to about 0.40 mm, from about 0.35 mm to about 0.45 mm, from about 0.40 mm to about 0.50 mm, from about 0.45 mm to about 0.55 mm, from about 0.50 mm to about 0.60 mm, from about 0.55 mm to about 0.65 mm, from about 0.60 mm to about 0.70 mm, from about 0.65 mm to about 0.75 mm, from about 0.70 mm to about 0.80 mm, Non-limiting examples of suitable suture diameters include: USP #10-0 (0.02 mm), USP #9-0 (0.03 mm), USP #8-0 (0.04 mm), USP #7-0 (0.05 mm), USP #6-0 (0.07 mm), USP #5-0 (0.10 mm), USP #4-0 (0.15 mm), USP #3-0 (0.20 mm), USP #2-0 (0.30 mm), USP #0 (0.35 mm), USP #1 (0.40 mm), USP #2 (0.50 mm), USP #3 (0.60 mm), USP #5 (0.70 mm), and USP #6 (0.8 mm).

In various other aspects, the sutures 110 may have an overall length ranging from about 2.5 cm to about 70 cm. In additional aspects, the sutures 110 may have an overall length ranging from about 2.5 cm to about 10 cm, from about 5 cm to about 15 cm, from about 10 cm to about 20 cm, from about 15 cm to about 25 cm, from about 20 cm to about 30 cm, from about 25 cm to about 35 cm, from about 30 cm to about 40 cm, from about 35 cm to about 45 cm, from about 40 cm to about 60 cm, and from about 50 cm to about 70 cm.

Referring again to FIG. 36, the one or more sutures 110 may have suture loops 164/166 at opposite ends 160/162 of the suture 110. In an aspect, the dual suture loops 164/166 enable the suture 110 to be pulled toward the first suture end and/or the second suture end 162 as needed in the course of a surgical procedure. The double suture loops 164/166 enable suture pull-through in any direction, change of direction, multiple-anchor utilization, after insertion of the tissue anchor device 100, during post-insertion linkage changes, and during a remedial surgical procedure including, but not limited to reverse a repair and/or changing a method of linkage.

In an aspect, the first and second loops suture loops 164/166 may be configured to pull a second suture 172 through a soft tissue and/or an aperture 302 within a tissue anchor device 100. As a consequence, the strength of the first and second suture loops 164/166 may be less than the tensile strength of the main suture length 158, which may be subjected to relatively higher tensions in order to affix a soft tissue to an underlying bone tissue. In another aspect, the first and second loops suture loops 164/166 may be configured to reduce the suture tension associated with pulling the second suture 172 and optionally one or more additional attached sutures 110' through the soft tissue and/or aperture 302. In this other aspect, the first and second loops suture loops 164/166 may be constructed with a low profile configuration including one or more of at least several features including, but not limited to: relatively low suture diameter, compact collapsed size, smooth transition between the suture end 160/162 and the corresponding suture loop 164/166.

In one aspect, the first and second loops suture loops 164/166 may be constructed of the same suture material as the main suture length 158. In this aspect, the loops 164/166 may be formed by forming a loop at the first and second suture ends 160/162 and attaching each suture tip to its respective suture end 160/162. The tips may be attached by any suitable means including, but not limited to: continuous braiding of the loop, biocompatible adhesive, melting/welding, and any combination thereof. In another aspect, the first and second loops suture loops 164/166 may be constructed of a different or smaller-diameter material relative to the main suture length 158. In this other aspect, the material used to construct the first and second loops suture loops 164/166 may reduce the overall size of the loops in a collapsed configuration, thereby reducing pulling force during a suture change.

Figure 39:
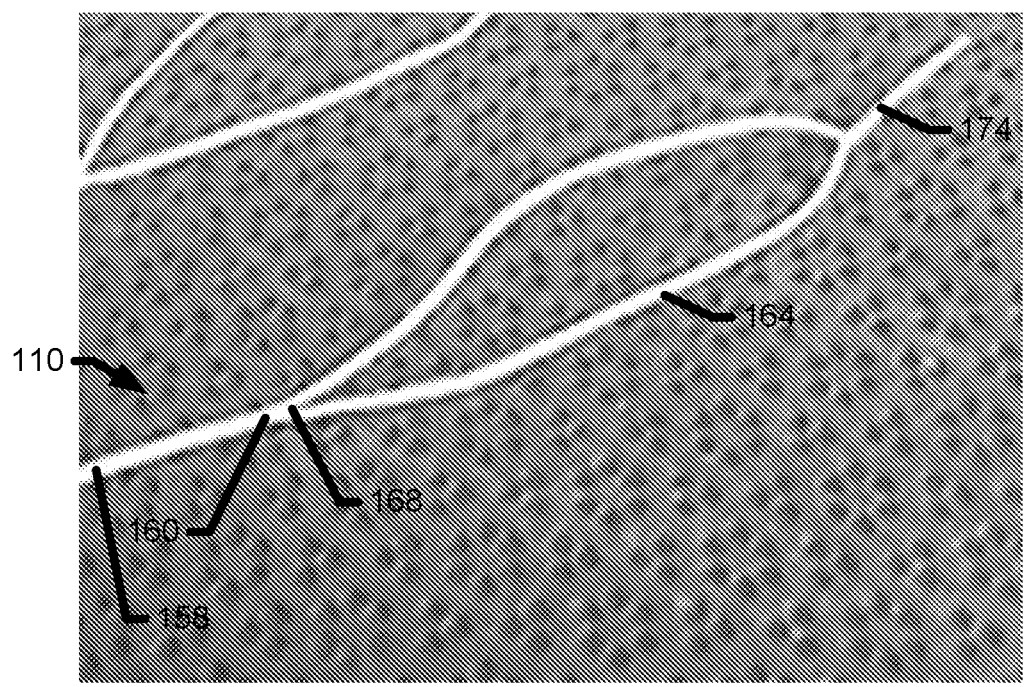
FIG. 39 is a top view of a suture loop formed from a bifurcation of a suture.

FIG. 39 is top view of a first suture loop 164 formed by a bifurcation 168 of the main suture length 158 at the first suture end 164 in one aspect. In this aspect, the distal portion of the loop 164 may rejoin to form a full-diameter loop tip 174. In this aspect, the loop 164 may be securely attached to the suture end 160 by virtue of the continuity of suture material between the main suture length 158 and the loop 164. In addition, the transition from the suture end 160 to the loop 164 is smooth, thereby reducing the pulling friction associated with passing the loop through a soft tissue and/or aperture 304. As the loop 160 is pulled through a soft tissue or aperture, the loop 160 may collapse to a compact size approaching that of the main suture length in this aspect.

In various aspects, the diameter of each loop 164/166 may be configured to accommodate the suture exchange of one or more sutures 110 in one aspect. In this aspect, the loop diameter may be at least 1 mm. In other aspects, smaller or larger sutures may be used and the loop size diameter may decrease or increase accordingly. In additional aspects, the loop diameter may be at least 1 mm, at least 2 mm, at least 3 mm, at least 4 mm, at least 5 mm, at least 6 mm, at least 7 mm, at least 8 mm, at least 9 mm, at least 10 mm, or at least 20 mm. In other aspects, the diameter of each loop 164/166 may be configured to provide a suitable grip for a surgeon's hand or a surgical tool manipulated by a surgeon, or the loop diameter may be configured to simplify the act of loading suture ends 160/162 into the loop 164/166. In these other aspects, the diameter of each loop may be larger than the diameter that accommodates the suture exchange of one or more sutures 110.

In an additional aspect, at least a portion of the suture loops 164/166 and/or the main suture length 158 in close proximity to the suture loops 164/166 may be stiffened to facilitate the loading of additional sutures 110 into the suture loops 164/166, to facilitate the loading of the suture 110 by threading the suture loops 164/166 through an aperture 302 within a tissue anchor device 100, to provide tactile feedback to the surgeon, and any combination thereof. In one aspect, the loops 164/166 may be stiffened to maintain the loops 164/166 in a collapsed configuration, resulting in a smaller profile during use. In another aspect, the loops 164/166 may be stiffened to maintain the loops 164/166 in an opened configuration, thereby facilitating the loading of additional sutures 110 into the loops 164/166 and/or to provide a larger profile for a surgeon to grip during use. IN various aspects, the loops 164/166 may be stiffened using any suitable method including, but not limited to heat setting, application of stiffening coatings including, but not limited to a polymer or resin coating, and any combination thereof. However, it is to be noted that the stiffening loops 164/166 may retain the ability to collapse during passage through an aperture 304 or tissue without unduly high suture pulling forces that may disrupt the smooth pull of the sutures 110 during a surgical procedure associated with good tactile feedback to the surgeon.

II. Surgical Kit

Figure 40:
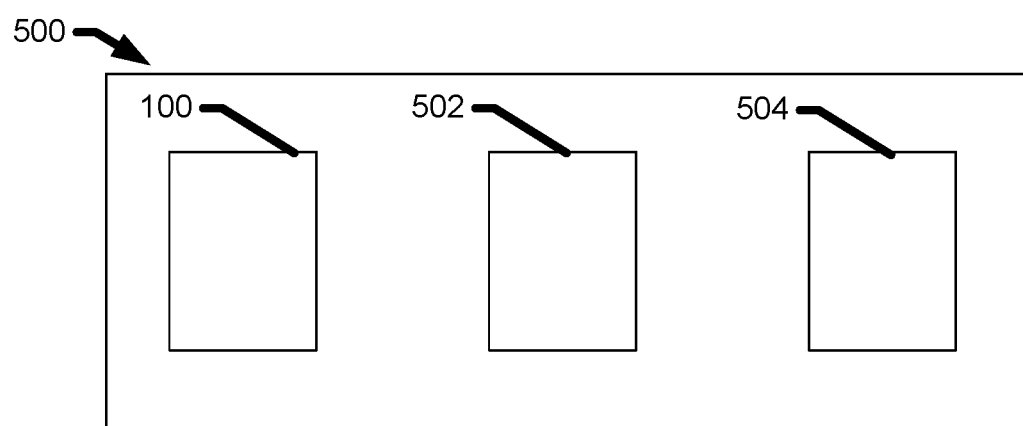
FIG. 40 is a block diagram summarizing elements of a surgical kit.

In an aspect, the tissue anchor device 100 described herein above may be included in a surgical kit for use by a surgeon in a surgical procedure. FIG. 40 is a block diagram summarizing the components of the surgical kit 500 in one aspect. The surgical kit 500 may include the tissue anchor device 100 described herein above, including at least one suture 110. The surgical kit may further provide instructions 502 and a delivery device 504.

In various aspects, the instructions 502 may be provided by any suitable means including, but not limited to: printed on packaging enclosing at least some of the surgical kit 500; enclosed within packaging enclosing at least some of the surgical kit 500; accompanying the surgical kit 500; published as an electronic communication such as an e-mail; published on an internet website; and any combination thereof. In various aspects, the instructions 502 may include information associated with the assembly of the tissue anchor device 100, information associated with implantation of the tissue anchor device 100, information associated with using the tissue anchor device 100 in an orthopedic surgical procedure, and any other information relevant to the assembly and use of the tissue anchor device 100. In this aspect, information associated with the assembly of the tissue anchor device 100 may include guidance for threading the at least one suture 110 through the aperture 302 of the suture exchange fitting 300, passing the first and second suture ends 160/162 proximally through the passage 116 of the body 102 and out the proximal opening 108, joining the distal tip 200 to the body 102 by inserting the proximal shaft 202 of the distal tip into the distal opening 138 of the body 102, and any combination thereof. In this aspect, information associated with the implantation of the tissue anchor device 100 in an orthopedic surgical procedure may include guidance for coupling the delivery tool 504 to the tissue anchor device 100 and delivering a torque to drive the tissue anchor device 100 into the bone tissue. In this aspect, information associated with using the tissue anchor device 100 in an orthopedic surgical procedure may include guidance for exchanging one or more sutures 110 between one or more apertures 302 associated with different tissue anchor devices 100 to enable various surgical procedures including, but not limited to assembling and securing one or more suture patterns suitable for attaching a soft tissue to a bone tissue.

The delivery device 504 may be any driver system suitable for orthopedic fasteners without limitation. Non-limiting examples of suitable delivery devices 504 include: single-slot driver systems, star-shaped driver systems, cruciform driver systems, Phillips driver systems, hexagonal driver systems and any other suitable driver system.

III. Method of Anchoring Soft Tissue

In various aspects, one or more tissue anchor devices 100 may be used to anchor a soft tissue to a bone. The one or more tissue anchor devices 100 may be implanted in a bone and linked to one another after implantation via one or more sutures without the use of a knot or other inter-anchor fixation, thereby establishing a contiguous inter-anchor suture ending at a pair of free suture ends. Each suture end is attached to a first anchor device 100 and a last anchor device 100'. The free suture ends may be used for any generally accepted final repair fixation practice, including, but not limited to, anchor fixation, knotless anchor fixation, knot fixation, or linkage to additional anchor devices 100".

In one aspect, an orthopedic repair including fixation of a soft tissue to a bone may use at least two tissue anchor devices 100 and at least one suture 110. The suture 110 may be passed through the at least two at least two tissue anchor devices 100 using a suture exchange method described in detail herein below. Using one or more suture exchanges, a single suture 110 may form a single continuous span or linkage of suture between the at least two tissue anchor devices 100. The single continuous suture span may end in two free ends that may be used to implement a final fixation or knot in accordance with standard surgical suture fixation practices and products.

In this aspect, the use of a single suture provides at least several benefits over existing knotted linkage techniques. The use of a single suture and at least two tissue anchor devices 100 as a linkage enables superior adhesion of the soft tissue to the bone compared to a knotted linkage. The use of the at least two tissue anchor devices 100 provides the capability to use a "running stich" of suture 110 for a faster and simplified repair. Because the suture 110 is not fixed at each anchor 100, the suture 110 is capable of sliding to a limited degree between anchor points, thereby efficiently distributing the compression load over the soft tissue. Using this method, the suture tension and stress may also be distributed across multiple anchors 100, thereby reducing the likelihood of developing single failure points in which all tension and stress may be isolated to a single anchor. The use of this method further enables the implementation of at least several suture patterns as needed, thereby enhancing the options available to the surgeon and the resulting effectiveness of the surgical procedure.

Figure 41:
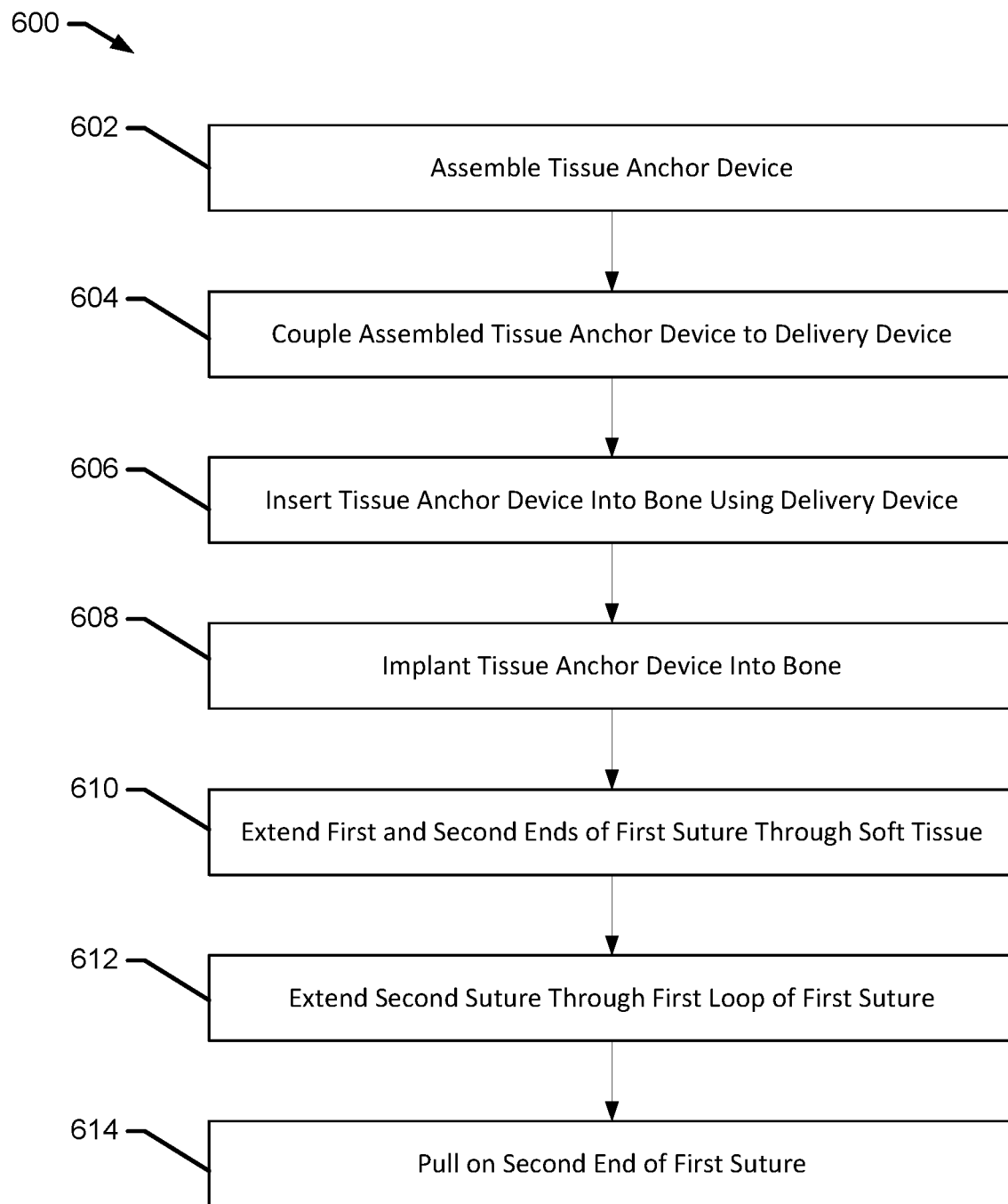
FIG. 41 is a flow chart summarizing a method of attaching a soft tissue to a bone using at least one tissue anchor device.

FIG. 41 is a flow chart summarizing a method of anchoring a soft tissue to a bone using the tissue anchor device 100 described herein above in one aspect. The method may include assembling the tissue anchor device 100 at step 602. In one aspect, the tissue anchor device 100 may be assembled by causing the distal tip 200 that is loaded with a first suture 110A to be received in the distal opening 138 of the body 102 such that the first suture 170 extends through the passage 116 of the body 102 and out the proximal opening 108 such that the first and second ends 160/162 of the first suture 170 extend proximally from the proximal opening 108.

Referring again to FIG. 41, the method may further include attaching a delivery device 504 to the tissue anchor device 100 at step 604. In one aspect, the first suture 170 may be extended through a lumen of the delivery device 504 such that the first and second ends 160/162 of the first suture 170 extend proximally from a proximal end of the delivery device 504 and a distal end of the delivery device 504 is coupled with a proximal end 104 of the body 102, the lumen extending between a distal end of the delivery device 504 and the proximal end of the delivery device 504. The coupled delivery device 504 may be used to torque the first tissue anchor into the bone at step 606. In one aspect, the delivery device 504 may apply a torque to the body 102 via the distal end of the delivery device 504 coupled to the tool fitting 134 formed within the proximal opening 108 as described herein above.

Referring again to FIG. 41, the tissue anchor device 100 may be implanted into the bone at step 608. In one aspect, a bore may be preformed within the bone prior to implanting the tissue anchor device 100. In another aspect, if the external thread 114 of the body 102 includes a self-tapping feature, the tissue anchor device 100 may be inserted without need to form a bore beforehand. In one aspect, the tissue anchor device 100 may be implanted by advancing the body 102 and distal tip 200 into the bone until the proximal end 104 of the body 102 is essentially level with the exposed surface of the bone. In another aspect, if the suture exchange fitting 300 is situated proximally to the proximal end 104 of the body 102, the body and the distal tip 200 may be advanced into the bone until the proximal end 104 of the body 102 is distal relative to the exposed surface of the bone.

The method 600 may further include extending the first and second ends 160/162 of the first suture 170 through the soft tissue at step 610. The soft tissue may be any soft tissue to be reattached to a bone including, but not limited to, a tendon and/or a ligament. In an aspect, the first and second ends 160/162 of the first suture 170 may be extended through one or more layers, each layer including a soft tissue to be attached to the bone. A second suture 172 may be extended through a first loop 164 defined at the first end 160 of the first suture 170. FIG. 37 is an illustrating showing the second suture 172 extended through the first loop 164 of the first suture 170. As illustrated in FIG. 37, the first end 160' of the second suture 172 may now extend proximally from a second tissue anchor device 100' and the second end 162' of the second suture 172 may extend proximally through a soft tissue 402.

In various aspects, variations of the method 600 may be used to implement a variety of suture patterns and techniques as needed to enhance the linkage between the soft tissue 402 and the bone 404. Non-limiting examples of suture patterns and techniques include: a single suture box stitch pattern, a lateral medial bridge stitch pattern using a knotless single suture, a medial bridge, inter-implant mattress stitch pattern, a train track, a parallel horizontal repair using 2 anchors, and a medial dam suture pattern to block synovial fluid infiltration. Additional description of the suture patterns and techniques are provided herein below.

Figures 42A, 42B:
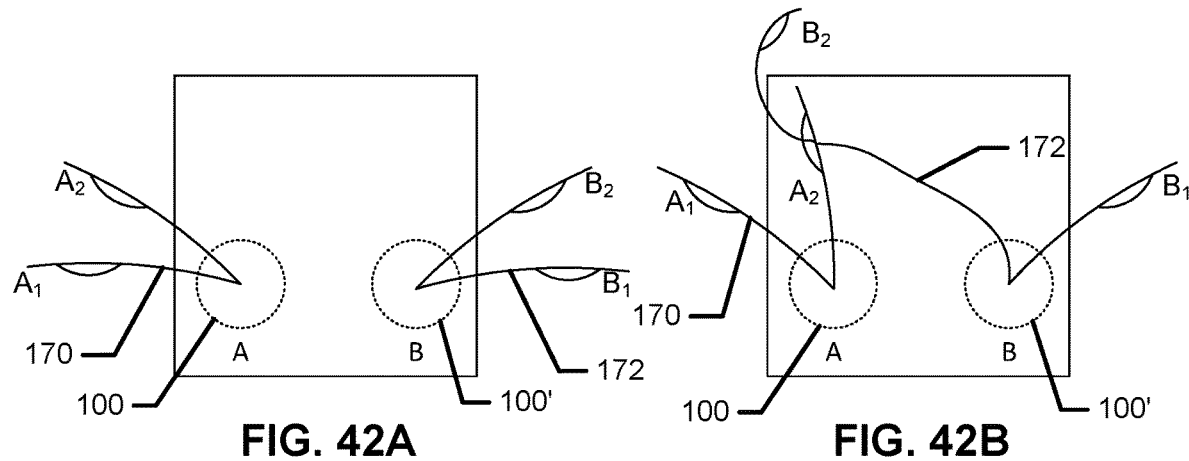
FIG. 42A, FIG. 42B, FIG. 42C, FIG. 42D, FIG. 42E, and FIG. 42F are schematic diagrams illustrating a single row repair using at least one tissue anchor device.
Figures 42C, 42D:
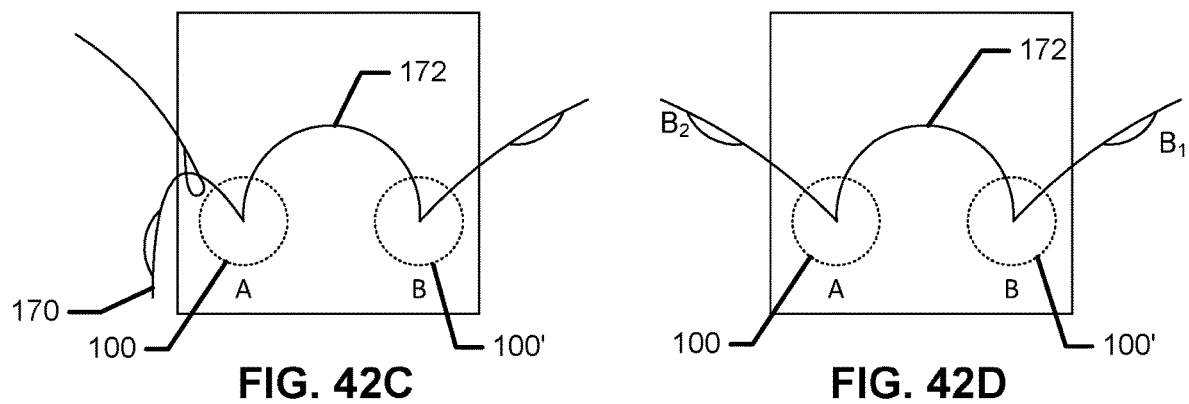
Figures 42E, 42F:
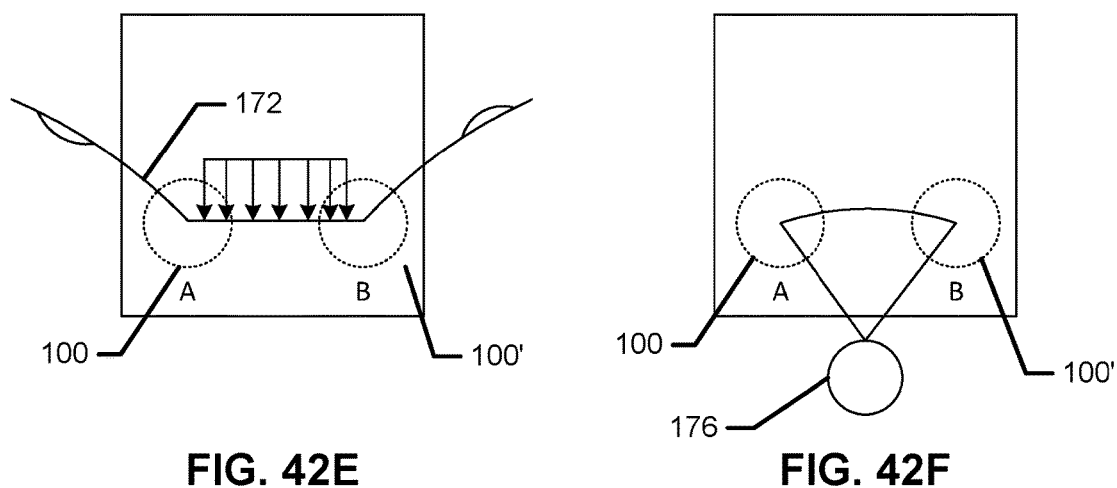

FIG. 42A, FIG. 42B, FIG. 42C, FIG. 42D, FIG. 42E, and FIG. 42F illustrate schematically a single row repair accomplished using an implanted first anchor 100 with a first suture 170 and an implanted second anchor 100' with a second suture 172. The first and second anchors 170/172 may be implanted as illustrated in FIG. 42A. Referring to FIG. 42B, a suture exchange may be started by threading the second end B2 of the second suture 172 through the second end A2 of the first suture 170. As illustrated in FIG. 42C, the exchange of the second suture 172 into the first anchor 100 is completed by pulling on the first end A1 of the first suture 170. The first suture 170 may then be removed from the second suture 172, as illustrated in FIG. 42D. The ends B1/B2 of the second suture 172 may then be tensioned as illustrated in FIG. 42E. The ends B1/B2 of the second suture 172 may then be joined using a knot or a knotless joiner 176 as illustrated in FIG. 42E.

Figure 43A:
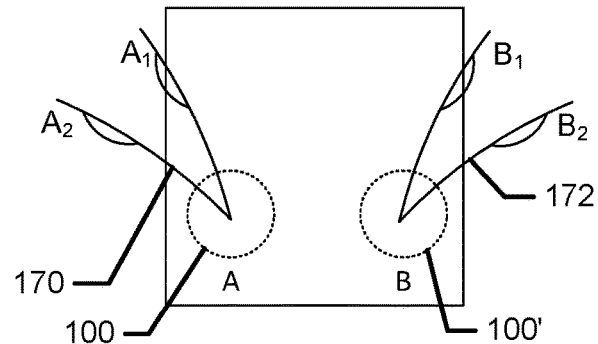
FIG. 43A, FIG. 43B, FIG. 43C, FIG. 43D, FIG. 43E, FIG. 43F, and FIG. 43G are schematic diagrams illustrating a wide single row repair using at least one tissue anchor device.
Figure 43B:
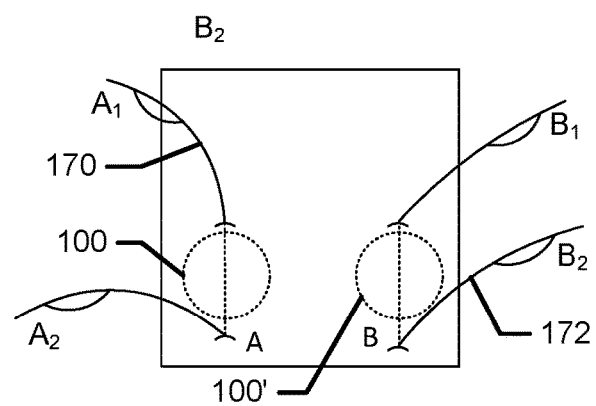
Figure 43C:
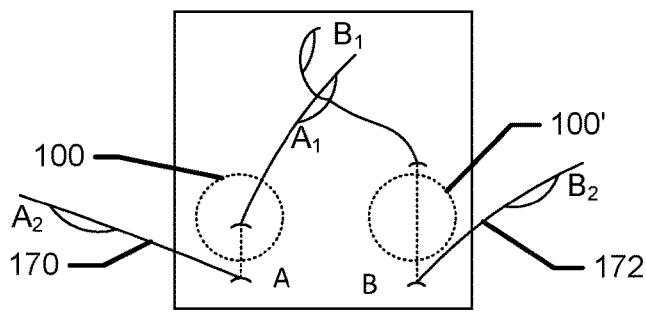
Figure 43D:
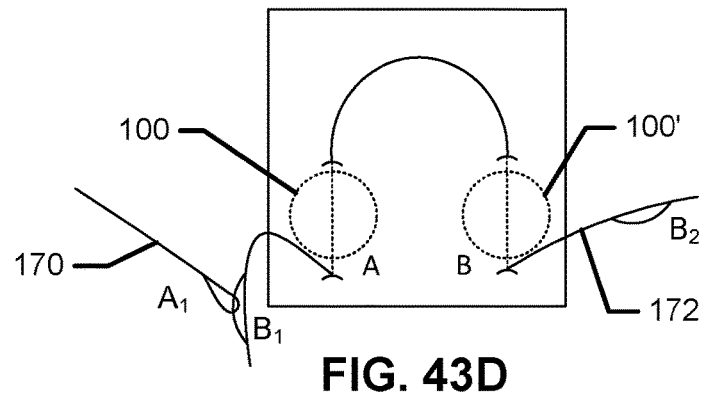
Figure 43E:
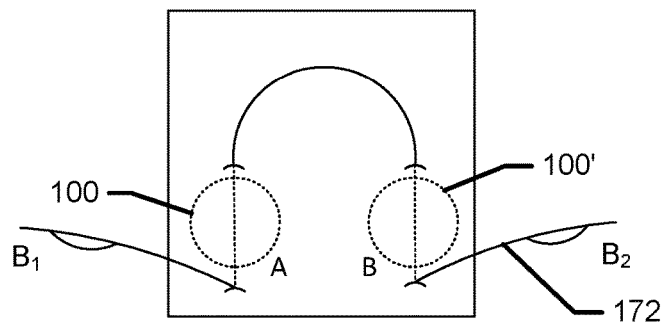
Figure 43F:
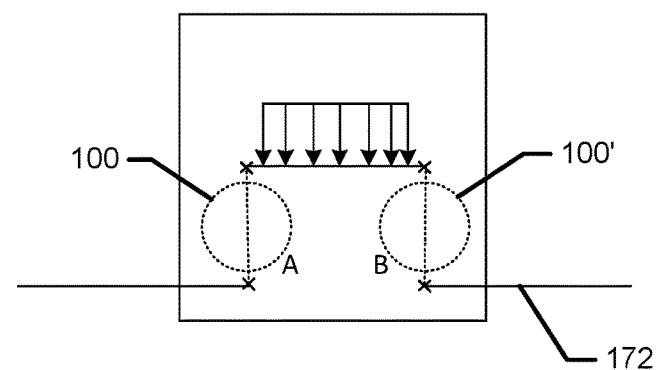
Figure 43G:
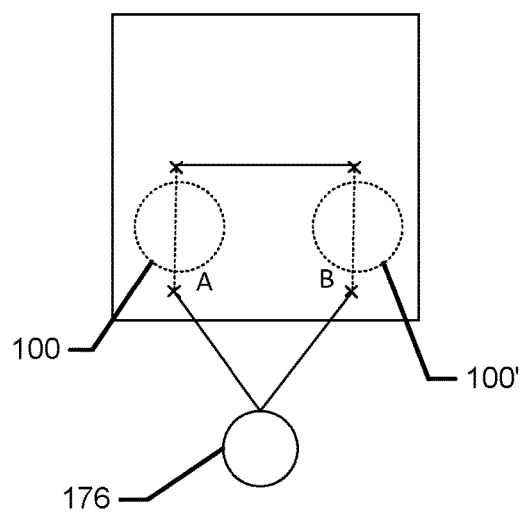

FIG. 43A, FIG. 43B, FIG. 43C, FIG. 43D, FIG. 43E, FIG. 43F, and FIG. 43G illustrate schematically a wide single row repair accomplished using an implanted first anchor 100 with a first suture 170 and an implanted second anchor 100' with a second suture 172. The first and second anchors 170/172 may be implanted as illustrated in FIG. 43A. Referring to FIG. 43B, the suture ends A1/A2 and B1/B2 may be pulled through the soft tissue layer at widely separated locations. Referring to FIG. 43C, a suture exchange may be started by threading the second end B2 of the second suture 172 through the first end A1 of the first suture 170. As illustrated in FIG. 43D, the exchange of the second suture 172 into the first anchor 100 is completed by pulling on the first end A2 of the first suture 170. The second suture may be pulled through both widely separated locations in the soft tissue near the first anchor 170 as illustrated in FIG. 43D. The first suture 170 may then be removed from the second suture 172 to complete the suture exchange, as illustrated in FIG. 43E. The ends B1/B2 of the second suture 172 may then be tensioned as illustrated in FIG. 43F. The ends B1/B2 of the second suture 172 may then be joined using a knot or a knotless joiner 176 as illustrated in FIG. 43G.

Figure 44A:
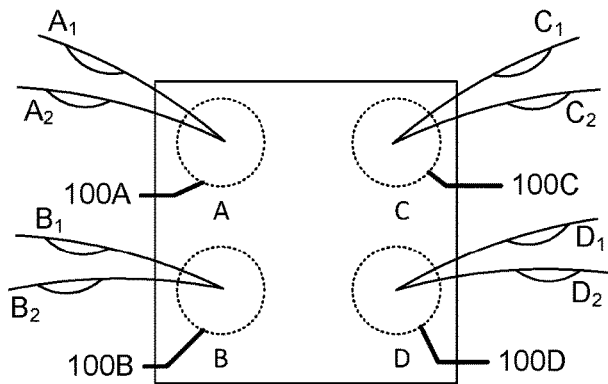
FIG. 44A, FIG. 44B, FIG. 44C, FIG. 44D, FIG. 44E, FIG. 44F, and FIG. 44G are schematic diagrams illustrating a double row repair using at least one single-loaded tissue anchor device.
Figure 44B:
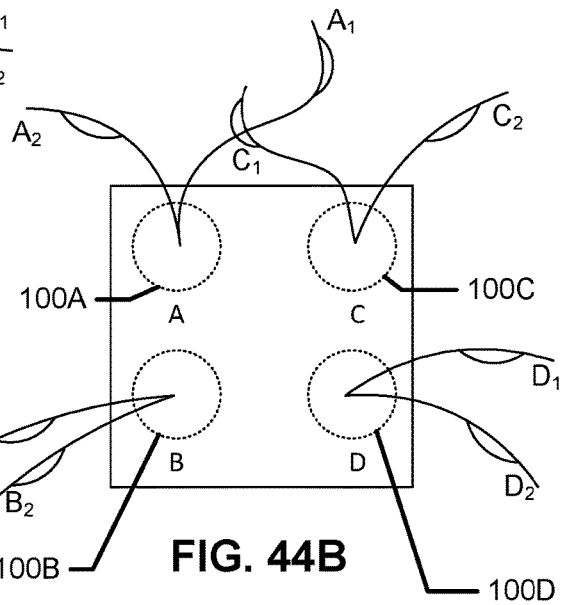
Figure 44C:
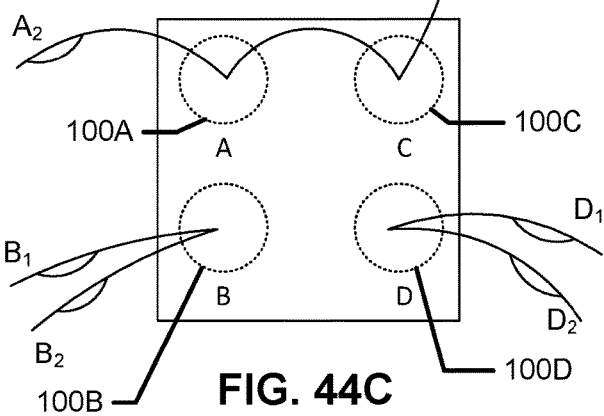
Figure 44D:
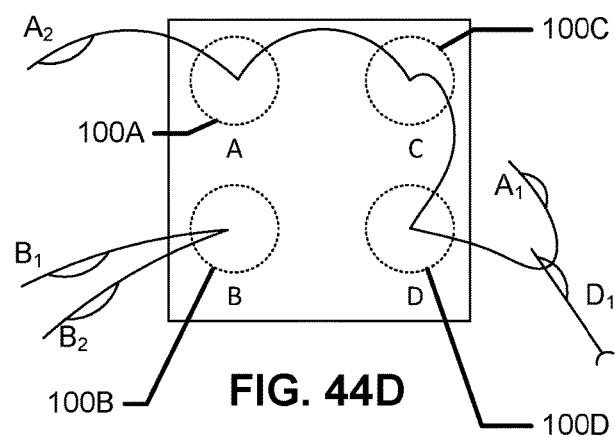
Figure 44E:
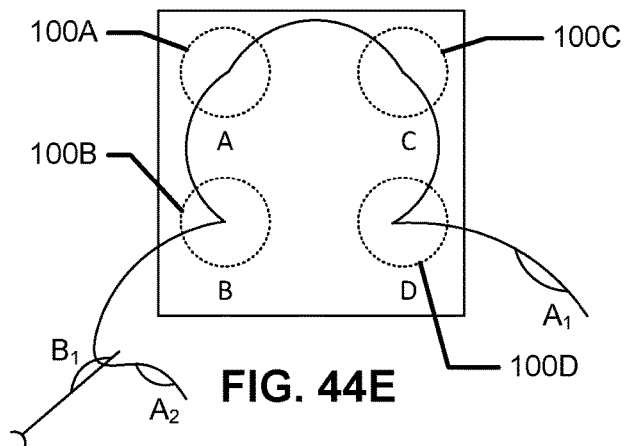
Figure 44F:
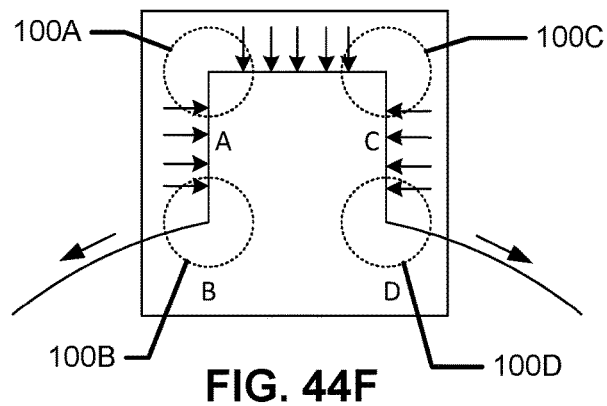
Figure 44G:
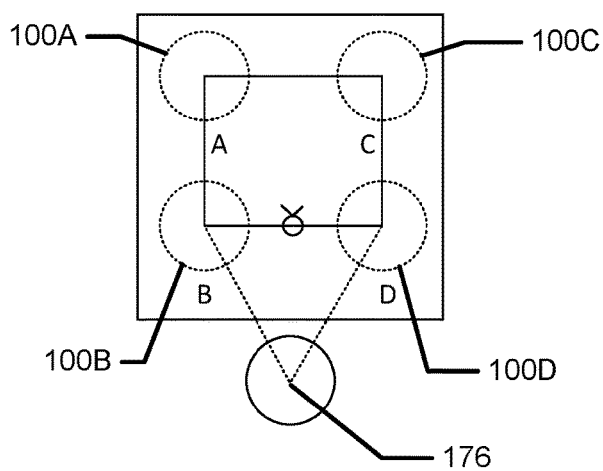

FIG. 44A, FIG. 44B, FIG. 44C, FIG. 44D, FIG. 44E, FIG. 44F, and FIG. 44G illustrate schematically a double row repair accomplished using implanted single-loaded anchors 100A, 100B, 100C, and 100D. The anchors 100A, 100B, 100C, and 100D may be implanted in a square pattern as illustrated in FIG. 44A and both ends of each suture may be pulled through the soft tissue over each corresponding anchor. Referring to FIG. 44B, a suture exchange may be started by threading the first end A1 through the first end C1 and pulling on the second end C2. As illustrated in FIG. 44C, the exchange of suture end A1 through anchor 110C may be completed by pulling on the suture end C2. Similar suture exchanges may be further accomplished to pull suture end A2 through anchor 100B as illustrated in FIG. 4D and suture end A1 through anchor 100D, as illustrated in FIG. 44E. The first suture 170 may then be removed from the second suture 172 to complete the suture exchange, as illustrated in FIG. 44E. The ends A1/A2 may then be tensioned as illustrated in FIG. 44F. The ends A1/A2 may then be joined using a knot or a knotless joiner 176 as illustrated in FIG. 44G.

Figure 45A:
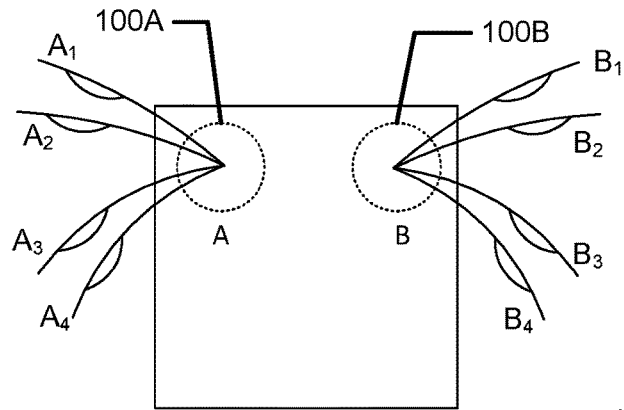
FIG. 45A, FIG. 45B, FIG. 45C, FIG. 45D, FIG. 45E, FIG. 45F, and FIG. 45G are schematic diagrams illustrating a double row repair using at least one double-loaded tissue anchor device.
Figure 45B:
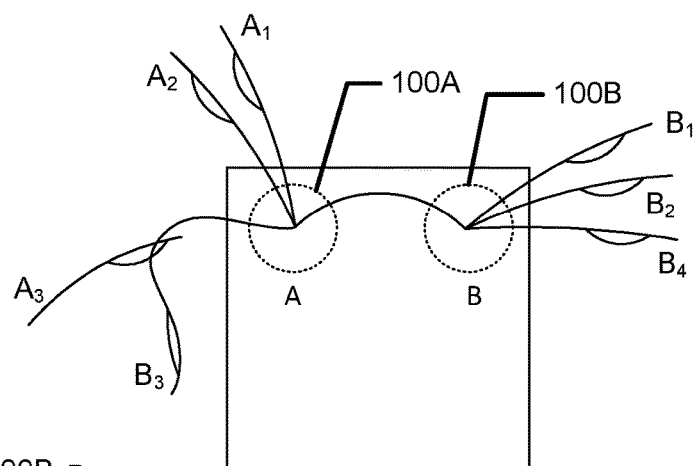
Figure 45C:
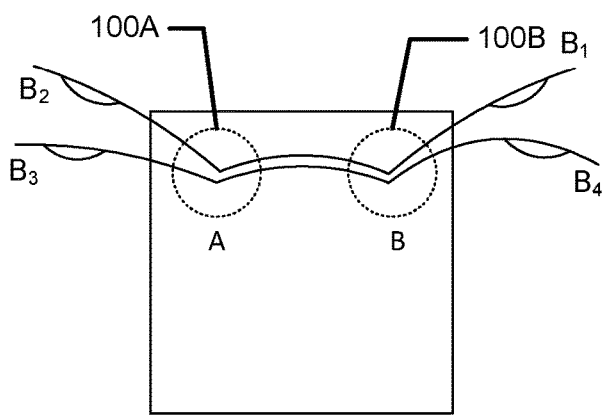
Figure 45D:
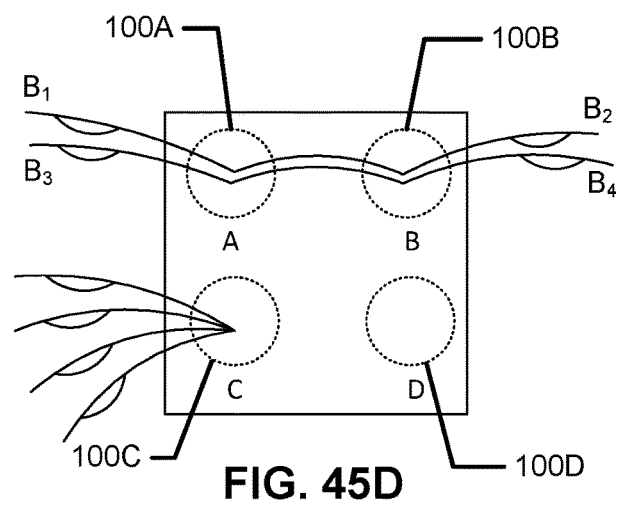
Figure 45E:
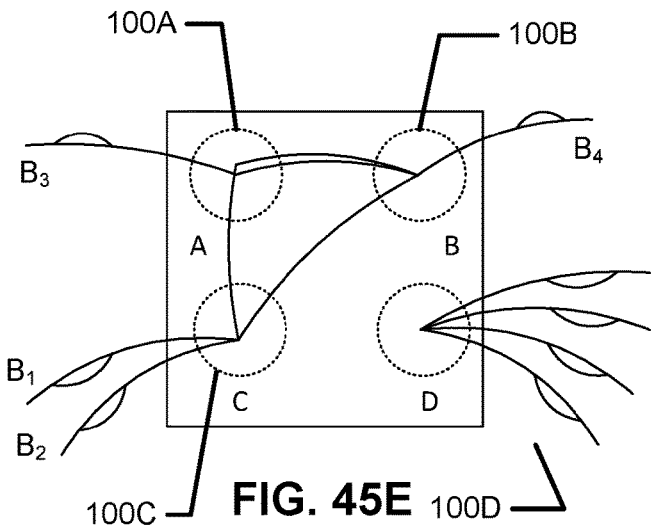
Figure 45F:
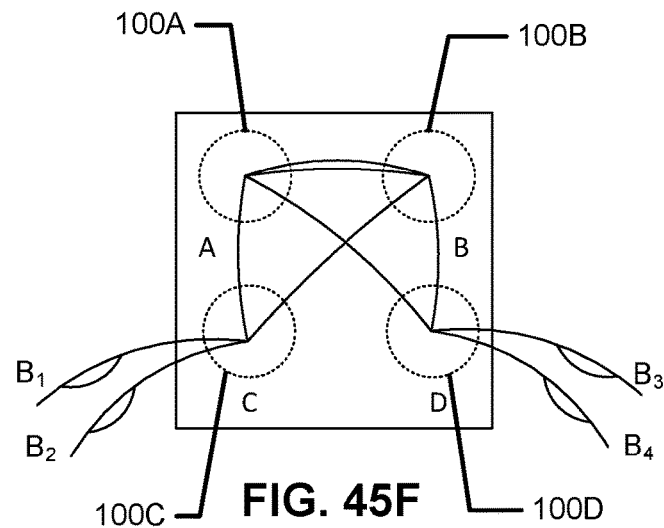
Figure 45G:
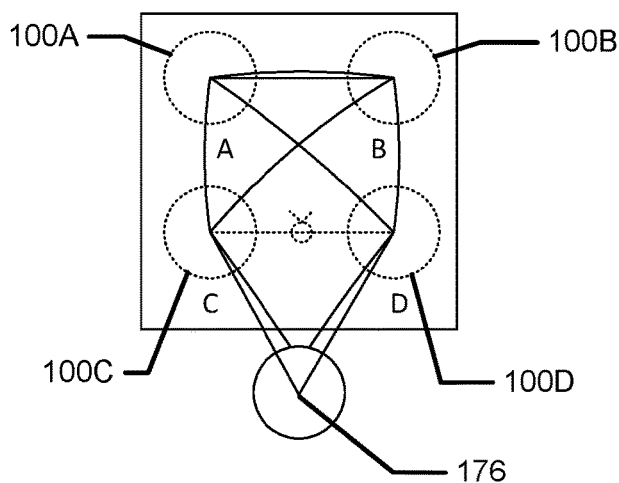

FIG. 45A, FIG. 45B, FIG. 45C, FIG. 45D, FIG. 45E, FIG. 45F, and FIG. 45G illustrate schematically a double row repair accomplished using implanted double-loaded anchors 100A, 100B, 100C, and 100D. The anchors 100A, 100B may be implanted as illustrated in FIG. 45A and both ends of each suture may be pulled through the soft tissue over each corresponding anchor. Referring to FIG. 45B, a suture exchange may be accomplished by threading the suture end B3 through the suture end A3 and pulling on the opposite suture end A4. Referring to FIG. 45C, a suture exchange may be accomplished by threading the suture end B1 through the suture end A2 and pulling on the opposite suture end A1. As illustrated in FIG. 45D, the additional double-loaded anchors 100C and 100D may be implanted, resulting in a square anchor pattern. Referring to FIG. 45E, the exchange of suture ends B1 and B2 through anchor 110C may be completed similarly using the two loaded sutures of anchor 100C. Referring to FIG. 45F, the exchange of suture ends B3 and B4 through anchor 110D may be completed similarly using the two loaded sutures of anchor 100D. The ends A1, A2, B1, and B2 may then be tensioned and joined using a knot or a knotless joiner 176 as illustrated in FIG. 45G.

Figure 46E:
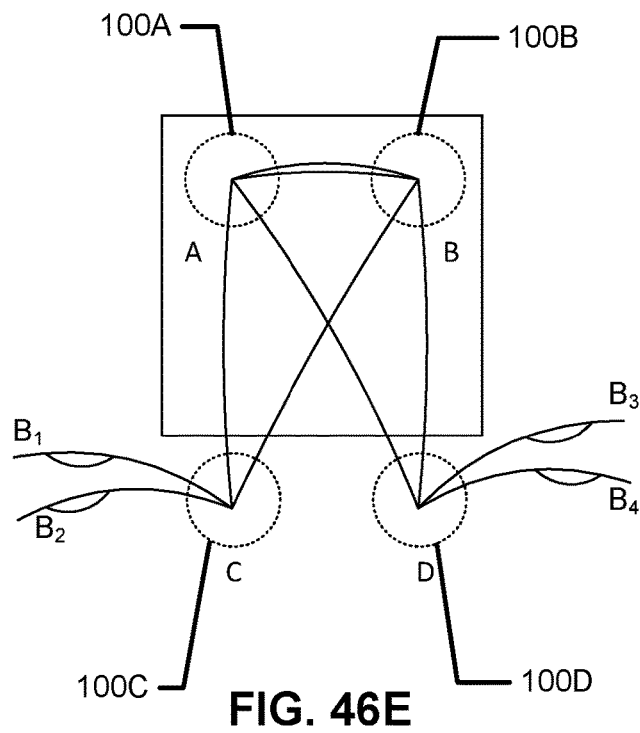
Figure 46F:
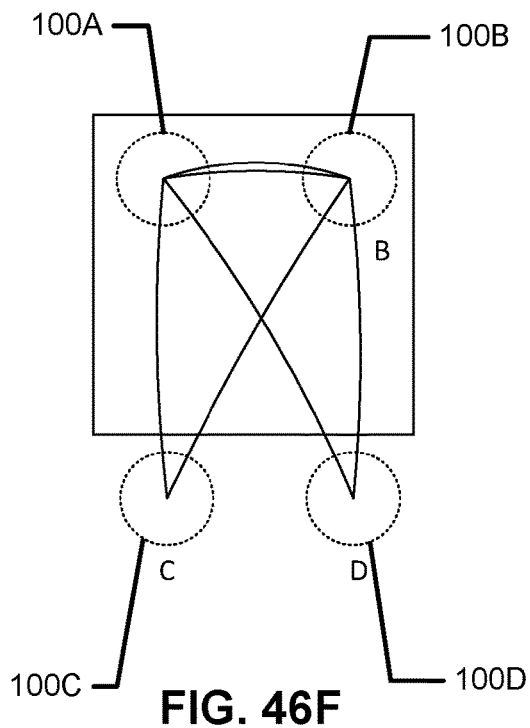
Figure 46G:
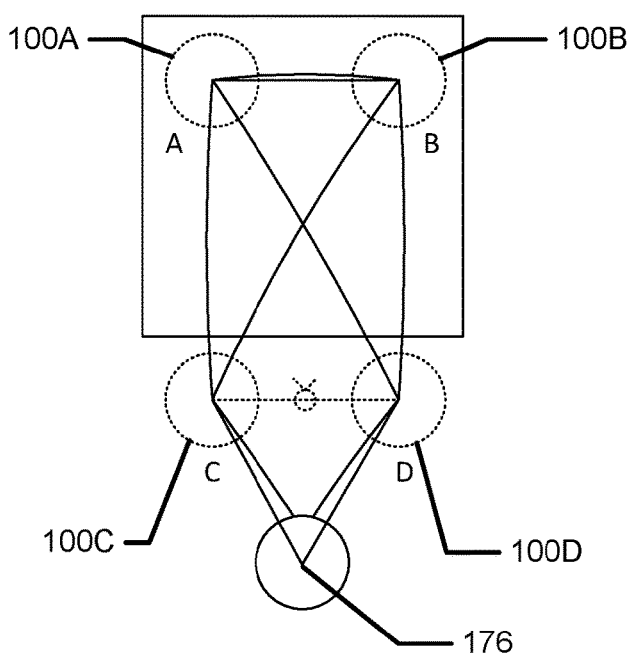

FIG. 46A, FIG. 46B, FIG. 46C, FIG. 46D, FIG. 46E, FIG. 46F, and FIG. 46G illustrate schematically a transosseous repair accomplished using implanted double-loaded anchors 100A, 100B, 100C, and 100D. The anchors 100A, 100B may be implanted as illustrated in FIG. 46A and both ends of each suture may be pulled through the soft tissue situated over each corresponding anchor. Referring to FIG. 46B, a suture exchange may be accomplished by threading the suture end B3 through the suture end A3 and pulling on the opposite suture end A4. Referring to FIG. 46C, a suture exchange may be accomplished by threading the suture end B1 through the suture end A2 and pulling on the opposite suture end A1. As illustrated in FIG. 46D, the additional double-loaded anchors 100C and 100D may be implanted in a different bone or at an offset location not covered by the soft tissue layer, resulting in a square anchor pattern. Referring to FIG. 46E, the exchange of suture ends B1 and B2 through anchor 110C may be completed similarly using the two loaded sutures of anchor 100C, and the exchange of suture ends B3 and B4 through anchor 110D may be completed similarly using the two loaded sutures of anchor 100D. Referring to FIG. 46F, the suture ends A1, A2, B1, and B2 may be tensioned and retained knotlessly within corresponding anchors 100C and 100D. Alternatively, the ends A1, A2, B1, and B2 may then be tensioned and joined using a knot or a knotless joiner 176 as illustrated in FIG. 46G.

FIG. 47A and FIG. 47B are schematic illustrations of additional arrangements of sutures and anchors associated with double row repairs illustrated in FIG. 44G and FIG. 45G, respectively. FIG. 47A illustrates a double-row repair accomplished using implanted single-loaded anchors 100A, 100B, 100C and 100D. As illustrated in FIG. 47A, the ends of the single continuous suture 170 may be crossed over and secured within a pair of implanted knotless anchors 110E and 100F. FIG. 47B illustrates a double-row repair accomplished using implanted double-loaded anchors 100A, 100B, 100C and 100D. As illustrated in FIG. 47B, the ends of a first single continuous suture 170 may be crossed over and secured within a pair of implanted knotless anchors 110E and 100F, and the ends of a second single continuous suture 172 may be secured within the pair of implanted knotless anchors 110E and 100F without crossing over.

Figure 48A:
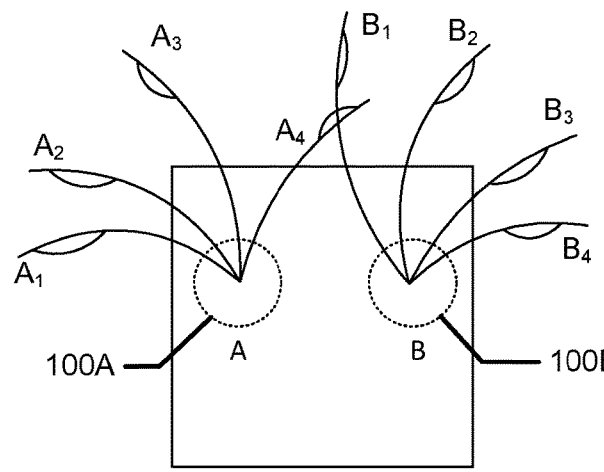
FIG. 48A, FIG. 48B, FIG. 48C, FIG. 48D, FIG. 48E, and FIG. 48F are schematic diagrams illustrating alternative double row repairs using at least one single-loaded or double-loaded tissue anchor device.
Figure 48B:
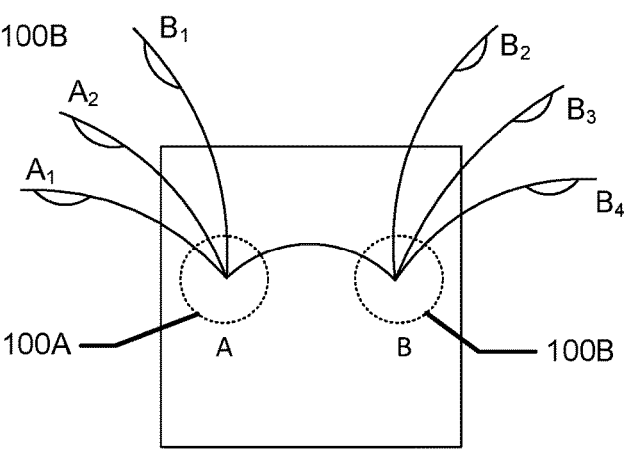
Figure 48C:
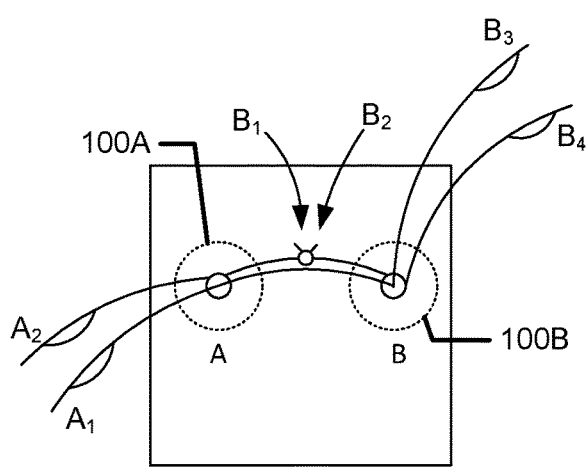
Figure 48D:
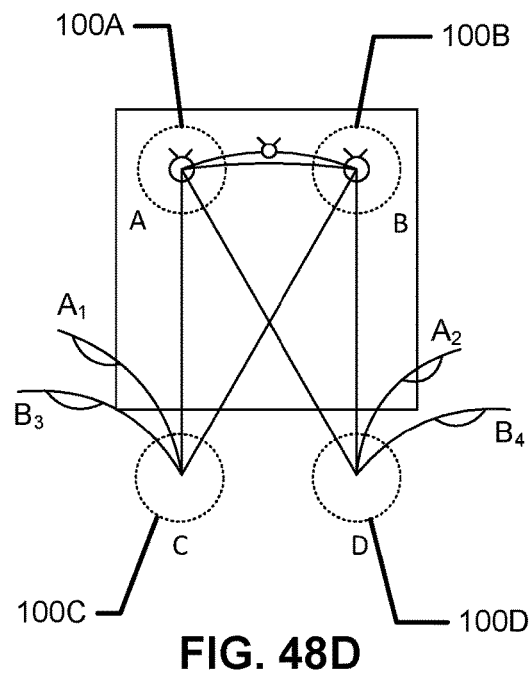

FIG. 48A, FIG. 48B, FIG. 48C, and FIG. 48D illustrate schematically a traditional bridged repair accomplished using implanted double-loaded anchors 100A, 100B, 100C, and 100D. The anchors 100A, 100B may be implanted as illustrated in FIG. 48A and both ends of each suture may be pulled through the soft tissue over each corresponding anchor. Referring to FIG. 48B, a suture exchange may be accomplished by threading the suture end B1 through the suture end A3 and pulling on the opposite suture end A4. Referring to FIG. 48C, suture ends B1 and B2 may be tensioned and joined with a knot. As illustrated in FIG. 48D, the additional double-loaded anchors 100C and 100D may be implanted, resulting in a square anchor pattern. Referring again to FIG. 48D, the exchange of suture ends A1 and B3 through anchor 110C and the exchange of suture ends A2 and B4 through anchor 110D may be completed similarly using the pairs of sutures loaded on anchors 100C and 100D.

Figure 48F:
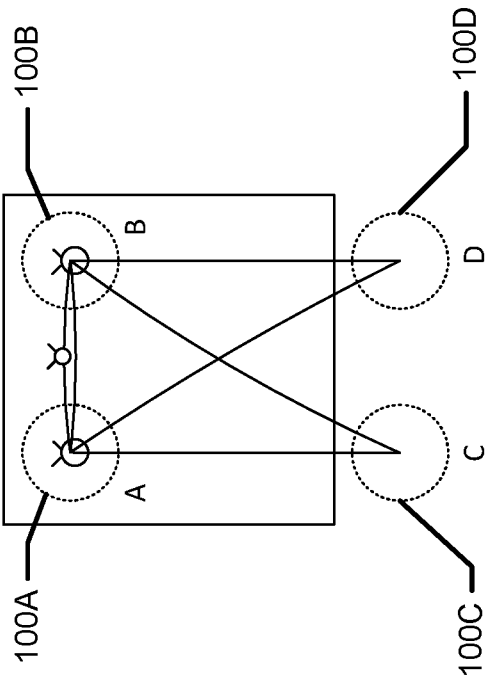
Figure 48E:
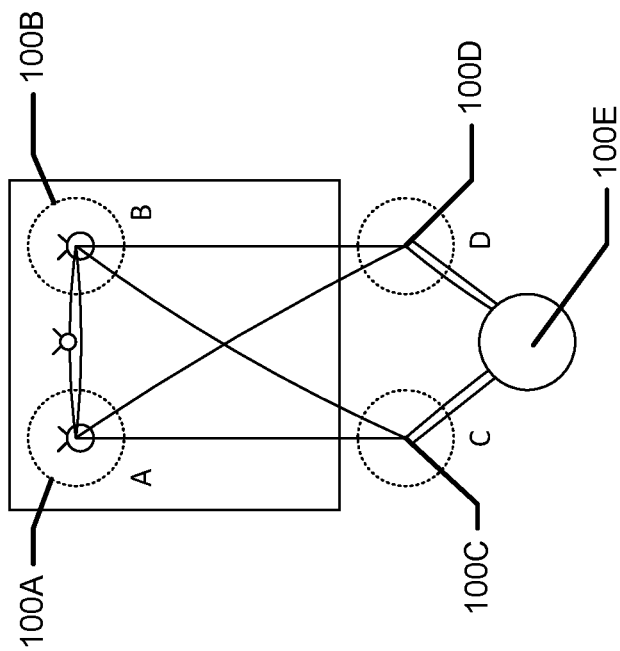

Referring to FIG. 48E, the ends A1, A2, B3, and B4 may be tensioned and secured using a single knotless anchor 100E. Referring to FIG. 48F, the suture ends A1 and B3 may be secured using knotless anchor 100C, and suture ends A2 and B4 may be tensioned and secured using knotless anchor 100D.

Figure 49A:
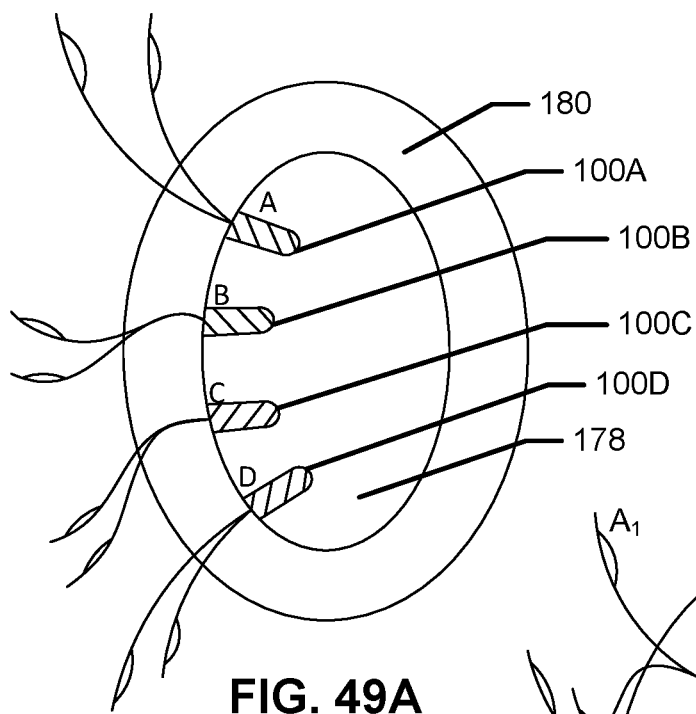
FIG. 49A, FIG. 49B, FIG. 49C, FIG. 49D, FIG. 49E, FIG. 49F, FIG. 49G, FIG. 49H, FIG. 49I, and FIG. 49J are schematic diagrams illustrating a labrum repair using at least one single-loaded or double-loaded tissue anchor device.
Figure 49B:
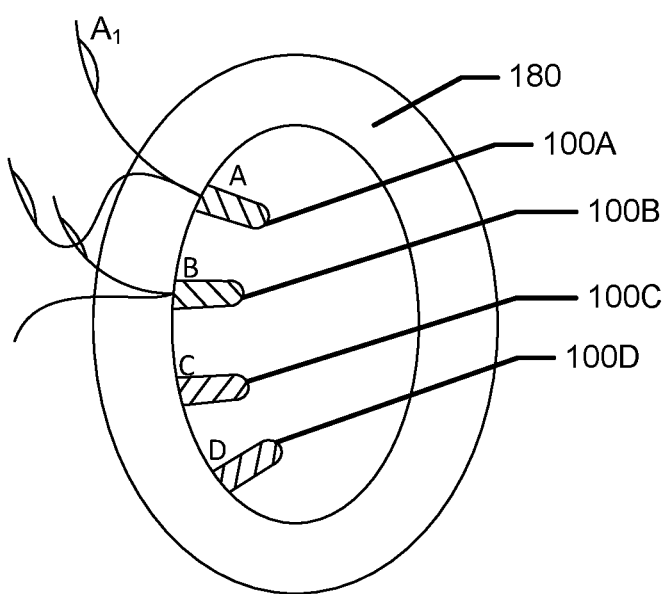
Figure 49C:
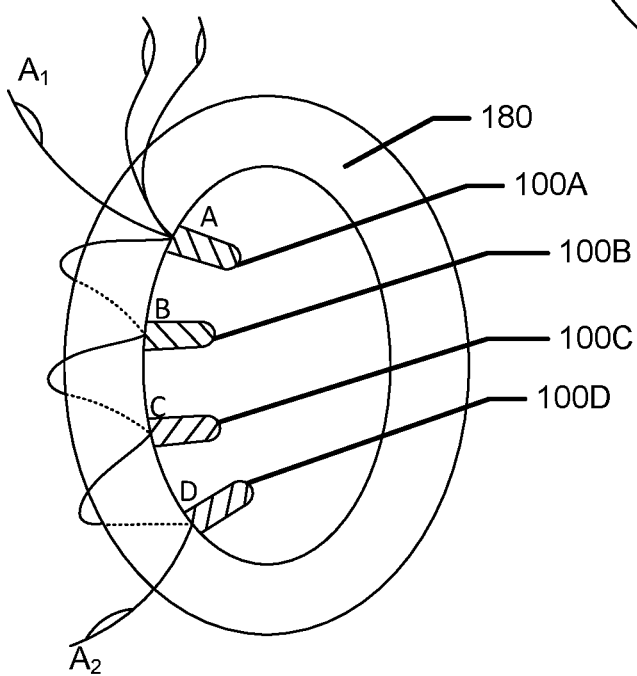
Figure 49D:
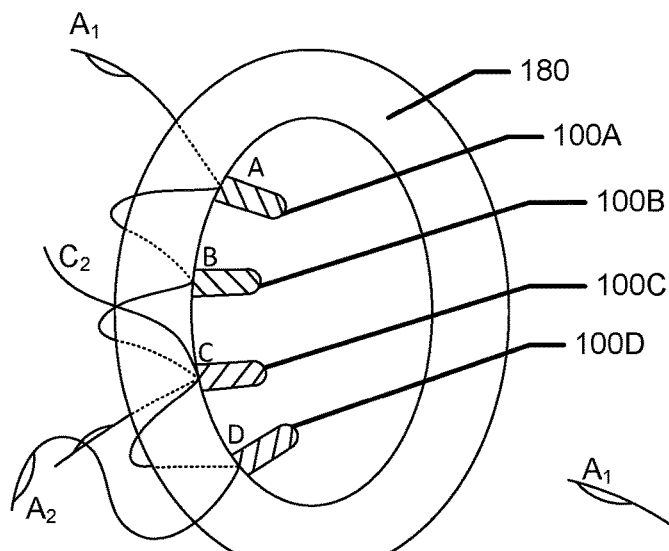
Figure 49E:
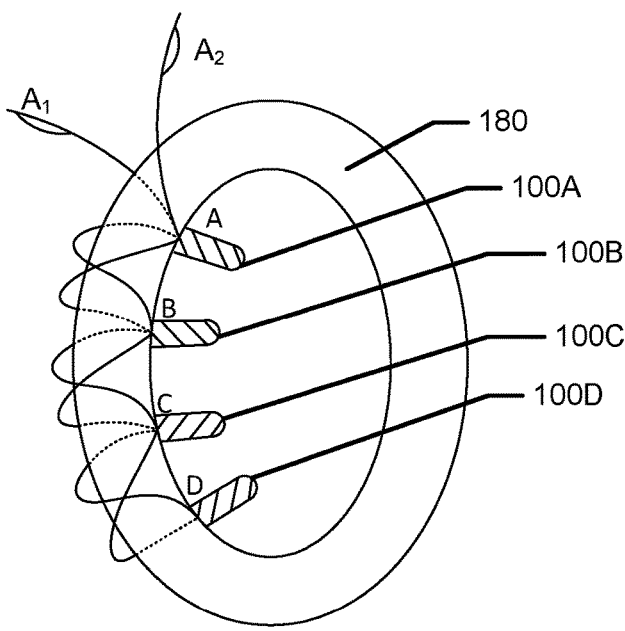
Figure 49F:
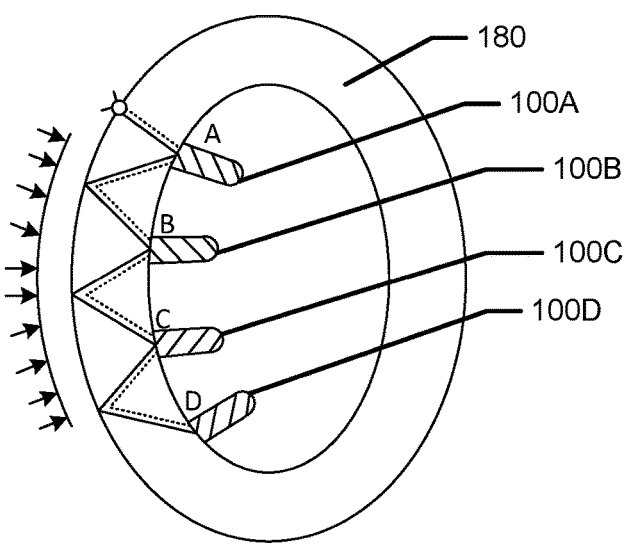
Figure 49H:
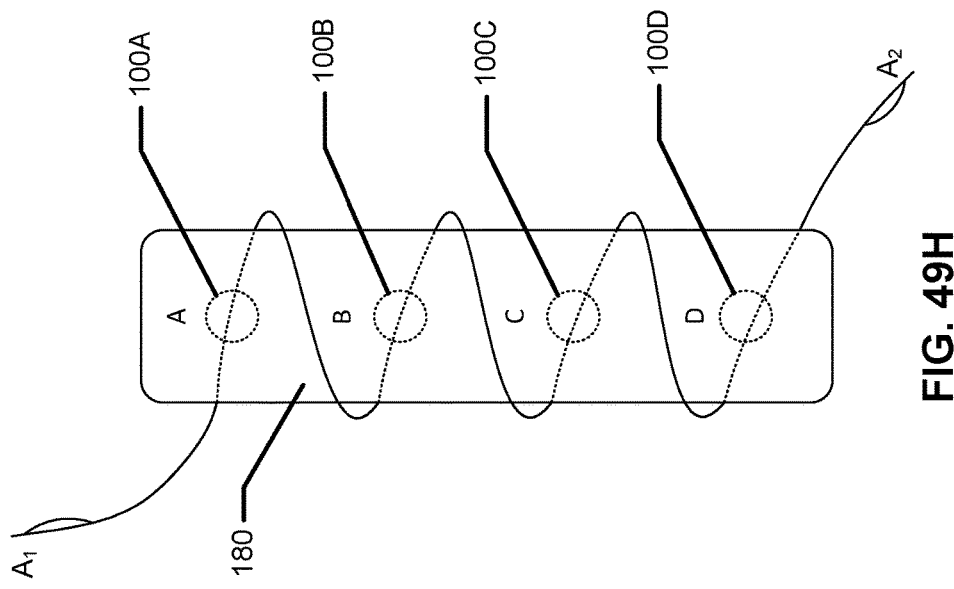
Figure 49G:
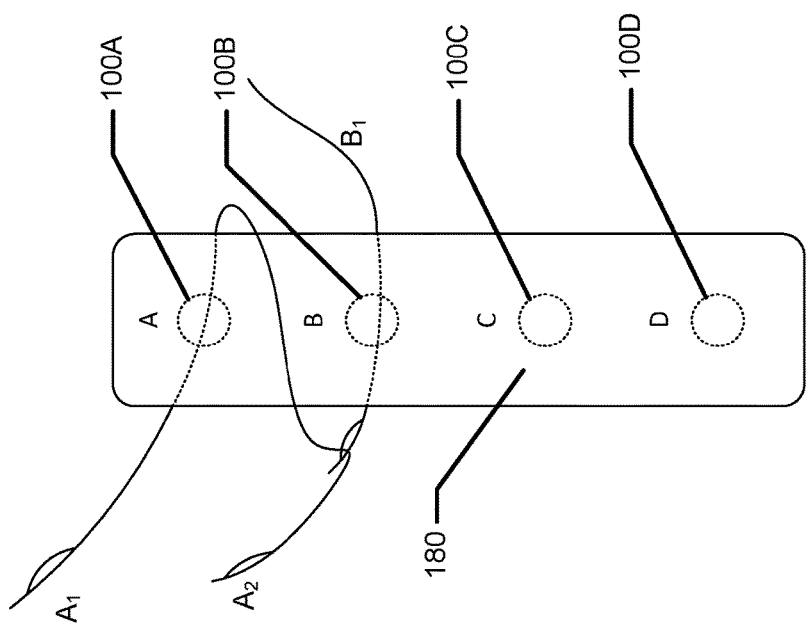
Figure 49J:
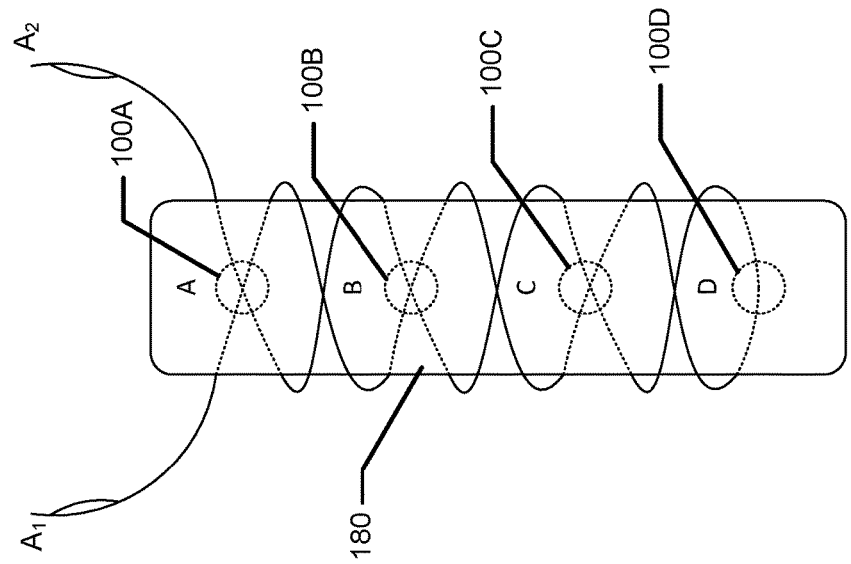
Figure 49I:
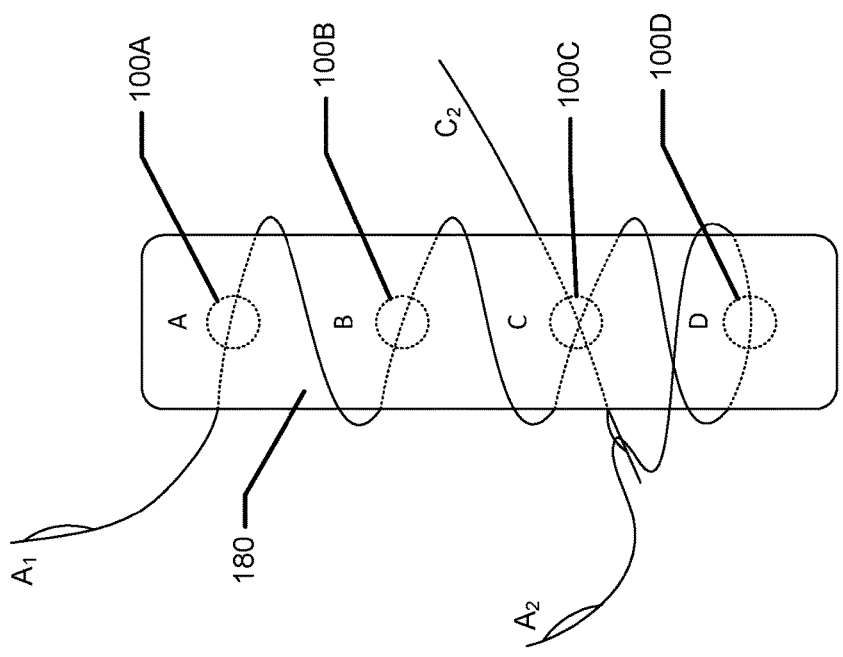

FIG. 49A, FIG. 49B, FIG. 49C, FIG. 49D, FIG. 49E, FIG. 49F, FIG. 49G, FIG. 49H, FIG. 49I, and FIG. 49J illustrate schematically repair of a labrum tear accomplished using implanted double-loaded anchors 100A, 100B, 100C, and 100D. The anchors 100A, 100B, 100C, and 100D may be implanted within a glenoid bone 180 as illustrated in FIG. 49A, and the opposite ends of each suture may be situated at opposite sides of the overlying labrum tissue 178. Referring to FIGS. 49B and 49G, a suture exchange of suture end A2 between anchor 100A and anchor 100B may be accomplished using one of the two sutures threaded through anchor 100B. Referring to FIG. 49C and FIG. 49H, the suture end A2 may be threaded successively through anchors 100B, 100C, and 100D in a spiral pattern using one of the loaded sutures in each corresponding anchor. As illustrated in FIG. 49H, the suture end A2 passes over the labrum 180 between successive anchors and passes under the labrum 180 as the suture end A2 passes through each successive anchor. As illustrated in FIG. 49D and FIG. 49I, the suture end A2 may be exchanged from anchor 100D to anchor 100C using the remaining loaded suture in anchor 100C. Referring to FIG. 49E and FIG. 49J, the suture end A2 may be threaded successively through anchors 100B, 100C, and 100D in a spiral pattern using the remaining loaded suture in each corresponding anchor. As illustrated in FIG. 49J, the suture end A2 passes over the labrum 180 between successive anchors and passes under the labrum 180 as the suture end A2 passes through each successive anchor; the direction of crossing is opposite to the direction illustrated in FIG. 49H, resulting in a crossed suture pattern around the labrum 180. Referring to FIG. 49F, the suture ends A1 and A2 may be tensioned and secured with a knot or knotless joiner.

The foregoing merely illustrates the principles of the invention. Various modifications and alterations to the described embodiments will be apparent to those skilled in the art in view of the teachings herein. It will thus be appreciated that those skilled in the art will be able to devise numerous systems, arrangements and methods which, although not explicitly shown or described herein, embody the principles of the invention and are thus within the spirit and scope of the present invention. From the above description and drawings, it will be understood by those of ordinary skill in the art that the particular embodiments shown and described are for purposes of illustrations.

What is claimed is:

1. A method of securing soft tissue to bone, the method comprising:
  inserting a first suture anchor into bone at a first location, the first suture anchor comprising:
    a first proximal anchor body comprising a first inner lumen having a first proximal opening and external threads,
    a first distal anchor tip comprising a first distal exterior portion, a first rigid proximal shaft, and a first eyelet, wherein the first rigid proximal shaft is configured to be received within the first inner lumen, and
    a first elongated loading member threaded through the first eyelet, wherein
  the first elongated loading member comprises a first aperture;

inserting a second suture anchor into bone at a second location, the second suture anchor comprising:
- a second proximal anchor body comprising a second inner lumen having a second proximal opening and external threads,
- a second distal anchor tip comprising a second distal exterior portion, a second rigid proximal shaft, and a second eyelet, wherein the second rigid proximal shaft is configured to be received within the second inner lumen, and
- a first suture extending from the second suture anchor;

passing the first suture through the soft tissue;
passing the first suture through the first aperture of the first elongated loading member;
pulling on one end of the first elongated loading member to pull the first suture back through the soft tissue, into the first inner lumen, and through the first eyelet; and
pulling on the first suture to tension the first suture over the soft tissue, wherein the first suture extends from within the second inner lumen, through the second proximal opening, over the soft tissue, through the first proximal opening, into the first inner lumen, and through the first eyelet.

2. The method of claim 1, comprising a second suture extending from the first suture anchor.

3. The method of claim 2, wherein the second suture is threaded through the first eyelet and the first eyelet is of sufficient size such that both the first loading member and the second suture can slippably pass through the first eyelet.

4. The method of claim 2, comprising a second elongated loading member threaded through the second eyelet, wherein the second elongated loading member comprises a second aperture.

5. The method of claim 4, comprising:
passing the second suture through the second aperture on the second elongated loading member; and
pulling on one end of the second elongated loading member to pull the second suture through the second eyelet.

6. The method of claim 1, comprising:
inserting a third anchor into bone at a third location;
passing the first suture over the soft tissue; and
securing the first suture to the third anchor.

7. The method of claim 6, wherein after completion of the method, the first and second anchors are positioned beneath the soft tissue and the third anchor is positioned beyond an edge of the soft tissue.

8. The method of claim 6, wherein the first suture is secured to the third anchor by knotless fixation.

9. The method of claim 6, wherein the first suture is secured to the third anchor after tensioning the first suture over the soft tissue.

10. The method of claim 1, wherein the first rigid proximal shaft and the first inner lumen are configured such that when the first rigid proximal shaft is received by the first inner lumen, a space is provided between a side portion of the first rigid proximal shaft and sides of the first inner lumen to permit the first loading member to slippably pass through the first eyelet.

11. The method of claim 1, wherein the first distal exterior portion of the first distal anchor tip tapers from proximal to distal.

12. The method of claim 11, wherein a proximal end of the first distal exterior portion of the first distal anchor tip has a diameter larger than a diameter of the first inner lumen.

13. The method of claim 11, wherein a proximal end of the first distal exterior portion of the first distal anchor tip has a diameter larger than a diameter of the first rigid proximal shaft.

14. The method of claim 1, wherein the first rigid proximal shaft comprises opposing longitudinal grooves.

15. The method of claim 1, comprising forming first and second bore holes in the bone and wherein inserting the first suture anchor comprises inserting the first suture anchor into the first bore hole and inserting the second suture anchor comprises inserting the second suture anchor into the second bore hole.

16. The method of claim 1, wherein the first aperture comprises a loop in the first elongated loading member.

17. The method of claim 16, wherein the first elongated loading member comprises a suture.

18. The method of claim 1, comprising removing the first elongated loading member after pulling the first suture through the first eyelet.

19. The method of claim 1, wherein a lateral-medial bridge suture pattern is formed.

20. The method of claim 1, wherein a medial bridge suture pattern is formed.

21. The method of claim 1, wherein a two-anchor parallel horizontal repair is completed.

22. The method of claim 1, comprising forming a repair comprising two sutures extending between the first and second anchors.

* * * * *